(12) United States Patent
Cohen et al.

(10) Patent No.: US 9,078,843 B2
(45) Date of Patent: Jul. 14, 2015

(54) IMMUNOGENIC FRAGMENTS OF T-CELL RECEPTOR CONSTANT DOMAINS AND PEPTIDES DERIVED THEREFROM

(76) Inventors: Irun R. Cohen, Rehovot (IL); Francisco J. Quintana, Buenos Aires (AR)

( * ) Notice: Subject to any disclaimer, the term of this patent is extended or adjusted under 35 U.S.C. 154(b) by 1003 days.

(21) Appl. No.: 12/067,652

(22) PCT Filed: Sep. 21, 2006

(86) PCT No.: PCT/IL2006/001112
§ 371 (c)(1),
(2), (4) Date: Sep. 9, 2008

(87) PCT Pub. No.: WO2007/034489
PCT Pub. Date: Mar. 29, 2007

(65) Prior Publication Data
US 2009/0035359 A1  Feb. 5, 2009

Related U.S. Application Data

(60) Provisional application No. 60/719,342, filed on Sep. 22, 2005.

(51) Int. Cl.
*A61K 38/10* (2006.01)
*A61K 39/00* (2006.01)
*G01N 33/68* (2006.01)

(52) U.S. Cl.
CPC ........ *A61K 39/0008* (2013.01); *G01N 33/6854* (2013.01); *A61K 2039/53* (2013.01); *G01N 2333/7051* (2013.01); *G01N 2800/102* (2013.01)

(58) Field of Classification Search
None
See application file for complete search history.

(56) References Cited

U.S. PATENT DOCUMENTS

| | | | |
|---|---|---|---|
| 4,073,943 A | 2/1978 | Wretlind | |
| 4,168,308 A | 9/1979 | Wretlind | |
| 5,614,192 A | 3/1997 | Vandenbark | |
| 5,733,877 A | 3/1998 | Sato | |
| 5,961,970 A | 10/1999 | Lowell | |
| 5,985,552 A | 11/1999 | Howell | |
| 6,316,420 B1 | 11/2001 | Karin | |
| 2005/0260770 A1 | 11/2005 | Cohen | |

FOREIGN PATENT DOCUMENTS

| | | | |
|---|---|---|---|
| JP | A-H8-149981 A | 6/1996 | |
| JP | 11302299 B2 | 11/1999 | |
| JP | A-H11-302299 A | 11/1999 | |
| WO | 94/19470 A1 | 1/1994 | |
| WO | 95/16462 A1 | 6/1995 | |
| WO | 97/02016 A9 | 1/1997 | |
| WO | 97/43411 A1 | 11/1997 | |
| WO | 00/27870 A1 | 5/2000 | |
| WO | 01/57056 A1 | 8/2001 | |
| WO | 03/096967 A2 | 11/2003 | |
| WO | 2005/084137 A2 | 9/2005 | |

OTHER PUBLICATIONS

Onda et al., Proc Natl Acad Sci U S A. Mar. 28, 1995;92(7):3004-8.*
Mestas et al., The Journal of Immunology, 2004, 172: 2731-2738.*
Janeway et al., Immunobiology, 5th ed., 2001, Garland Publishing, pp. 116-117 and 174-176.*
Harding, Clin Exp Allergy 2003; 33: 557-565.*
Belmares et al., The Journal of Immunology, 2002, 169: 5109-5117.*
Ellmerich et al., Eur. J. Immunol. 2004. 34: 1839-1848.*
Janeway et al., Immunobiology, 5th ed., 2001, Garland Publishing, at pp. 117-118.*
Harold Chapman, Current Opinion in Immunology 1998, 10:93-102.*
The Memorandum from Deputy Commissioner for Patent Examination Policy Andrew H. Hirshfeld, dated Mar. 4, 2014, 19 pages in total with first page not numbered.*
"Evaluating subject Matter Eligibility Under 35 U.S.C. § 101," Mar. 19, 2014 update, pp. 1-93.*
Achiron et al., "T cell vaccination in multiple sclerosis relapsing—remitting nonresponders patients", Clin. Immunol, 113:155-160 (2004).
Ben-Nun et al. "Vaccination against autoimmune encephalomyelitis with T-lymphocyte line cells reactive against myelin basic protein",Nature, 292(5818):60-61 (Jul. 1981).
Bissonnette et al., "A T Helper Cell Hybridoma Produces an Antigen-Specific Regulatory Activity", J Immunol., 146(9):2898-2907 (May 1, 1991).
Cohen, I. R., "T-cell vaccination for autoimmune disease: a panorama", Vaccine, 20:706-710 (2002).
Hogervorst et al., "Modulation of Experimental Autoimmunity: Treating of Adjuvant Arthritis by Immunization with a Recombinant Vaccinia Virus", Infect Immun, 59:2029-2035 (Jun. 1991).
Holoshitz et. al., "Lines of T Lymphocytes Induce or Vaccinate Against Autoimmune Arthritis", Science, 219:56-58 (Jan. 7, 1983).
Ishii et al., "Cellular mechanisms for the formation of a soluble form derivative of T-cell receptor .alpha. chain by suppressor T cells", Proc Natl Acad Sci USA., 93:7207-7212 (Jul. 9, 1996).
Kumar et al., "Induction of a type 1 regulatory CD4 T cell response following V.beta.8.2 DNA vaccination results in immune deviation and protection from experimental autoimmune encephalomyelitis", Int Immunol, 13(6):835-841 (2001).

(Continued)

*Primary Examiner* — Zachary Skelding
(74) *Attorney, Agent, or Firm* — Rodney J. Fuller; Booth Udall Fuller, PLC

(57) ABSTRACT

The present invention is directed to an isolated T-Cell Receptor constant domain and to peptides derived therefrom and recombinant constructs encoding same, effective in therapy of T cell mediated inflammatory disease, autoimmunity and graft rejection. Therapeutic and prophylactic vaccine compositions and methods utilizing these proteins and peptides, DNA vaccines encoding same and T cell vaccines thereof are further provided.

4 Claims, 12 Drawing Sheets

(56) References Cited

OTHER PUBLICATIONS

Lohse et al., "Control of Experimental Autoimmune Encephalomyelitis by T Cells Responding to Activated T Cells", Science, 244:820-822 (1989).

Manolios et al., "T-cell antigen receptor transmembrane peptides modulate T-cell function and T cell-mediated disease", Nat Med 3:84-88 (1997).

Mimran et al., "DNA vaccination with CD25 protects rats from adjuvant arthritis and induces an antiergotypic response", J Clin Invest 113:924-932 (2004).

Minami et al., "The IL-2 Receptor Complex: Its Structure, Function, and Target Genes", Annu Rev Immunol, 11:245-267 (1993).

Mor et al., "IL-2 and TNF Receptors as Targets of Regulatory T-T Interactions: Isolation and Characterization of Cytokine Receptor-Reactive T Cell Lines in the Lewis Rat", J Immunol 157:4855-4861 (1996).

Quintana et al., "Inhibition of Adjuvant Arthritis by a DNA Vaccine Encoding Human Heat Shock Protein 60", J Immunol 169:3422-3428 (2002).

Quintana et al., "DNA Fragments of the Human 60-kDa Heat Shock Protein (HSP60) Vaccinate Against Adjuvant Arthritis: Identification of a Regulatory HSP60 Peptide", J Immunol 171:3533-3541 (2003).

Quintana et al., "Functional immunomics: Microarray analysis of IgG autoantibody repertoires predicts the future response of mice to induced diabetes", Proc Natl Acad Sci U S A 101 Suppl 2:14615-14621 (2004).

Reizis et al., "The peptide binding specificity of the MHC class II I-A molecule of the Lewis rat, RT1.B", Int Immunol 8 (12):1825-1832 (1996).

Shapira et al., "Prolongation of Survival of Rat Cardiac Allografts by T Cell Vaccination", J Clin Invest 91:388-390 (1993).

Singh, H. et al., "ProPred: prediction of HLA-DR binding sites", Bioinformatics 17(12):1236-1237 (2001).

Stribling et al., "Aerosol gene delivery in vivo", Proc. Natl. Acad. Sci. USA 89:11277-11281 (Dec. 1992).

Taniguchi, T. et al., "The IL-2/IL-2 Receptor System: A Current Overview", Cell 73:5-8 (Apr. 1993).

Van der Aa et al., "T cell vaccination in multiple sclerosis patients with autologous CSF-derived activated T cells: results from a pilot study", Clin Exp Immunol 131:155-168 (2003).

Van Eden et al., "Arthritis induced by a T-lymphocyte clone that responds to Mycobacterium tuberculosis and to cartilage proteoglycans", Proc Natl Acad Sci U S A, 82:5117-5120 (Aug. 1985).

Wolff et al., "Direct Gene Transfer into Mouse Muscle in Vivo", Science 247:1465-1468 (Mar. 1990).

Zhang et al., "MHC-Restricted Depletion of Human Myelin Basic Protein-Reactive T Cells by T Cell Vaccination", Science 261:1451-1454 (Sep. 1993).

Mimran et al., "Regulatory T Cells in Autoimmune Diseases: Anti-Ergotypic T Cells", International Reviews of Immunology, 24:159-179 (2005).

International Search Report for PCT/IL2006/001112 dated Oct. 16, 2007 (2 sheets).

Written Opinion of the International Searching Authority for PCT/IL2006/001112 dated Oct. 16, 2007 (3 sheets).

International Preliminary Examination Report for PCT/IL2006/001112 dated Mar. 26, 2008 (4 sheets).

T Cells and MHC Proteins. An MHC Protein Binds a Peptide and Interacts with a T Cell Receptor. http://www.ncbi.nlm.nih.gov/books/NBK26926/ (English version of Japanese citation: Molecular Biology of the Cell. 4th edition. Alberts B, Johnson A, Lewis J, et al. New York: Garland Science; 2002. pp. 1400-1402).

Class II MHC-peptide interaction. Immunology. Kuby, Janis et al., Third edition 1997, W.H. Freeman and company, NewYork, pp. 234-235.

Bevan, D. J. and Chisholm, P. M., "Co-expression of CD4 and CD8 molecules and de novo expression of MHC class II antigens on activated rat T cells," Immunology 59(4):621-625 (1986).

Ellmerich, Stephan et al., "High incidence of spontaneous disease in an HLA-DR15 and TCR transgenic multiple sclerosis model," J Immunol 174(4):1938-1946 (2005).

Mimran and Cohen (2005) Regulatory T cells in autoimmune diseases: anti-ergotypic T cells. Int Rev Immunol 24(3-4): 159-79.

Posnett et al., (1988) A novel method for producing anti-peptide antibodies. Production of site-specific antibodies to the T cell antigen receptor beta-chain. J Biol Chem 263(4): 1719-25.

* cited by examiner

US 9,078,843 B2

IMMUNOGENIC FRAGMENTS OF T-CELL RECEPTOR CONSTANT DOMAINS AND PEPTIDES DERIVED THEREFROM

RELATED APPLICATION DATA

This application is the U.S. national stage of PCT/IL2006/001112 filed on Sep. 21, 2006, which is based on and claims the benefit of U.S. Provisional Application No. 60/719,342 filed on Sep. 22, 2005, the content of each of which is expressly incorporated herein in its entirety by this reference.

FIELD OF THE INVENTION

The present invention is directed to immunomodulatory fragments of the T-Cell Receptor constant domain and to peptides derived therefrom and recombinant constructs encoding same, effective in therapy of T cell mediated inflammatory disease, autoimmunity and graft rejection. Therapeutic and prophylactic vaccine compositions and methods comprising these proteins and peptides, DNA vaccines encoding same and T cell vaccines thereof are further provided.

BACKGROUND OF THE INVENTION

While the normal immune system is closely regulated, aberrations in immune responses are not uncommon. In some instances, the immune system functions inappropriately and reacts to a component of the host as if it were, in fact, foreign. Such a response results in an autoimmune disease, in which the host's immune system attacks the host's own tissue. T cells, as the primary regulators of the immune system, directly or indirectly affect such autoimmune pathologies.

T cell-mediated inflammatory diseases refer to any condition in which an inappropriate T cell response is a component of the disease. This includes both diseases directly mediated by T cells, and also diseases in which an inappropriate T cell response contributes to the production of abnormal antibodies.

Numerous diseases are believed to result from autoimmune mechanisms. Prominent among these are rheumatoid arthritis, systemic lupus erythematosus, multiple sclerosis, Type I diabetes, myasthenia gravis, pemphigus vulgaris. Autoimmune diseases affect millions of individuals world-wide and the cost of these diseases, in terms of actual treatment expenditures and lost productivity, is measured in billions of dollars annually.

The existence of peripheral autoimmune T cells that recognize dominant self-antigens is a property of all healthy immune systems. The immunological dominance of self antigens such as myelin basic protein (MBP), HSP60 and insulin is associated with cellular networks consisting of the self-reacting T cells together with a network of regulatory T cells that recognize and respond to the autoimmune T cells. The two main regulatory T cells are anti-idiotypic T cells and anti-ergotypic T cells (ergon in Greek=work, action).

While anti-idiotypic T cells appear to recognize the self-antigen receptors present on the pathogenic endogenous autoimmune T cells, the anti-ergotypic T cells are defined as T cells that respond to activated, syngeneic T cells independent of their idiotypic specificities. Anti-ergotypic T cells recognize as antigens the markers of the state of activation, ergotopes, of activated T cells. An example of such ergotope is the α chain of the IL-2 receptor (CD25), whose expression is up-regulated in activated T cells during T cell activation (Minami et al 1993; Taniguchi and Minami 1993). Anti-ergotypic T cells do not appear to respond to their target T cells in the resting state.

A comparison between the anti-ergotypic regulatory T cells and the anti-idiotypic regulatory T cells, although having some features in common, also reveals a difference in cytokine profile. While anti-idiotypic regulatory T cells secrete Th1 cytokines (Cohen 2001; Kumar et al 2001), the anti-ergotypic regulatory T cells secrete mainly IL-10, a Th2 cytokine.

Experimental autoimmune encephalomyelitis (EAE) is a T cell mediated autoimmune disease of the central nervous system that serves as an experimental model for multiple sclerosis. Autoimmune diseases such as EAE could be prevented or treated by administering attenuated, but potentially virulent autoimmune T cells specific for the disease-related self-antigens, a procedure called T-cell vaccination (TCV). It was discovered some years ago that T-cell vaccination can be used to treat autoimmunity, graft rejection, or allergies. The effect of TCV was hypothesized to be partially mediated by the in vivo activation of anti-ergotypic T cells (Lohse et al 1989).

Anti-ergotypic regulation is thought to be essential to successful T-cell vaccination (Zhang et al 1993; Van der Aa et al 2003), an approach currently being used to treat a variety of autoimmune diseases (Zhang et al 1993) and to prevent graft rejection (Shapira et al 1993) and allergy (Zhang et al 1993). Thus, agents that can activate anti-ergotypic regulation could have a wide use for all conditions where it would be desirable to modulate immune inflammation.

A preferable method for treating autoimmune diseases includes modulating the immune system of a patient to assist the patient's natural defense mechanisms. Traditional reagents and methods used to attempt to regulate an immune response in a patient also result in unwanted side effects and have limited effectiveness. For example, immunosuppressive reagents (e.g. cyclosporin A, azathioprine, and prednisone) used to treat patients with autoimmune diseases also suppress the patient's entire immune response, thereby increasing the risk of infection. In addition, immunopharmacological reagents used to treat cancer (e.g. interleukins) are short-lived in the circulation of a patient and are ineffective except in large doses. Due to the medical importance of immune regulation and the inadequacies of existing immunopharmacological reagents, reagents and methods to regulate specific parts of the immune system have been the subject of study for many years.

Stimulation or suppression of the immune response in a patient can be an effective treatment for a wide variety of medical disorders. T lymphocytes (T cells) are one of a variety of distinct cell types involved in an immune response. The activity of T cells is regulated by an antigen, presented to a T cell in the context of a major histocompatibility complex (MHC) molecule. The T cell receptor (TCR) then binds to the MHC-antigen complex. Once antigen is complexed to MHC, the MHC-antigen complex is bound by a specific TCR on a T cell, thereby altering the activity of that T cell.

WO 01/57056 of Karin discloses a method of treating rheumatoid arthritis of an individual. The method comprises the step of expressing within the individual at least an immunologically recognizable portion of a cytokine from an exogenous polynucleotide encoding the at least a portion of the cytokine, wherein a level of expression of the at least a portion of the cytokine is sufficient to induce the formation of anti-cytokine immunoglobulins which serve for neutralizing or ameliorating the activity of a respective and/or cross reactive endogenous cytokine, to thereby treat rheumatoid arthritis.

U.S. Pat. No. 6,316,420 to Karin and coworkers further discloses DNA cytokine vaccines and use of same for protective immunity against multiple sclerosis.

WO 00/27870 of Naparstek and colleagues discloses a series of related peptides derived from heat shock proteins Hsp65 and Hsp60, their sequences, antibodies, and use as vaccines for conferring immunity against autoimmune and/or inflammatory disorders such as arthritis. These peptides are intended by the inventors to represent the shortest sequence or epitope that is involved in protection of susceptible rat strains against adjuvant induced arthritis. These sequences further disclose what the inventors identify as the common "protective motif".

WO 03/096967 of the inventors and others discloses DNA vaccines for treating a T cell mediated inflammatory autoimmune where the DNA vaccine includes a recombinant construct comprising a nucleic acid sequence encoding a mammalian heat shock protein.

There are a number of disclosures using peptides derived from specific T Cell Receptors as therapeutics for immune-related disease. For example, U.S. Pat. No. 5,614,192 discloses peptides capable of reducing the severity of a T cell mediated disease having an amino acid sequence comprising at least part of the second complementarity determining region of a T cell receptor characteristic of such T cell mediated disease.

WO 94/19470 discloses prophylactic and therapeutic compositions for the treatment of autoimmune diseases which comprises a prophylactically or therapeutically effective amount of a soluble T-cell receptor α-chain produced by suppressor T-cells. Specifically, the '470 application discloses a composition comprising a soluble fragment of the variable region of a TCR α-chain obtained from KLH-specific suppressor T cells. More specifically, the use of a chimeric protein consisting of a variable region fragment of a mouse TCR α chain, denoted Vα14Jα281, fused to the constant region of mouse IgG, is disclosed.

WO 97/43411 discloses polypeptides that contain substantially part or the whole of the constant region of a T-cell receptor α-chain, having immunosuppressive effects, but do not substantially cause any production of antibodies against themselves even when administered. This application discloses DNAs coding for the polypeptides as well as pharmaceutical compositions containing these polypeptides as the active ingredient.

JP11302299 discloses polypeptides having immunosuppressive activity that substantially contain part or the whole of the constant region of T-cell receptor β-chain but do not substantially contain the other regions of the above β-chain.

A nine amino acid peptide derived from the transmembrane domain of the TCRα chain, denoted core peptide (CP), inhibits T-cell antigen specific activation in vitro and in vivo (Manolios et al., 1997) by co-localizing with the TCR molecules, thereby inhibiting the proper assembly of the TCR-CD3 complex.

U.S. Patent Application Publication No. 2005/0260770 to some of the inventors of the present invention discloses an antigen array system and diagnostic uses thereof. The application provides a method of diagnosing an immune disease or a predisposition thereto in a subject, comprising determining a capacity of immunoglobulins of the subject to specifically bind each antigen probe of an antigen probe set. The antigen probe set comprises a plurality of antigen probes selected from the group consisting of at least a portion of a cell/tissue structure molecule, at least a portion of a heat shock protein, at least a portion of an immune system molecule, at least a portion of a homopolymeric polypeptide, at least a portion of a hormone, at least a portion of a metabolic enzyme, at least a portion of a microbial antigen, at least a portion of a molluscan antigen, at least a portion of a nucleic acid, at least a portion of a plant antigen, at least a portion of a plasma molecule, and at least a portion of a tissue antigen, wherein the binding capacity of the immunoglobulin of the subject is indicative of the immune disease or the predisposition thereto. Among the numerous antigen probes disclosed by the '770 publication as potential diagnostic markers are peptides derived from a T cell receptor, preferably from the constant domain of rat T cell receptor beta chains.

Nowhere in the background art is it disclosed or suggested that specific peptides having therapeutic properties suitable for the treatment of autoimmune inflammatory disease may be derived from the constant domain of a T Cell Receptor polypeptide.

Recently, the inventors and coworkers (Mimran et al 2004) discovered that one of the target ergotopes on activated T cells is the CD25 molecule. In that publication, it was demonstrated that DNA vaccination with the ergotope CD25 protects rats from adjuvant arthritis and increases the anti-ergotypic response in rats where adjuvant arthritis was induced. This increased anti-ergotypic T cell response was defined by the heightened proliferative response to activated A6 T cell clones compared to the response observed in rats not vaccinated with the CD25-DNA vaccine. The increased anti-ergotopic T cell response was characterized by a reduction in the secretion of IFNγ and an increase in the secretion if IL-10, or in other words, a cytokine shift from a Th1-like to a Th2-like phenotype.

There exists a long-felt need for effective means of curing or ameliorating T cell mediated inflammatory or autoimmune diseases and ameliorating T cell mediated pathologies. Usually, only the symptoms can be treated, while the disease continues to progress, often resulting in severe debilitation or death. Such a treatment should ideally control the inappropriate T cell response, rather than merely reducing the symptoms.

SUMMARY OF THE INVENTION

The present invention provides vaccine compositions suitable for preventing and treating T cell mediated pathologies, including e.g. autoimmunity and graft rejection. Specifically, the present invention provides immunogenic compositions comprising the T-Cell Receptor constant domain and peptides derived therefrom, effective in preventing or treating T cell mediated inflammatory disease. The present invention also provides recombinant constructs encoding these proteins and peptides and DNA vaccines and T cell vaccines useful in therapy of inflammatory diseases. In certain embodiments, novel peptide antigens useful in vaccination and diagnosis are provided.

The present invention is based, in part, on the unexpected discovery that immunization with the constant domain of the T-Cell Receptor (TCR) provides protection against T cell mediated inflammatory autoimmune diseases. Surprisingly, in accordance with the present invention it has been discovered that both the C1 and C2 variant molecules of the constant domain of the β chain of the T Cell Receptor as well as recombinant constructs encoding these proteins elicit protective immunity against T cell mediated inflammatory diseases. The principles of the invention are exemplified for the animal disease model of adjuvant arthritis (AA), a T cell mediated inflammatory autoimmune disease that serves as an experimental model for rheumatoid arthritis. Moreover, similar therapeutic and prophylactic properties have also been observed using synthetic peptides derived from regions of the constant domain of the T Cell Receptor that exhibit a Major Histocompatibility Complex class II (MHC-II) binding motif.

According to a first aspect, the present invention is directed to vaccine compositions comprising peptide antigens derived from the constant domain of a chain of a TCR, useful for treating and preventing the progression of T cell mediated pathologies.

Specifically, there is provided a vaccine composition comprising (a) at least one pharmaceutically acceptable carrier, adjuvant, excipient or diluent; (b) at least one immunogen selected from the group consisting of:

(i) an isolated constant domain of a chain of a human TCR; and
(ii) a peptide comprising an immunogenic fragment of the constant domain of a chain of a TCR.

It should be understood that the terms "isolated TCR constant domain" and "a peptide comprising an immunogenic fragment of the constant domain" as used herein refer to fragments of a TCR chain lacking the variable region of a TCR chain and fragments thereof. Thus, the compositions of the invention do not substantially include sequences encoded by TCR V D and J gene segments or specific portions thereof. A "peptide comprising an immunogenic fragment of the constant domain" refers to an amino acid sequence corresponding to a portion of the constant domain, but excluding the full-length constant domain.

Preferably, the immunogen is a peptide comprising an immunogenic fragment of the constant domain of a human T cell receptor.

According to certain embodiments, the peptide comprises at least one MHC class II binding motif.

Advantageously, the polypeptides or peptides of the invention comprises multiple MHC-II binding motifs, or overlapping MHC-II binding motifs.

According to certain embodiments the polypeptides or peptides of the invention comprise at least one peptide sequence derived from at least one TCR constant domain. According to certain preferred embodiments the polypeptides or peptides of the invention comprise at least one peptide sequence derived from at least one TCR constant domain, the polypeptide or peptide comprising a plurality of MHC-II binding motifs. According to additional preferred embodiments the polypeptides or peptides of the invention comprise a plurality of peptide sequences derived from at least one TCR constant domain, the polypeptide or peptide comprising a plurality of MHC-II binding motifs. According to still additional preferred embodiments the polypeptides or peptides of the invention comprise a plurality of peptide sequences derived from a plurality of TCR constant domains, the polypeptide or peptide comprising a plurality of MHC-II binding motifs.

According to one embodiment, the peptides of the invention may be derived from the constant domain of a chain of a T Cell Receptor, wherein the chain is selected from the group consisting of alpha chains, beta chains, gamma chains and delta chains.

According to preferred embodiments, the chain is selected from the group consisting of T-cell receptor alpha chains, T-cell receptor beta-1 chains, T-cell receptor beta-2 chains, T-cell receptor gamma-1 chains, T-cell receptor gamma-2 chains, and T-cell receptor delta chains.

In various embodiments, specific peptides derived from TCR constant domain chains provided by the present invention, the peptides comprising at least one MHC class II binding motif, are presented in Tables 2-9 hereinbelow.

According to one embodiment, the chain is selected from the group consisting of T-cell receptor alpha chains. According to particular embodiments, the chain is the T-cell receptor alpha chain and the peptide is selected from the group consisting of the peptides having the sequence set forth in any one of SEQ ID NOS: 1-27 and analogs, derivatives and salts thereof. In certain other particular embodiments, the peptide is selected from the group consisting of the peptides having the sequence set forth in any one of SEQ ID NOS: 1-12 and 15-27 and analogs, derivatives and salts thereof.

According to another embodiment, the chain is selected from the group consisting of T-cell receptor beta chains.

According to particular embodiments, the chain is the T-cell receptor beta-1 chain and the peptide is selected from the group consisting of the peptides having the sequence set forth in any one of SEQ ID NOS: 28-60 and analogs, derivatives and salts thereof.

According to particular embodiments, the chain is the T-cell receptor beta-2 chain and the peptide is selected from the group consisting of the peptides having the sequence set forth in any one of SEQ ID NOS:31-49, SEQ ID NOS:51-59, and SEQ ID NOS:61-64 and analogs, derivatives and salts thereof.

According to another embodiment, the chain is selected from the group consisting of T-cell receptor delta chains.

According to particular embodiments, the chain is the T-cell receptor delta chain and the peptide is selected from the group consisting of the peptides having the sequence set forth in any one of SEQ ID NOS:65-92 and analogs, derivatives and salts thereof.

According to another embodiment, the chain is selected from the group consisting of T-cell receptor gamma chains.

According to particular embodiments, the chain is the T-cell receptor gamma chain and the peptide has an amino acid sequence as set forth in any one of SEQ ID NOS:93-130 and analogs, derivatives and salts thereof.

According to other particular embodiments, the chain is the T-cell receptor gamma chain and the peptide has an amino acid sequence as set forth in any one of SEQ ID NOS:93-131 and analogs, derivatives and salts thereof.

According to further particular embodiments, the chain is the T-cell receptor gamma chain and the peptide has an amino acid sequence as set forth in any one of SEQ ID NOS:93-100, SEQ ID NOS: 104-105, SEQ ID NOS:107-109, SEQ ID NOS:112-125, SEQ ID NOS:127-129, SEQ ID NOS:131-140, and analogs, derivatives and salts thereof.

According to other particular embodiments, the chain is the T-cell receptor gamma chain and the peptide has an amino acid sequence as set forth in any one of SEQ ID NOS:94-100, SEQ ID NOS: 104-105, SEQ ID NOS:107-109, SEQ ID NOS:112-130, SEQ ID NOS:133-146 and analogs, derivatives and salts thereof.

It is noted that the peptides identified as comprising the required MHC class II binding motif are arbitrarily presented herein as nine amino acids in length. It is explicitly to be understood that the peptides used in accordance with the present invention may include extensions on either or both termini, as well as deletions or truncations, as long as they preserve the intended function of suppressing autoimmune inflammatory disease.

In other particular embodiments, there are provided novel immunogenic peptides derived from TCR gamma chain constant domain, having an amino acid sequence as set forth in any one of SEQ ID NOS:157-167 and analogs, derivatives and salts thereof.

In certain other particular embodiments, there are provided novel fusion peptides derived from TCR constant region sequences. The term "fusion peptide" as used herein denotes a polypeptide or peptide in which two or more polypeptide or peptide sequences are linked to one another directly or indirectly, preferably directly, by chemical bonding, preferably peptide bonding, in a combination which does not exist naturally.

In a preferable embodiment, there is provided a fusion peptide comprising a plurality of immunogenic determinants derived from at least one TCR constant domain. In various particular embodiments, each immunogenic determinant comprises a peptide fragment of the TCR constant domain, or an analog or derivative thereof.

In other particular embodiments, the fusion peptide comprises an amino acid sequence as set forth in any one of SEQ ID NOS:157-167 and analogs, and derivatives thereof.

In another preferable embodiment, there is provided a fusion peptide comprising a plurality of peptide sequences derived from at least one T Cell Receptor constant domain, the fusion peptide comprising a plurality of MHC-II binding motifs. In various particular embodiments, each peptide sequence derived from the at least one TCR constant domain comprises a peptide fragment of said TCR constant domain, or an analog or derivative thereof. In certain other particular embodiments, at least one peptide sequence derived from the at least one TCR constant domain comprises an amino acid sequence as set forth in any one of SEQ ID NOS:1-146.

According to preferred embodiments, the peptide is useful for preventing or treating a T cell-mediated inflammatory disease. According to specific embodiments, the peptide is an ergotope capable of eliciting an anti-ergotypic T cell response and inhibiting the development of a T cell mediated inflammatory disease. In one embodiment, the anti-ergotypic T cell response is defined by recognition of activated histocompatible T cells as observed in proliferation response assays. In yet another embodiment, the anti-ergotypic response may be defined by a shift in the cytokine phenotype from IFNγ and TNFα towards IL-10, thereby driving the differentiation of activated T cells from a Th1-like to a Th2-like phenotype.

In preferred embodiments, the composition is useful for preventing or treating a T cell-mediated inflammatory disease. According to particular embodiments, the composition inhibits or treats the T cell-mediated inflammatory disease by eliciting an anti-ergotypic T cell response.

The compositions and methods of the present invention are effective in T-cell mediated inflammatory diseases including but not limited to: multiple sclerosis, rheumatoid arthritis, juvenile rheumatoid arthritis, autoimmune neuritis, systemic lupus erythematosus, psoriasis, Type I diabetes, Sjogren's disease, thyroid disease, myasthenia gravis, sarcoidosis, autoimmune uveitis, inflammatory bowel disease (Crohn's and ulcerative colitis) autoimmune hepatitis, allergies and graft rejection.

In various embodiments, the vaccine composition further comprises at least one adjuvant capable of enhancing the immunogenicity of the administered peptide. In a particular embodiment, the adjuvant is a metabolizable lipid emulsion.

The present invention furthermore provides nucleic acids encoding the above-mentioned peptides. In another aspect, there are provided recombinant constructs comprising nucleic acid sequences encoding these peptides, the nucleic acid sequences operatively linked to one or more transcription control sequences.

In another aspect, the invention provides DNA vaccine compositions encoding the TCR constant domain and peptides derived therefrom, as detailed herein.

DNA vaccination represents a novel means of expressing antigens in vivo for the generation of both humoral and cellular immune responses. The present invention provides DNA vaccines comprising a recombinant construct including an isolated nucleic acid sequence encoding the constant domain of a chain of a T Cell receptor or an active fragment thereof, the nucleic acid sequence being operatively linked to one or more transcription control sequences; and in a suitable expression system, enabling in vivo expression of the encoded peptide or the active fragment thereof in a human host.

More specifically, the present invention provides a DNA vaccine composition comprising (a) at least one pharmaceutically acceptable carrier (b) at least one recombinant construct comprising an isolated nucleic acid sequence encoding at least one immunogen selected from the group consisting of:
  (i) the constant domain of a chain of a T Cell Receptor (TCR); and
  (ii) a peptide comprising an immunogenic fragment of the constant domain of a chain of a TCR,
wherein the nucleic acid sequence is operatively linked to one or more transcription control sequences.

Not wishing to be bound by any theory or mechanism of action, in certain embodiments the present invention uses a nucleic acid molecule encoding the constant domain of a chain of the T Cell Receptor or the active fragment in order to elicit an anti-ergotypic T cell response with the encoded protein or peptide as an ergotope.

In certain embodiments, said carrier comprises a delivery vehicle that delivers the nucleic acid sequences to a subject. In particular embodiments, said delivery vehicle is selected from the group consisting of liposomes, micelles and cells.

In certain other particular embodiments, said recombinant construct is a eukaryotic expression vector.

In another aspect, there is provided method of treating or preventing the development of a T-cell mediated inflammatory disease, the method comprising administering to a subject in need thereof a therapeutically effective amount of a vaccine composition of the invention, as detailed herein.

In one particular embodiment, said T cell-mediated inflammatory disease is an autoimmune disease. In other particular embodiments, said T cell-mediated inflammatory disease is selected from the group consisting of: multiple sclerosis, rheumatoid arthritis, juvenile rheumatoid arthritis, autoimmune neuritis, systemic lupus erythematosus, psoriasis, Type I diabetes, Sjogren's disease, thyroid disease, myasthenia gravis, sarcoidosis, autoimmune uveitis, inflammatory bowel disease (Crohn's and ulcerative colitis), autoimmune hepatitis, graft rejection and allergies.

In various embodiments of the present invention, said subject is selected from the group consisting of humans and non-human mammals.

The compositions of the invention may be administered to said subject after appearance of disease symptoms or, in alternate embodiments, prior to appearance of disease symptoms.

In certain other particular embodiments, said composition is administered by intravenous injection, intramuscular injection, aerosol, oral, percutaneous or topical administration.

In another aspect, there is provided a method of enhancing anti-ergotypic T cells activity in a subject in need thereof, the method comprising administering to the subject in need thereof a therapeutically effective amount of a vaccine composition of the invention, as detailed herein. In one embodiment, the anti-ergotypic T cell response is defined by recognition of activated T cells as observed in proliferation response assays.

In another aspect, the invention provides a method of treating or preventing the development of a T-cell mediated inflammatory disease, the method comprising administering to a subject in need thereof a therapeutically effective amount of at least one recombinant construct, the recombinant construct comprising an isolated nucleic acid sequence encoding at least one immunogen of the invention as detailed herein, wherein the nucleic acid sequence is operatively linked to one or more transcription control sequences.

In certain embodiments, said construct is administering to said subject in the form of a pharmaceutical composition further comprising at least one pharmaceutically acceptable carrier, excipient or diluent.

In one particular embodiment, said T cell-mediated inflammatory disease is an autoimmune disease. In other particular embodiments, said T cell-mediated inflammatory disease is selected from the group consisting of: multiple sclerosis, rheumatoid arthritis, juvenile rheumatoid arthritis, autoimmune neuritis, systemic lupus erythematosus, psoriasis, Type I diabetes, Sjogren's disease, thyroid disease, myasthenia gravis, sarcoidosis, autoimmune uveitis, inflammatory bowel disease (Crohn's and ulcerative colitis), autoimmune hepatitis, graft rejection and allergies.

In various embodiments of the present invention, said subject is selected from the group consisting of humans and non-human mammals.

The compositions of the invention may be administered to said subject after appearance of disease symptoms or, in alternate embodiments, prior to appearance of disease symptoms.

In certain other particular embodiments, said composition is administered by intravenous injection, intramuscular injection, aerosol, oral, percutaneous or topical administration.

Not wishing to be bound by theory, in various embodiments the administration of the composition increases the anti-ergotypic T cell response in said individual and inhibits the development of T cell mediated inflammatory disease in the individual. In one embodiment, the anti-ergotypic T cell response is defined by recognition of activated T cells as observed in proliferation response assays.

Another aspect of the present invention is a method of enhancing anti-ergotypic T cells activity in a subject in need thereof, the method comprising administering to a subject in need thereof a therapeutically effective amount of at least one recombinant construct, the recombinant construct comprising an isolated nucleic acid sequence encoding at least one immunogen of the invention as detailed herein, wherein the nucleic acid sequence is operatively linked to one or more transcription control sequences. In one embodiment, the anti-ergotypic T cell response is defined by recognition of activated T cells as observed in proliferation response assays.

In yet another aspect, the invention provides a method for treating or preventing the development of a T-cell mediated inflammatory disease comprising the steps of
 (a) obtaining cells from a subject or from a donor histocompatible with the subject;
 (b) transfecting the cells in vitro with a recombinant construct comprising an isolated nucleic acid sequence encoding at least one immunogen of the invention as detailed herein, the nucleic acid sequence being operatively linked to one or more transcription control sequences; and
 (c) introducing a therapeutically effective number of the transfected cells to said subject.

In other aspects, the present invention is directed to cell vaccines and methods of using same, utilizing T cells and/or other antigen presenting cells exposed to an immunogen of the invention as detailed herein.

In another aspect there is provided a pharmaceutical composition comprising as an active ingredient attenuated activated cells selected from the group consisting of antigen presenting cells and T cells activated ex vivo to induce Major Histocompatibility Complex II expression, wherein the cells have been exposed ex vivo to an effective amount of at least one immunogen selected from a group consisting of:
 (i) the constant domain of a chain of a T Cell Receptor (TCR); and
 (ii) a peptide comprising an immunogenic fragment of the constant domain of a chain of a TCR.

In another aspect there is provided a pharmaceutical composition comprising a population of T cells obtained by culturing a first population of T cells ex vivo in the presence of a second population of cells, the second population being attenuated activated cells histocompatible with the cells of the first population, wherein the cells of said second population are selected from the group consisting of antigen presenting cells and T cells activated ex vivo to induce Major Histocompatibility Complex II expression, and wherein said cells of said second population have been exposed ex vivo to at least one immunogen selected from a group consisting of:
 (i) the constant domain of a chain of a T Cell Receptor (TCR); and
 (ii) a peptide comprising an immunogenic fragment of the constant domain of a chain of a TCR.

These cell vaccine compositions may be administered to a in a subject in need thereof for treating or preventing the progression of a T cell mediated inflammatory disease, wherein the administered cells are histocompatible with the subject.

In one embodiment, there is provided a method of treating or preventing a T-cell mediated inflammatory disease comprising the steps of:
 (a) isolating T cells from first subject or from a donor histocompatible with said subject;
 (b) activating the T cells ex vivo to induce Major Histocompatibility Complex (MHC) II expression and exposing said activated cells to the immunogen; and
 (c) attenuating said T cells and introducing a therapeutically effective amount of said cells into said subject, thereby treating or preventing the progression of said disease.

In another embodiment, the attenuation step is performed after activating the cells and prior to exposing said cells to said immunogen.

In another embodiment, the method comprises:
 (a) isolating a first population of T cells from the subject or from a donor histocompatible with said subject;
 (b) culturing the first population of T cells in the presence of a second population of histocompatible attenuated activated T cells or antigen presenting cells and the immunogen; and
 (c) introducing a therapeutically effective amount of said first population of T cells into the subject thereby treating or preventing the progression of said disease.

In another embodiment, step (b) comprises culturing the first population of T cells in the presence of a second population of histocompatible attenuated activated T cells or antigen presenting cells that were previously exposed to said immunogen.

In another aspect, the novel peptides of the invention may be used for the diagnosis of conditions associated with an immune response to these peptides in a subject, as detailed herein.

In one embodiment, there is provided a method of diagnosing a condition associated with an immune response in a subject in need thereof, the method comprising:

a) obtaining an antibody-containing biological sample from a subject;
b) contacting the sample, under conditions such that an antigen-antibody complex may be formed, with an antigen probe comprising a peptide having an amino acid sequence as set forth in any one of SEQ ID NOS:1-146 and 157-167, and analogs, derivatives and salts thereof;
c) determining the capacity of the antigen probe to specifically bind said antibody-containing biological sample; wherein the capacity is indicative of the condition.

In a preferable embodiment, step c) comprises determining the capacity of at least one antibody of the IgG isotype in the biological sample to specifically bind the antigen probe.

In certain embodiments, said condition is associated with an increased T cell-mediated immune response. In another embodiment, said condition is a T cell mediated inflammatory disease. In another particular embodiment, said condition is associated with an increased anti-ergotypic T cell activity.

In another aspect, the invention provides a diagnostic kit comprising a peptide antigen having an amino acid sequence as set forth in any one of SEQ ID NOS: 1-146 and 157-167, and analogs, derivatives and salts thereof, and means for determining whether the peptide antigen binds specifically to an antibody-containing biological sample.

These and other embodiments of the present invention will become apparent in conjunction with the figures, description and claims that follow.

DETAILED DESCRIPTION OF THE INVENTION

Figure 1A:
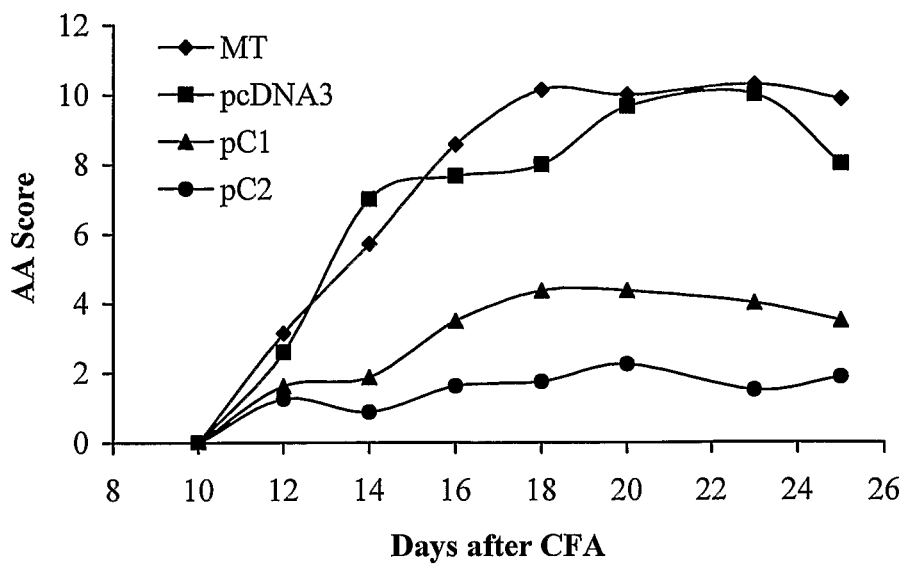
FIG. 1 illustrates the inhibition of AA by vaccination with pβC1 and pβC2. Note that in FIG. 1 pC1 denotes pβC1 and pC2 denotes pβC2.

The present invention relates to novel compositions and methods for controlling regulatory T cell activity. It is now shown for the first time that vaccine compositions containing the constant domain of a chain of a T Cell Receptor (TCR), active peptides derived thereof, or nucleic acid molecules encoding these proteins or peptides are effective therapeutic reagents for treating T cell-mediated inflammatory disease. The efficacy of T cell vaccines utilizing TCR-derived polypeptides or peptides is also demonstrated for the first time.

The invention is based, in part, on the surprising discovery that the constant domain of both beta-1 and beta-2 T cell receptor variant chains (C1 and C2, respectively) may be used in therapy of T cell mediated pathologies. Unexpectedly it was discovered that vaccination with C1 and C2 domains, as well as specific peptides derived therefrom, and recombinant constructs encoding same, is capable of inhibiting T cell mediated inflammation in adjuvant arthritis (AA), an animal model of an autoimmune disease. It was further discovered unexpectedly, that T cell lines directed to these epitopes ameliorate AA when adoptively transferred to rats.

In accordance with the present invention, it has also been discovered that peptides derived from the Major Histocompatibility Complex (MHC) Class-II binding regions (Reizis et al 1996; Singh and Raghava 2001) of the constant domain of the T cell receptor are effective therapeutic agents for treating and preventing the development of T cell-mediated disease.

Identification of TCR Constant Domain Peptides

In one aspect, the invention is directed to immunogenic peptides derived from the constant domain of a TCR chain.

The term "immunogenic" or "immunogenicity" refers to the ability of a peptide to induce an antigen-specific cell-mediated and/or antibody immune response upon administration in an appropriate form and by an appropriate route to a mammal. In other words, administration of a peptide of the invention elicits activation of T cells and/or antibodies directed against one or more antigenic determinants (epitopes) included within said peptide. It is to be understood, therefore, that the immunogenic peptides of the invention are capable of eliciting an immune response to one or more epitopes of a TCR chain constant domain. This term further includes the term "antigenic" or "antigenicity" which refers to the ability of the peptide to be recognized by, which generally means bound by, an antibody.

In one particular embodiment, the TCR constant domain-derived peptides of the invention are characterized in that they elicit Abs against one or more antigenic determinants included in said peptides when administered to a subject. In another embodiment, said Abs specifically bind to at least one TCR constant domain epitope. In a preferable embodiment, the Abs are of the IgG isotype.

In another particular embodiment, the TCR constant domain-derived peptides of the invention are characterized in that they comprise one or more antigenic determinants which are specifically bound by at least one Ab isolated from a subject. In a preferable embodiment, the Ab is of the IgG isotype. In another embodiment, said Ab is isolated from the subject prior to administering a TCR constant domain-derived peptide to said subject. In another particular embodiment, the subject is afflicted with a condition associated with an increased T cell-mediated immune response. In another particular embodiment, said condition is a T cell-mediated inflammatory disease.

In another particular embodiment, the TCR constant domain-derived peptides of the invention are characterized in that they elicit an immune response to one or more epitopes of a TCR chain constant domain as measured by increased peptide-specific T cell activity. According to another particular embodiment, the peptide-specific T cell activity is an anti-ergotypic T cell activity.

The terms "anti-ergotypic T cell response" and "anti-ergotypic T cell activity" refer to the activation of regulatory anti-ergotypic T cells. In various embodiments, the anti-ergotypic T cell response may be defined by a heightened proliferative response to histocompatible (autologous or syngeneic) activated T cells. For example, the proliferative response to various activated T cell clones such as A2b which recognizes Mt 176-190, or p277 which recognizes residues 436-460 of HSP60 may be determined when using animal models. Alternately, the anti-ergotypic response may be defined by a shift in the cytokine phenotype from IFNγ and TNFα towards IL-10, thereby driving the differentiation of the histocompatible activated T cells from a Th1-like to a Th2-like phenotype.

Accordingly, in certain embodiments of the present invention, identification of TCR constant domain-derived peptides suitable for human vaccination may optionally be performed by at least one of the following:

a) Determining the antigenicity of the peptides. By means of a non-limitative example, this may optionally be performed by screening candidate TCR constant domain-derived peptides for their ability to bind e.g. IgG Abs of a subject afflicted with a T-cell mediated inflammatory disease, using, for example, antigen-array technology. A non-limitative example of peptide screening using antigen-array-based methods is presented in Example 12 herein;

b) Determining the immunogenicity of the peptides. By means of a non-limitative example, this may optionally be performed by obtaining lymphocytes from a subject, raising a T cell line directed to a candidate TCR constant domain-derived peptide, and determining the ability of the resulting T cell line to proliferate to histocompatible activated T cells. Non-limitative examples of peptide screening using anti-ergotypic T cell lines are presented in Examples 8-10 and 13 herein.

According to another aspect, the present invention provides an isolated peptide derived from the constant domain of a chain of a T Cell Receptor, wherein the peptide exhibits at least one MHC class II (MHC-II) binding motif.

Thus, according to certain other embodiments, isolation of TCR constant domain-derived peptides suitable for human vaccination may be performed using an MHC-II prediction algorithm. A non-limitative example of peptide screening using the ProPred Algorithm for prediction of HLA-DR binding regions in the constant domain of the T Cell Receptor is presented in Example 11 herein.

In various particular embodiments, the peptides of the invention may be derived from various parts of the constant domain of a TCR chain. In certain particular embodiments, the peptides are derived from the cytoplasmic region of the constant domain of a TCR chain. In other particular embodiments, the peptides of the invention are derived the extracellular region of the constant domain of a TCR chain. In further particular embodiments, the peptides of the invention are derived the transmembrane region of the constant domain of a TCR chain.

A nine amino acid peptide derived from the transmembrane domain of the TCRα chain, denoted core peptide (CP) was reported to inhibit T-cell antigen specific activation in vitro and in vivo by co-localizing with the TCR molecules, thereby inhibiting the proper assembly of the TCR-CD3 complex. It is to be understood that the peptides of the present invention explicitly exclude the peptide denoted CP, having an amino acid sequence GLRILLLKV (SEQ ID NO:156). In certain embodiments, the peptides of the invention are derived from a sequence other than the transmembrane region of the constant domain of a TCR alpha chain.

In certain other particular embodiments, the invention provides a fusion peptide derived from a TCR constant domain, said fusion peptide comprising a plurality of immunogenic determinants derived from at least one T Cell Receptor constant domain.

The term "fusion peptide" as used herein denotes a polypeptide or peptide in which two or more polypeptide or peptide sequences are linked to one another directly or indirectly, preferably directly, by chemical bonding, preferably peptide bonding, in a combination which does not exist naturally.

In certain specific embodiments, said fusion peptide has an amino acid sequence as set forth in any one of SEQ ID NOS:157-167. A non-limitative example of a fusion peptide according to the invention is the peptide denoted by SEQ ID NO:165, which comprises two immunogenic determinants derived from TCR gamma constant domain, the immunogenic determinants denoted by SEQ ID NOS:160 and 162.

According to certain embodiments the present invention provides recombinant or synthetic polypeptides or peptides comprising at least one peptide sequence derived from at least one T Cell Receptor constant domain. According to certain preferred embodiments the present invention provides recombinant polypeptides or peptides comprising at least one peptide sequence derived from at least one T Cell Receptor constant domain, the recombinant polypeptide or peptide comprising a plurality of MHC-II binding motifs. According to additional preferred embodiments the present invention provides recombinant polypeptides or peptides comprising a plurality of peptide sequences derived from at least one T Cell Receptor constant domain, the recombinant polypeptide or peptide comprising a plurality of MHC-II binding motifs. According to still additional preferred embodiments the present invention provides recombinant polypeptides or peptides comprising a plurality of peptide sequences derived from a plurality of T Cell Receptor constant domains, the recombinant polypeptide or peptide comprising a plurality of MHC-II binding motifs.

Most preferably, the peptides of the present invention are derived from the constant domain of a human T cell receptor.

According to preferred embodiments, the chain is selected from the group consisting of T-cell receptor alpha chains, T-cell receptor beta-1 chains, T-cell receptor beta-2 chains, T-cell receptor gamma-1 chains, T-cell receptor gamma-2 chains and T-cell receptor delta chains. The amino acid sequences of the constant domain of human TCR chains are presented in Table 10 below, and are denoted by SEQ ID NOS:168-175. It should be understood that the present invention further encompasses peptides derived from natural allelic variants of these sequences.

According to one embodiment, the chain is selected from the group consisting of T-cell receptor alpha chains. According to particular embodiments, the chain is the T-cell receptor alpha chain and the peptide is selected from the group consisting of the peptides having the sequence set forth in any one of SEQ ID NOS: 1-27 and analogs, derivatives and salts thereof. in other particular embodiments, the peptide is selected from the group consisting of the peptides having the sequence set forth in any one of SEQ ID NOS: 1-12 and 15-27 and analogs, derivatives and salts thereof.

According to one embodiment, the chain is selected from the group consisting of T-cell receptor beta chains.

According to particular embodiments, the chain is the T-cell receptor beta-1 chain and the peptide is selected from the group consisting of the peptides having the sequence set forth in any one of SEQ ID NOS: 28-60 and analogs, derivatives and salts thereof.

According to particular embodiments, the chain is the T-cell receptor beta-2 chain and the peptide is selected from the group consisting of the peptides having the sequence set forth in any one of SEQ ID NOS:31-49, SEQ ID NOS:51-59, and SEQ ID NOS:61-64 and analogs, derivatives and salts thereof.

According to one embodiment, the chain is selected from the group consisting of T-cell receptor gamma chains and T-cell receptor delta chains.

According to particular embodiments, the chain is the T-cell receptor delta chain and the peptide is selected from the group consisting of the peptides having the sequence set forth in any one of SEQ ID NOS:65-92 and analogs, derivatives and salts thereof.

According to particular embodiments, the chain is the T-cell receptor gamma chain (accession no: A26659) and the peptide is selected from the group consisting of the peptides denoted by SEQ ID NOS:93-130 and analogs, derivatives and salts thereof.

According to particular embodiments, the chain is the T-cell receptor gamma chain (accession no: AAB63314) and the peptide is selected from the group consisting of the peptides denoted by SEQ ID NOS:93-131 and analogs, derivatives and salts thereof.

According to particular embodiments, the chain is the T-cell receptor gamma chain (accession no: AAB63312) and the peptide is selected from the group consisting of the peptides denoted by peptides denoted by SEQ ID NOS:93-100, SEQ ID NOS: 104-105, SEQ ID NOS: 107-109, SEQ ID NOS:112-125, SEQ ID NOS: 127-129, SEQ ID NOS: 131-140, and analogs, derivatives and salts thereof.

According to particular embodiments, the chain is the T-cell receptor gamma chain (accession no: AAB63313) and the peptide is selected from the group consisting of the peptides having the sequence set forth in any one of SEQ ID NOS:94-100, SEQ ID NOS: 104-105, SEQ ID NOS:107-109, SEQ ID NOS:112-130, SEQ ID NOS:133-146 and analogs, derivatives and salts thereof.

T Cell Mediated Pathologies

In one aspect, the present invention provides compositions and methods for treating or preventing T cell-mediated inflammatory diseases. "T cell-mediated inflammatory diseases" refer to any condition in which an inappropriate or detrimental T cell response is a component of the etiology or pathology of the disease or disorder. This includes both diseases and conditions directly mediated by T cells, and also diseases and conditions in which an inappropriate T cell response contributes to the production of abnormal antibodies (e.g. autoimmune or allergic diseases associated with production of pathological IgG, IgA or IgE antibodies), as well as graft rejection.

According to various embodiments, the T cell mediated inflammatory disease includes, but is not limited to, autoimmune diseases, allergic diseases, Th1 mediated diseases and other inflammatory diseases. In one embodiment of the invention, the compositions and methods of the invention are useful for treating a T cell-mediated autoimmune disease, including but not limited to: multiple sclerosis, rheumatoid arthritis, juvenile rheumatoid arthritis, autoimmune neuritis, systemic lupus erythematosus, psoriasis, Type I diabetes, Sjogren's disease, thyroid disease, myasthenia gravis, sarcoidosis, autoimmune uveitis, inflammatory bowel disease (Crohn's and ulcerative colitis) and autoimmune hepatitis. In one particular embodiment, the autoimmune disease is rheumatoid arthritis. In other particular embodiments the compositions and methods of the invention are useful for treating a Th1-associated inflammatory disease, e.g. Th1 mediated allergic responses which result in skin sensitivity and inflammation, such as contact dermatitis. In other particular embodiments the compositions and methods of the invention are useful for treating a Th2-associated inflammatory disease, lupus and allergies. In other embodiments, the compositions and methods of the invention are useful in treating a wide range of inflammatory diseases and conditions including but not limited to inflammatory or allergic diseases such as asthma (particularly allergic asthma), hypersensitivity lung diseases, hypersensitivity pneumonitis, delayed-type hypersensitivity, interstitial lung disease (ILD) (e.g., idiopathic pulmonary fibrosis, or ILD associated with rheumatoid arthritis or other inflammatory diseases). In other embodiments, the T cell mediated pathology is graft rejection, including allograft rejection and graft-versus-host disease (GVHD). Allograft rejection, e.g. organ rejection, occurs by host immune cell destruction of the transplanted tissue through an immune response. Similarly, an immune response is also involved in GVHD, but, in this case, the foreign transplanted immune cells destroy the host tissues.

Protein and Peptide-Based Compositions and Methods

The polypeptides and peptides of the invention may be isolated or synthesized using any recombinant or synthetic method known in the art, including, but not limited to, solid phase (e.g. Boc or f-Moc chemistry) and solution phase synthesis methods. For example, the peptides can be synthesized by a solid phase peptide synthesis method of Merrifield (1963). Alternatively, a peptide of the present invention can be synthesized using standard solution methods well known in the art (see, for example, Bodanszky, 1984) or by any other method known in the art for peptide synthesis.

The peptides of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid. Generally, any pharmaceutically acceptable salt of the peptide of the invention may be used, as long as the biological activity of the peptide with respect to T cell-mediated disease are maintained.

Functional derivatives consist of chemical modifications to amino acid side chains and/or the carboxyl and/or amino moieties of said peptides. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

The amino acid residues described herein are in the "L" isomeric form, unless otherwise indicated. However, residues in the "D" isomeric form can be substituted for any L-amino acid residue, as long as the peptide substantially retains the desired functional property.

It is to be understood by all of skill in the art that suitable analogs of these new peptides may be readily synthesized by now-standard peptide synthesis methods and apparatus. The limitation on such analogs is that they have essentially the same biological activity with respect to T-cell mediated disease. All such analogs will essentially be based on the new peptides as regards their amino acid sequence but will have one or more amino acid residues deleted, substituted or added. When amino acid residues are substituted, such conservative replacements which are envisaged are those which do not significantly alter the structure or biological activity of the peptide. For example basic amino acids will be replaced with other basic amino acids, acidic ones with acidic ones and neutral ones with neutral ones. In addition to analogs comprising conservative substitutions as detailed above, peptide analogs comprising non-conservative amino acid substitutions. The peptide analogs of the invention are characterized in that they retain the ability to bind MHC-II molecules and/or retain the ability to elicit an immune response to the constant domain of a TCR chain as measured by an increased anti-ergotypic T cell activity.

The overall length of a peptide of the invention is preferably between about 6 to 35 amino acids. It is well-established in the art that class II MHC molecules bind to peptides 12-15 amino acid residues in length, with a minimum length perhaps as short as 7-9 amino acid residues. Thus, the TCR constant domain fragments of the invention are preferably at least about 7-9 amino acids in length and comprise MHC-II binding motifs. In certain embodiments, e.g. when the peptides comprise a plurality of TCR constant domain-derived sequences, longer peptides, e.g. up to 50 amino acids in length, and isolated and recombinantly produced polypeptides are within the scope of the present invention. However, shorter peptides are preferable, in certain embodiments, for being easier to manufacture.

In another aspect, the present invention provides pharmaceutical compositions useful for vaccinating a subject in need thereof against a T cell mediated pathology.

In one embodiment, there is provided a vaccine composition comprising (a) at least one pharmaceutically acceptable carrier, adjuvant, excipient or diluent; (b) at least one immunogen selected from the group consisting of:
(i) the constant domain of a chain of a TCR,
(ii) a peptide comprising an immunogenic fragment of the constant domain of a chain of a TCR; and
(iii) analogs, derivatives and salts thereof.

According to another embodiment, the composition is a pharmaceutical composition comprising (a) a pharmaceutically acceptable carrier, adjuvant, excipient or diluent; (b) the constant domain of a chain of a T Cell Receptor, analogs, derivatives, salts or a peptide derived thereof, wherein the peptide exhibits the MHC Class II binding motif.

The term "vaccine" as used herein denotes a composition useful for stimulating a specific immune response in a vertebrate. This term explicitly includes both immunotherapeutic vaccines, i.e. a vaccine administered to treat and/or prevent further progression of the disease in a host already diagnosed with the disease, and prophylactic vaccines.

The pharmaceutical composition of the invention is administered to a subject in need of said treatment in a therapeutically effective amount. According to the present invention, a "therapeutically effective amount" is an amount that when administered to a patient is sufficient to inhibit, preferably to eradicate, or, in other embodiments, to prevent or delay the progression of a T cell mediated pathology. A "therapeutically effective amount" further refers to an amount which, when administered to a subject, results in a substantial increase in the immune response of the subject to the administered immunogen, as described herein.

According certain embodiments, the subject is selected from the group consisting of humans, dogs, cats, sheep, cattle, horses and pigs. In a preferred embodiment, the subject is human.

Pharmaceutical compositions for use in accordance with these embodiments may be formulated in conventional manner using one or more physiologically acceptable carriers or excipients (vehicles). The carrier(s) are "acceptable" in the sense of being compatible with the other ingredients of the composition and not deleterious to the recipient thereof. The vaccine composition can be optionally administered in a pharmaceutically or physiologically acceptable vehicle, such as physiological saline or ethanol polyols such as glycerol or propylene glycol.

All variant molecules of the constant domain of any chain of the T Cell Receptor are appropriate for the pharmaceutical composition.

The pharmaceutical composition is provided in solid, liquid or semi-solid form. A solid preparation may be prepared by blending the above components to provide a powdery composition. Alternatively, the pharmaceutical composition is provided as lyophilized preparation. The liquid preparation is provided preferably as aqueous solution, aqueous suspension, oil suspension or microcapsule composition. A semi-solid composition is provided preferably as hydrous or oily gel or ointment.

A solid composition may be prepared e.g. by mixing an excipient with a solution of the protein or peptide of the invention, gradually adding a small quantity of water, and kneading the mixture. After drying, preferably in vacuum, the mixture is pulverized. A liquid composition may be prepared e.g. by dissolving, suspending or emulsifying the protein or peptide of the invention in water, a buffer solution or the like. An oil suspension may be prepared by e.g. suspending or emulsifying the protein or peptide of the invention or protein in an oleaginous base, such as sesame oil, olive oil, corn oil, soybean oil, cottonseed oil, peanut oil, lanolin, petroleum jelly, paraffin, Isopar, silicone oil, fatty acids of 6 to 30 carbon atoms or the corresponding glycerol or alcohol esters. Buffers include e.g. Sorensen buffer, Clark-Lubs buffer, MacIlvaine buffer, Michaelis buffer, and Kolthoff buffer.

A composition may be prepared as a hydrous gel, e.g. for transnasal administration. A hydrous gel base is dissolved or dispersed in aqueous solution containing a buffer, and the protein or peptide of the invention, and the solution warmed or cooled to give a stable gel.

Preferably, the protein or peptide of the invention is administered through intravenous, intramuscular or subcutaneous administration. Oral administration may not be as effective, because the protein or peptide may be digested before being taken up. Of course, this consideration may apply less to a protein or peptide of the invention which is modified, e.g., by being cyclic peptide, by containing non-naturally occurring amino acids, such as D-amino acids, or other modification which enhance the resistance of the protein or peptide to biodegradation. Decomposition in the digestive tract may be lessened by use of certain compositions, for instance, by confining the protein or peptide of the invention in microcapsules such as liposomes. The pharmaceutical composition of the invention may also be administered to other mucous membranes. The pharmaceutical composition is then provided in the form of a suppository, nasal spray or sublingual tablet.

The dosage of the proteins or peptides of the present invention may depend upon the condition to be treated, the patient's age, bodyweight, and the route of administration, and will be determined by the attending physician.

In another embodiment, the proteins or peptides of the invention may be provided in a pharmaceutical composition comprising a biodegradable polymer including, but not limited to from poly-1,4-butylene succinate, poly-2,3-butylene succinate, poly-1,4-butylene fumarate and poly-2,3-butylene succinate, incorporating the protein or peptide of the invention as the pamoate, tannate, stearate or palmitate thereof. Such compositions are described e.g., in U.S. Pat. No. 5,439,688.

In another embodiment, a composition of the invention is a fat emulsion.

The fat emulsion may be prepared e.g. by adding to a fat or oil about 0.1-2.4 w/w of emulsifier such as a phospholipid, an emulsifying aid, a stabilizer, mixing mechanically, aided by heating and/or removing solvents, adding water and isotonic agent, and optionally, adjusting adding the pH agent, isotonic agent. The mixture is then homogenized. Preferably, such fat emulsions contain an electric charge adjusting agent, such as acidic phospholipids, fatty acids, bile acids, and salts thereof. Acidic phospholipids include phosphatidylserine, phosphatidylglycerol, phosphatidylinositol, and phosphatidic acid. Bile acids include deoxycholic acid, and taurocholic acid. The preparation of such pharmaceutical compositions is described in U.S. Pat. No. 5,733,877.

Pharmaceutical compositions according to the invention may optionally comprise additional adjuvants such as vegetable oils or emulsions thereof, surface active substances, e.g., hexadecylamin, octadecyl amino acid esters, octadecylamine, lysolecithin, dimethyl-dioctadecylammonium bromide, N,N-dicoctadecyl-N'—N'bis(2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; immune stimulating complexes; oil emulsions (including, but not limited to, oil-in-water emulsions having oil droplets in the submicron range, such as those disclosed by U.S. Pat. Nos. 5,961,970, 4,073,943 and 4,168,308); liposaccharides such as MPL® and mineral gels. The antigens of this invention can also be incorporated into liposomes, cochleates, biodegradable polymers such as poly-lactide, poly-glycolide and poly-lactide-co-glycolides, or ISCOMS (immunostimulating complexes), and supplementary active ingredients may also be employed. Metabolizable lipid emulsions, such as Intralipid or Lipofundin, may also be used as vehicles for the vaccination in the manner disclosed in WO 97/02016, the entire contents of which being hereby incorporated herein by reference. As these materials are known to cause a Th1 to Th2 cytokine shift, such lipid emulsions are advantageous for the purpose of the present invention. These lipid emulsions may be formulated as oil-in-water submicron emulsion, as disclosed in U.S. Pat. No. 5,961,970.

The protein and peptide antigens of the present invention can be coupled to albumin or to other carrier molecule in order to modulate or enhance the immune response, all as are well known to those of ordinary skill in the vaccine art.

In another aspect, the present invention provides a method of treating a T-cell mediated inflammatory disease, wherein said method comprises administering to an individual in need thereof a therapeutic composition comprising an immunogen of the invention, as detailed herein.

In another aspect, the present invention provides a method of preventing the development of a T-cell mediated inflammatory disease, wherein said method comprises administering to an individual in need thereof a therapeutic composition comprising an immunogen of the invention, as detailed herein.

In another aspect, the present invention provides a method of preventing or treating the development of a T-cell mediated inflammatory disease, wherein said method comprises administering to an individual in need thereof a therapeutic composition comprising the constant domain of a chain of a T Cell receptor or an active fragment thereof, as detailed herein.

It is to be understood that a method of preventing or treating the disease can also be described as a method of vaccination for said disease.

In another aspect, there is provided method of enhancing anti-ergotypic T cells activity in a subject in need thereof, the method comprising administering to the subject in need thereof a therapeutically effective amount of a vaccine composition of the invention, as detailed herein.

In another aspect, the invention is directed to the use of an immunogen selected from the group consisting of:
(i) the constant domain of a chain of a T Cell Receptor (TCR),
(ii) a peptide comprising an immunogenic fragment of the constant domain of a chain of a TCR; and
(iii) analogs, derivatives and salts thereof;
for the preparation of a vaccine. In various embodiments, the vaccine is useful for treating a T cell mediated inflammatory disease, for preventing the development of a T cell mediated inflammatory disease, and/or for enhancing anti-ergotypic T cells activity in a subject in need thereof.

In one embodiment, the peptide or protein should be administered in a medically effective amount, at least once, preferably soon after diagnosis. The protein or peptide may also be administered another two times, preferably at one and six months after the first administration, to provide a booster for the patient.

In certain embodiments, said immunogen is administering to the subject prior to appearance of disease symptoms. In other embodiments, said immunogen is administering to the subject after appearance of disease symptoms.

The vaccines can be administered to a human or animal by a variety of routes, including but not limited to parenteral, intradermal, transdermal (such as by the use of slow release polymers), intramuscular, intraperitoneal, intravenous, subcutaneous, oral and intranasal routes of administration, according to protocols well known in the art. The vaccine compositions of the invention are administered in a dose which is suitable to elicit an immune response in said subject. The particular dosage of the TCR constant domain antigen will depend upon the age, weight and medical condition of the subject to be treated, as well as on the identity of the antigen and the method of administration. Suitable doses will be readily determined by the skilled artisan. A preferred dose for human intramuscular, subcutaneous and oral vaccination is between about 50 µg to about 100 mg, preferably between about 200 µg to about 40 mg, and more preferably between about 500 µg to about 10 mg. Adjustment and manipulation of established dosage ranges used with traditional carrier antigens for adaptation to the present vaccine is well within the ability of those skilled in the art.

DNA Vaccination and Related Methods

According to the present invention it is now disclosed that it is possible to treat or prevent T cell-mediated inflammatory diseases by using DNA vaccines encoding the constant domain of a chain of a T Cell receptor, or an active fragment or homologue thereof.

The invention discloses for the first time that vaccination with a DNA vaccine comprising nucleotide encoding for the constant domain of a chain of the T Cell Receptor inhibits T-cell mediated inflammation and leads to an anti-ergotypic T cell response. Without wishing to be bound by any theory or mechanism of action, this suggests that the preventing or ameliorating of T cell-mediated autoimmune diseases by nucleic acids encoding for the constant domain of a chain of a T Cell Receptor might be related to a shift in the cytokines secreted by the responding T cells, rather than to suppression of the autoimmune T cell proliferation.

The use of DNA vaccination for the generation of cellular immune responses is particularly advantageous. It provides an effective therapeutic composition that enables the safe treatment of an animal with a potentially toxic protein. Without wishing to be bound by any theory or mechanism of action, expression of nucleic acid molecules encoding the constant domain of a chain of a T Cell Receptor or an active fragment thereof results in localized production of the constant domain of the chain of the T Cell Receptor or the active fragment thereby eliciting anti-ergotypic T cell responses with the encoded protein or active fragment as an ergotope. The therapeutic compositions of the present invention can provide long-term expression of the constant domain of the chain of the T Cell receptor or the active fragment thereof. Such long-term expression allows for the maintenance of an effective, but non-toxic, dose of the encoded protein or active fragment to treat a disease and limits the frequency of administration of the therapeutic composition needed to treat an animal. In addition, because of the lack of toxicity, therapeutic compositions of the present invention can be used in repeated treatments.

The present invention also relates to the use of a recombinant construct, said recombinant construct comprises an isolated nucleic acid sequence encoding the constant domain of a chain of a T Cell Receptor, or an active fragment thereof, in order to elicit anti-ergotypic T cells response. Such response is required for example in T cell mediated autoimmune diseases in which the balance between the anti-ergotypic T cells and the autoimmune T cells is disturbed.

The isolated nucleic acid sequence encoding the constant domain of various chains of T Cell Receptors and active fragments thereof may include DNA, RNA, or derivatives of either DNA or RNA. An isolated nucleic acid sequence encoding the constant domain of a chain of a T Cell Receptor can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologues thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional constant domain of a T Cell Receptor or active fragment thereof of the present invention.

A nucleic acid sequence homologue can be produced using a number of methods known to those skilled in the art (see, for example, Sambrook et al., Molecular Cloning: A Laboratory Manual, Cold Spring Harbor Labs Press, 1989). For example, nucleic acid sequences can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid.

One embodiment of the present invention is an isolated nucleic acid sequence that encodes at least a portion of the constant domain of a chain of a T Cell Receptor, or a homologue of the constant domain of a chain of a T Cell Receptor. As used herein, "at least a portion of the constant domain of a chain of a T Cell Receptor" refers to portions of the constant domain of α or β or γ or δ chains of T Cell Receptors capable of increasing the anti-ergotypic T cell response. In one preferred embodiment, a nucleic acid sequence of the present invention encodes an entire coding region of the constant domain of a chain of a T Cell Receptor. Alternatively, the nucleic acid sequence encodes a peptide derived from the constant domain of a chain of a T Cell Receptor that exhibits the MHC-II binding motif. As used herein, a homologue of the constant domain of a chain of the T Cell Receptor is a protein or peptide having an amino acid sequence that is sufficiently similar to a natural amino acid sequence that a nucleic acid sequence encoding the homologue encodes a protein or peptide capable of increasing the anti-ergotypic T cell response.

In a particular embodiment, the invention provides isolated and recombinant nucleic acid sequences encoding at lease one peptide having an amino acid sequence as set forth in any one of SEQ ID NOS:1-146 and 157-167, recombinant constructs comprising them and DNA vaccines thereof.

In another embodiment, the invention provides a nucleic acid sequence encoding a fusion peptide derived from the constant domain of a chain of a T Cell Receptor (TCR), the fusion peptide comprising a plurality of immunogenic determinants derived from at least one TCR constant domain. In a particular embodiment, the peptide comprises an amino acid sequence as set forth in any one of SEQ ID NOS: 157-167.

In another embodiment, the invention provides a nucleic acid sequence encoding a fusion peptide derived from the constant domain of a chain of a TCR, the fusion peptide comprising a plurality of peptide sequences derived from at least one TCR constant domain, the peptide comprising a plurality of Major Histocompatibility Complex (MHC)-II binding motifs. In particular embodiments, at least one peptide sequence derived from the at least one TCR constant domain comprises an amino acid sequence as set forth in any one of SEQ ID NOS:1-146 and analogs and derivatives thereof.

A polynucleotide or oligonucleotide sequence can be readily deduced from the genetic code of a protein or peptide; however, the degeneracy of the code must be taken into account. For example, without limitation, oligonucleotide sequences denoted by SEQ ID NOS:183-193 encode the immunogenic peptides of SEQ ID NOS:157-167 (see Table 14). However, nucleic acid sequences of the invention also include sequences, which are degenerate as a result of the genetic code, which sequences may be readily determined by those of ordinary skill in the art. Nucleic acid sequences encoding the constant domain of human TCR chains are presented in the Examples below, and are denoted by SEQ ID NOS:176-182. It should be understood that the present invention further encompasses nucleic acid sequences derived from natural allelic variants of these sequences.

The present invention includes a nucleic acid sequence of the present invention operatively linked to one or more transcription control sequences to form a recombinant molecule. The phrase "operatively linked" refers to linking a nucleic acid sequence to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, insect cells, and preferably in animal cells. More preferred transcription control sequences include, but are not limited to RSV control sequences, CMV control sequences, retroviral LTR sequences, SV-40 control sequences and β-actin control sequences as well as other sequences capable of controlling gene expression in eukaryotic cells. Additional suitable transcription control sequences include tissue-specific promoters and enhancers (e.g., T cell-specific enhancers and promoters). Transcription control sequences of the present invention can also include naturally occurring transcription control sequences naturally associated with a gene encoding a chain of the T Cell receptor or an active peptide derived thereof of the present invention.

According to still further features in the described preferred embodiments the recombinant construct is a eukaryotic expression vector.

According to still further features in the described particular embodiments the expression vector is selected from the group consisting of pcDNA3, pcDNA3.1 (+/−), pZeoSV2 (+/−), pSecTag2, pDisplay, pEF/myc/cyto, pCMV/myc/cyto, pCR3.1, pCI, pBK-RSV, pBK-CMV, pTRES and their derivatives.

According to the present invention, a host cell can be transfected in vivo (i.e., in an animal) or ex vivo (i.e., outside of an animal). Transfection of a nucleic acid molecule into a host cell can be accomplished by any method by which a nucleic acid molecule can be inserted into the cell. Transfection techniques include, but are not limited to, transfection, electroporation, microinjection, lipofection, adsorption, and protoplast fusion. Preferred methods to transfect host cells in vivo include lipofection and adsorption.

It may be appreciated by one skilled in the art that use of recombinant DNA technologies can improve expression of transfected nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, and deletion of sequences that destabilize transcripts. The activity of an expressed recombinant protein of the present invention may be improved by fragmenting, modifying, or derivatizing nucleic acid molecules encoding such a protein.

According to yet another aspect of the present invention there is provided a pharmaceutical composition suitable for effecting the DNA vaccination methods of the present invention. The composition includes a recombinant construct including an isolated nucleic acid sequence encoding a chain of the T Cell receptor, an active peptide derived thereof or an analog thereof, the nucleic acid sequence being operatively linked to one or more transcription control sequences, and a pharmaceutically acceptable carrier.

In one embodiment, there is provided a DNA vaccine composition comprising (a) at least one pharmaceutically acceptable carrier and (b) at least one recombinant construct comprising an isolated nucleic acid sequence encoding at least one immunogen selected from the group consisting of:
  (i) the constant domain of a chain of a T Cell Receptor (TCR); and
  (ii) a peptide comprising an immunogenic fragment of the constant domain of a chain of a TCR,
wherein the nucleic acid sequence is operatively linked to one or more transcription control sequences.

In another embodiment of the invention, the composition is useful for treating a T cell-mediated inflammatory disease as described hereinabove.

The DNA vaccine composition of the invention is administered to an individual in need of said treatment. According to still further features in the described preferred embodiments the individual is selected from the group consisting of humans, dogs, cats, sheep, cattle, horses and pigs.

In another embodiment of the present invention, a DNA vaccine composition further comprises a pharmaceutically acceptable carrier. With respect to DNA vaccines, a "carrier" refers to any substance suitable as a vehicle for delivering a nucleic acid sequence of the present invention to a suitable in vivo site. As such, carriers can act as a pharmaceutically acceptable excipient of a therapeutic composition containing a nucleic acid molecule of the present invention. Preferred carriers are capable of maintaining a nucleic acid molecule of the present invention in a form that, upon arrival of the nucleic acid molecule to a cell, the nucleic acid molecule is capable of entering the cell and being expressed by the cell. Carriers for DNA vaccines of the present invention include: (1) excipients or formularies that transport, but do not specifically target a nucleic acid molecule to a cell (referred to herein as non-targeting carriers); and (2) excipients or formularies that deliver a nucleic acid molecule to a specific site in an animal or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols.

Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to an animal, for example, esters or partial esters of fatty acids containing from about six to about twenty-two carbon atoms. Examples of esters include, caproic, octanoic, lauric, palmitic, stearic, linoleic, linolenic, olesteric, and oleic acids. Other carriers can include metal particles (e.g., gold particles) for use with, for example, a biolistic gun through the skin. Therapeutic compositions of the present invention can be sterilized by conventional methods.

Targeting carriers are herein referred to as "delivery vehicles". Delivery vehicles of the present invention are capable of delivering a therapeutic composition of the present invention to a target site in an animal. A "target site" refers to a site in an animal to which one desires to deliver a therapeutic composition. For example, a target site can be an inflamed region which is targeted by direct injection or delivery using liposomes or other delivery vehicles. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in an animal, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a cancer cell can be introduced to the outer surface of a liposome delivery vehicle so as to target the delivery vehicle to the cancer cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

A preferred delivery vehicle of the present invention is a liposome. A liposome is capable of remaining stable in an animal for a sufficient amount of time to deliver a nucleic acid sequence of the present invention to a preferred site in the animal. A liposome of the present invention is preferably stable in the animal into which it has been administered for at least about 30 minutes, more preferably for at least about 1 hour and even more preferably for at least about 24 hours.

A liposome of the present invention comprises a lipid composition that is capable of targeting a nucleic acid molecule of the present invention to a particular, or selected, site in an animal. Preferably, the lipid composition of the liposome is capable of targeting to any organ of an animal, more preferably to the lung, liver, spleen, heart brain, lymph nodes and skin of an animal, and even more preferably to the lung of an animal.

A liposome of the present invention comprises a lipid composition that is capable of fusing with the plasma membrane of the targeted cell to deliver a nucleic acid molecule into a cell. Preferably, the transfection efficiency of a liposome of the present invention is about 0.5 microgram ($\mu$g) of DNA per 16 nanomole (nmol) of liposome delivered to about $10^6$ cells, more preferably about 1.0 $\mu$g of DNA per 16 nmol of liposome delivered to about $10^6$ cells, and even more preferably about 2.0 $\mu$g of DNA per 16 mmol of liposome delivered to about $10^6$ cells.

A preferred liposome of the present invention is between about 100 and 500 nanometers (nm), more preferably between about 150 and 450 nm and even more preferably between about 200 and 400 nm in diameter.

Suitable liposomes for use with the present invention include any liposome. Preferred liposomes of the present invention include those liposomes routinely used in, for example, gene delivery methods known to those of skill in the art. More preferred liposomes comprise liposomes having a polycationic lipid composition and/or liposomes having a cholesterol backbone conjugated to polyethylene glycol.

Complexing a liposome with a nucleic acid sequence of the present invention can be achieved using methods standard in the art. A suitable concentration of a nucleic acid molecule of the present invention to add to a liposome includes a concentration effective for delivering a sufficient amount of nucleic acid molecule to a cell such that the cell can produce sufficient quantities of a constant domain of a chain of the T Cell receptor or an active peptide derived thereof to regulate effector cell immunity in a desired manner. Preferably, from about 0.1 $\mu$g to about 10 $\mu$g of nucleic acid sequence of the present invention is combined with about 8 nmol liposomes, more preferably from about 0.5 $\mu$g to about 5 $\mu$g of nucleic acid molecule is combined with about 8 nmol liposomes, and even more preferably about 1.0 $\mu$g of nucleic acid molecule is combined with about 8 nmol liposomes.

Another preferred delivery vehicle comprises a recombinant virus particle vaccine. A recombinant virus particle vaccine of the present invention includes a therapeutic composition of the present invention, in which the recombinant molecules contained in the composition are packaged in a viral coat that allows entrance of DNA into a cell so that the DNA is expressed in the cell. A number of recombinant virus particles can be used, including, but not limited to, those based on alphaviruses, poxviruses, adenoviruses, herpesviruses, arena virus and retroviruses.

Another preferred delivery vehicle comprises a recombinant cell vaccine. Preferred recombinant cell vaccines of the present invention include cell vaccines, in which allogeneic (i.e., cells derived from a source other than a patient, but that are histiotype compatible with the patient) or autologous (i.e., cells isolated from a patient) cells are transfected with recombinant molecules contained in a therapeutic composition, irradiated and administered to a patient by, for example, intradermal, intravenous or subcutaneous injection. Therapeutic compositions to be administered by cell vaccine, include recombinant molecules of the present invention without carrier.

In order to treat an animal with disease, a DNA vaccine composition of the present invention is administered to the animal in an effective manner such that the composition is capable of treating that animal from disease. For example, a recombinant molecule, when administered to an animal in an effective manner, is able to stimulate effector cell immunity in a manner that is sufficient to alleviate the disease afflicting the animal. According to the present invention, treatment of a disease refers to alleviating a disease and/or preventing the development of a secondary disease resulting from the occurrence of a primary disease. An effective administration protocol (i.e., administering a DNA vaccine composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease. In particular, the effectiveness of dose parameters and modes of administration of a therapeutic composition of the present invention when treating inflammatory diseases can be determined by assessing response rates. Such response rates refer to the percentage of treated patients in a population of patients that respond with either partial or complete remission.

In accordance with the present invention, a suitable single dose size is a dose that is capable of treating an animal with disease when administered one or more times over a suitable time period. Doses can vary depending upon the disease being treated. Doses of a therapeutic composition of the present invention suitable for use with direct injection techniques can be used by one of skill in the art to determine appropriate single dose sizes for systemic administration based on the size of an animal. A suitable single dose of a therapeutic composition to treat an inflammatory disease is a sufficient amount of sequence encoding an immunogen of the invention to reduce, and preferably eliminate, the T-cell mediated inflammatory disease following transfection of the recombinant molecules into cells. A preferred single dose of a recombinant molecule encoding an immunogen of the invention is an amount that, when transfected into a target cell population leads to the production of from about 250 femtograms (fg) to about 1 µg, preferably from about 500 fg to about 500 picogram (pg), and more preferably from about 1 pg to about 100 pg of "a constant domain of a chain of the T Cell receptor or an active peptide derived thereof" per transfected cell.

A preferred single dose of a recombinant molecule encoding an immunogen of the invention complexed with liposomes, is from about 100 µg of total DNA per 800 nmol of liposome to about 2 mg of total recombinant molecules per 16 micromole (µmol) of liposome, more preferably from about 150 µg per 1.2 µmol of liposome to about 1 mg of total recombinant molecules per 8 µmol of liposome, and even more preferably from about 200 µg per 2 µmol of liposome to about 400 µg of total recombinant molecules per 3.2 µmol of liposome.

A preferred single dose of a recombinant molecule encoding an immunogen of the invention in a non-targeting carrier to administer to an animal, is from about 12.5 µg to about 20 mg of total recombinant molecules per kg body weight, more preferably from about 25 µg to about 10 mg of total recombinant molecules per kg body weight, and even more preferably from about 125 µg to about 2 mg of total recombinant molecules per kg body weight.

It will be obvious to one of skill in the art that the number of doses administered to an animal is dependent upon the extent of the disease and the response of an individual patient to the treatment. Thus, it is within the scope of the present invention that a suitable number of doses includes any number required to cause regression of a disease. A preferred protocol is monthly administrations of single doses (as described above) for up to about 1 year. A preferred number of doses of a therapeutic composition comprising a recombinant molecule encoding an immunogen of the invention in a non-targeting carrier or complexed with liposomes is from about 1 to about 10 administrations per patient, preferably from about 2 to about 8 administrations per patient, and even more preferably from about 3 to about 5 administrations per person. Preferably, such administrations are given once every 2 weeks until signs of remission appear, then once a month until the disease is gone.

A DNA vaccine composition is administered to an animal in a fashion to enable expression of the administered recombinant molecule of the present invention into a curative protein in the animal to be treated for disease. A DNA vaccine composition can be administered to an animal in a variety of methods including, but not limited to, local administration of the composition into a site in an animal, and systemic administration.

DNA vaccine compositions to be delivered by local administration include: (a) recombinant molecules of the present invention in a non-targeting carrier (e.g., as "naked" DNA molecules, such as is taught, for example in Wolff et al., 1990, Science 247, 1465-1468); and (b) recombinant molecules of the present invention complexed to a delivery vehicle of the present invention. Suitable delivery vehicles for local administration comprise liposomes. Delivery vehicles for local administration can further comprise ligands for targeting the vehicle to a particular site.

DNA vaccine compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site. Systemic administration is particularly advantageous when organs, in particular difficult to reach organs (e.g., heart, spleen, lung or liver) are the targeted sites of treatment.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189: 11277-11281, 1992, which is incorporated herein by reference in its entirety). Oral delivery can be performed by complexing a DNA vaccine composition of the present invention to a carrier capable of withstanding degradation by digestive enzymes in the gut of an animal. Examples of such carriers, include plastic capsules or tablets, such as those known in the art. Topical delivery can be performed by mixing a therapeutic composition of the present invention with a lipophilic reagent (e.g., DMSO) that is capable of passing into the skin.

Yet another embodiment of the present invention is a method to suppress T cell activity in an animal, the method comprising administering to an animal an effective amount of a therapeutic composition comprising: (a) a naked nucleic acid molecule encoding a constant domain of a chain of the T Cell receptor or an active peptide derived thereof or an analog thereof; and (b) a pharmaceutically acceptable carrier, in which the nucleic acid molecule is operatively linked to a transcription control sequence, and in which the therapeutic composition is targeted to a site in the animal that contains excessive T cell activity.

Suitable embodiments, single dose sizes, number of doses and modes of administration of a therapeutic composition of the present invention useful in a treatment method of the present invention are disclosed in detail herein.

A DNA vaccine composition of the present invention is also advantageous for the treatment of autoimmune diseases in that the composition suppresses the harmful stimulation of T cells by autoantigens (i.e., a "self", rather than a foreign antigen). A recombinant molecule encoding an immunogen of the invention in a DNA vaccine composition, upon transfection into a cell, produce a constant domain of a chain of the T Cell receptor or an active peptide derived thereof that reduces the harmful activity of T cells involved in an autoimmune disease. A preferred therapeutic composition for use in the treatment of autoimmune disease comprises a recombinant molecule encoding an immunogen of the invention. A more preferred therapeutic composition for use in the treatment of autoimmune disease comprises a recombinant molecule encoding an immunogen of the invention combined with a non-targeting carrier of the present invention, preferably saline or phosphate buffered saline.

Such a therapeutic composition of the present invention is particularly useful for the treatment of autoimmune diseases, including but not limited to, multiple sclerosis, systemic lupus erythematosus, myasthenia gravis, rheumatoid arthritis, insulin dependent diabetes mellitus, psoriasis, polyarthritis, immune mediated vasculitides, immune mediated glomerulonephritis, inflammatory neuropathies and sarcoidosis.

A single dose of a recombinant molecule encoding an immunogen of the invention in a non-targeting carrier to administer to an animal to treat an autoimmune disease is from about 12.5 µg to about 20 mg of total recombinant molecules per kilogram (kg) of body weight, more preferably from about 25 µg to about 10 mg of total recombinant molecules per kg of body weight, and even more preferably from about 125 µg to about 2 mg of total recombinant molecules per kg of body weight.

The number of doses of a recombinant molecule encoding an immunogen of the invention in a non-targeting carrier to be administered to an animal to treat an autoimmune disease is an injection about once every 6 months, more preferably about once every 3 months, and even more preferably about once a month.

A preferred method to administer a DNA vaccine composition of the present invention to treat an autoimmune disease is by local administration, preferably direct injection. Direct injection techniques are particularly important in the treatment of an autoimmune disease. Preferably, a DNA vaccine composition is injected directly into muscle cells in a patient, which results in prolonged expression (e.g., weeks to months) of a recombinant molecule of the present invention. Preferably, a recombinant molecule of the present invention in the form of "naked DNA" is administered by direct injection into muscle cells in a patient.

In another aspect, the invention is directed to the use of a recombinant construct comprising an isolated nucleic acid sequence encoding at least one immunogen selected from the group consisting of:
(i) the constant domain of a chain of a T Cell Receptor (TCR),
(ii) a peptide comprising an immunogenic fragment of the constant domain of a chain of a TCR; and
(iv) analogs, derivatives and salts thereof;
for the preparation of a DNA vaccine. In various embodiments, the DNA vaccine is useful for treating a T cell mediated inflammatory disease, for preventing the development of a T cell mediated inflammatory disease, and/or for enhancing anti-ergotypic T cells activity in a subject in need thereof.

T Cell Vaccines and Related Methods

Alternatively, T-cell vaccination could be used in accordance with the present invention. For that purpose, the present invention provides a method for preventing or treating a T-cell mediated inflammatory disease comprising the steps of (a) obtaining cells from an individual; (b) exposing the cells in vitro to the constant domain of a chain of a T Cell Receptor or an active fragment thereof; and (c) reintroducing the exposed cells to the individual. Not wishing to be bound by theory, in many embodiments this increases the anti-ergotypic T cell response in said individual, thereby treating or preventing the disease.

In another aspect, the invention provides a pharmaceutical composition comprising attenuated activated T cells exposed ex vivo to at least one immunogen selected from a group consisting of:
(i) the constant domain of a chain of a T Cell Receptor (TCR),
(ii) a peptide comprising an immunogenic fragment of the constant domain of a chain of a TCR; and
(iii) analogs, derivatives and salts thereof.

According to this aspect, such T cell vaccines (TCV) preferably include cell vaccines in which allogeneic (i.e., cells derived from a source other than a patient, but that are histocompatible with the patient) or autologous (i.e., cells isolated from a patient) cells are activated in vitro to induce MHC-II expression, exposed to a TCR constant domain or an immunogen derived therefrom contained in a therapeutic composition, attenuated and administered to a patient by, for example, intradermal, intravenous or subcutaneous injection. In one embodiment, the patient is human.

Suitable antigen-nonspecific agents capable of activating T cells are known in the art and include, but are not limited to, mitogens such as concanavalin A, phytohemagglutinin, and pokeweed mitogen. Additional activating agents are antibodies to T cell-surface structures, including but not limited to, antibodies to the CD3 cell-surface molecule, antibodies to the CD2 cell-surface molecule, antibodies to the CD28 cell-surface molecule, and the natural ligands of CD2 or CD28. Other activating agents include phorbol esters, such as phorbol myristate acetate, or a combination of a phorbol ester and a calcium ionophore, such as ionomycin. Also intended as T cell activating agents are antibodies to the T cell receptor chains. Upon activation by such agents, T cells up regulate various surface markers, including, but not limited to MHC-II, and may express TCR constant domain epitopes in the context of MHC-II, as disclosed herein.

The T lymphocyte activation step of the present invention may or may not include the addition of T cell growth factors or stimulatory factors, such as, for example, IL-1, IL-2 or IL-4, to the culture medium for part or all of the activation interval.

Treatment to attenuate the T lymphocytes, may include, but is not limited to, gamma- or X-irradiation, or treatment with mitomycin C, by methods well known in the art, may also be used according to the invention (Ben-Nun, et al., 1987, Holoshitz et al., 1983). In one particular embodiment, the cells are attenuated by exposure to gamma irradiation (2000-10000 rads).

In another aspect, the invention provides methods of treating or preventing a T cell mediated pathology in a subject in need thereof, comprising: (a) isolating T cells from the subject or from a donor histocompatible with said subject; (b) activating the T cells ex vivo to induce Major Histocompatibility Complex (MHC) II expression; (c) exposing said activated cells to an immunogen of the invention; (d) attenuating said T cells; and (e) introducing said cells into the subject in an amount sufficient to induce an anti-ergotypic response in said subject.

Effective amounts of cells to be introduced into the subject may be extrapolated from animal model test bioassays or systems. Suitable amounts of attenuated TCR constant domain-derived peptide-loaded T cells are preferably between $10^6$-$10^8$ cells per administration.

In other embodiments, other suitable attenuated antigen presenting cells (APC) may be exposed to a peptide of the invention and administered to the subject. Such APC are capable of presenting a peptide of the invention in the form of antigen-MHC class II complex, in a manner recognizable by specific effector cells of the immune system and thereby inducing an effective cellular immune response against the antigen being presented. Suitable cell populations may be e.g. peripheral blood mononuclear cells and APC purified therefrom such as macrophages, B-cells and dendritic cells In other aspects, the invention provides T cell vaccine compositions and methods thereof using adoptive transfer of anti-ergotypic cells specific for a TCR constant domain-derived peptide.

The generation of antigen-specific cell lines is within the abilities of those of skill in the art, and is currently being applied for the development of therapeutic TCV (see, for example, Achiron et al., 2004). For the generation of anti-ergotypic cells specific for an immunogen of the invention suitable for adoptive transfer TCV, a first population of T cells is activated by incubation in the presence of a second population of a TCR constant domain-derived peptide-loaded attenuated activated T cells, or other professional APC, as described above. Such attenuated T cells or APC may be incubated with a TCR constant domain-derived peptide prior to incubation with the first T cell population, or alternatively be incubated with the first T cell population in the presence of the TCR constant domain-derived peptide. Anti-ergotypic T cells specific for the TCR constant domain-derived peptide present in the first population recognize TCR constant domain epitopes presented on MHC-II molecules of the second population. It is to be understood, therefore, that both cell populations used are histiotype compatible (histocompatible) with each other as well as with the subject in need of said treatment. Advantageously, this activation step is repeated at least once (and is typically performed 2-3 times), in order to enrich the resulting T cell population for the desired peptide-specific anti-ergotypic T cells. The method may optionally further comprise one or more steps of expanding the resulting peptide-specific anti-ergotypic-enriched T cell population, e.g. by culturing in the presence of IL-2. The resulting T cell population is then administered to said subject in an amount sufficient to induce an anti-ergotypic response in said subject. Suitable amounts of anti-ergotypic-enriched T cells specific for the TCR constant domain-derived peptide are preferably between $10^7$-$3\times10^7$ cells per administration.

Diagnostic Compositions And Methods

In other embodiments, the novel peptides of the invention are useful for diagnosing conditions associated with an immune response to these peptides. Thus, the invention provides diagnostic methods effected by determining the capacity of immunoglobulins of a subject to specifically bind an antigen probe comprising a peptide of the invention, where such capacity is indicative of the condition, and compositions and kits useful in these methods.

In one embodiment, there is provided a method of diagnosing a condition associated with an immune response in a subject in need thereof, the method comprising:
 d) obtaining an antibody-containing biological sample from a subject;
 e) contacting the sample, under conditions such that an antigen-antibody complex may be formed, with an antigen probe comprising a peptide having an amino acid sequence as set forth in any one of SEQ ID NOS:1-146 and 157-167, and analogs, derivatives and salts thereof;
 f) determining the capacity of at least one antibody obtained from the subject to specifically bind the antigen probe;
 wherein the capacity is indicative of the condition.

In another embodiment, detection of the capacity of an antibody to specifically bind an antigen probe may be performed by quantifying specific antigen-antibody complex formation. The term "specifically bind" as used herein means that the binding of an antibody to an antigen probe is not competitively inhibited by the presence of non-related molecules.

In certain embodiments, said condition is associated with an increased T cell-mediated response. In certain particular embodiments, said condition is associated with an increased T cell activity. In various embodiments, the increased T cell-mediated immune response may be a detrimental immune response, or, in alternate embodiments, a protective immune response. In another embodiment, said condition is a T cell mediated inflammatory disease. In another particular embodiment, said condition is associated with an increased anti-ergotypic T cell activity.

Preferably the method of the present invention is performed by determining the capacity of a peptide of the invention to specifically bind antibodies of the IgG isotype isolated from a subject.

Methods for obtaining suitable antibody-containing biological samples from a subject are well within the ability of those of skill in the art. Typically, suitable samples comprise whole blood and products derived therefrom, such as plasma and serum. In other embodiments, other antibody-containing samples may be used, e.g. urine and saliva samples. A non-limitative example for obtaining human serum samples is presented in Example 12 below.

In certain embodiments, the peptides and peptide compositions prepared in accordance with the present invention can be used to diagnose a T cell mediated pathology by using them as the test reagent in an enzyme-linked immunoadsorbent assay (ELISA), an enzyme immunodot assay, a passive hemagglutination assay (e.g., PHA test), an antibody-peptide-antibody sandwich assay, a peptide-antibody-peptide sandwich assay, or other well-known immunoassays. In accordance with the present invention, any suitable immunoassay can be used with the subject peptides. Such techniques are well known to the ordinarily skilled artisan and have been described in many standard immunology manuals and texts. In one particular embodiment, the immunoassay is an ELISA using a solid phase coated with the peptide compositions of the present invention. For example, such a kit may contain a solid-phase immobilized peptide of the invention and a tagged antibody capable of recognizing the non-variable region of the antibody to be detected, such as tagged anti-human Fab. The kit may also contain directions for using the kit and containers to hold the materials of the kit. Any conventional tag or label may be used, such as a radioisotope, an enzyme, a chromophore or a fluorophore. A typical radioisotope is iodine-125 or sulfur-35. Typical enzymes for this purpose include horseradish peroxidase, horseradish galactosidase and alkaline phosphatase.

In certain embodiments, the antigen probe comprises a plurality of antigen probes comprising at least one peptide of the invention.

In certain preferable embodiments, determining the capacity of the antibodies to specifically bind the antigen probes is performed using an antigen probe array-based method. Preferably, the array is incubated with suitably diluted serum of the subject so as to allow specific binding between antibodies contained in the serum and the immobilized antigen probes, washing out unbound serum from the array, incubating the washed array with a detectable label-conjugated ligand of antibodies of the desired isotype, washing out unbound label from the array, and measuring levels of the label bound to each antigen probe. Ample guidance for practicing array-based methods of determining the capacity of antibodies of a subject to specifically bind to antigens such as the antigen probes of the present invention is provided in the Examples section which follows and in the literature of the art. A non-limitative example of using an antigen array-based method in the diagnosis of lung cancer is provided in Example 12 hereinbelow.

Various methods have been developed for preparing arrays suitable for the methods of the present invention. State-of-the-art methods involves using a robotic apparatus to apply or "spot" distinct solutions containing antigen probes to closely spaced specific addressable locations on the surface of a planar support, typically a glass support, such as a microscope slide, which is subsequently processed by suitable thermal and/or chemical treatment to attach antigen probes to the surface of the support. Suitable supports may also include silicon, nitrocellulose, paper, cellulosic supports and the like.

Preferably, each antigen probe, or distinct subset of antigen probes of the present invention, which is attached to a specific addressable location of the array is attached independently to at least two, more preferably to at least three separate specific addressable locations of the array in order to enable generation of statistically robust data.

In addition to antigen probes of the invention, the array may advantageously include control antigen probes. Such control antigen probes may include normalization control probes. The signals obtained from the normalization control probes provide a control for variations in binding conditions, label intensity, "reading" efficiency and other factors that may cause the signal of a given binding antibody-probe ligand interaction to vary. For example, signals, such as fluorescence intensity, read from all other antigen probes of the antigen probe array are divided by the signal (e.g., fluorescence intensity) from the normalization control probes thereby normalizing the measurements. Normalization control probes can be bound to various addressable locations the antigen probe array to control for spatial variation in antibody-ligand probe efficiency. Preferably, normalization control probes are located at the corners or edges of the array to control for edge effects, as well as in the middle of the array.

The labeled antibody ligands may be of any of various suitable types of antibody ligand. Preferably, the antibody ligand is an antibody which is capable of specifically binding the Fc portion of the antibodies of the subject used. For example, where the antibodies of the subject are of the IgG isotype, the antibody ligand is preferably an antibody capable of specifically binding to the Fc region of IgG antibodies of the subject.

The ligand of the antibodies of the subject may be conjugated to any of various types of detectable labels. Preferably the label is a fluorophore, most preferably Cy3. Alternately, the fluorophore may be any of various fluorophores, including Cy5, fluorescein isothiocyanate (FITC), phycoerythrin (PE), rhodamine, Texas red, and the like. Suitable fluorophore-conjugated antibodies specific for antibodies of a specific isotype are widely available from commercial suppliers and methods of their production are well established.

Antibodies of the subject may be isolated for analysis of their antigen probe binding capacity in any of various ways, depending on the application and purpose. While the subject's antibodies may be suitably and conveniently in the form of serum or a dilution thereof, the antibodies may be subjected to any desired degree of purification prior to being tested for their capacity to specifically bind antigen probes. The method of the present invention may be practiced using whole antibodies of the subject, or antibody fragments of the subject which comprises an antibody variable region.

Having now generally described the invention, the same will be more readily understood through reference to the following examples, which are provided by way of illustration and are not intended to be limiting of the present invention.

EXAMPLES

As used herein, the terms "pβC1" and "pβC2" refer to coding sequences of the C1 and the C2 variant molecules of the β chain of the constant domain of the T-cell receptor (TCR-C). As used herein, the terms "recombinant βC1" or "rβC1" and "recombinant βC2" or "rβC2" refer to recombinant C1 and the C2 variant molecules of the β chain of the constant domain of the T-cell receptor (TCR-C). βC1/2 peptides are peptides derived from the C1 or the C2 variant molecules of the β chain of the constant domain of the T-cell receptor (TCR).

Animals

Female Lewis rats were raised and maintained under pathogen-free conditions in the Animal Breeding Center of The Weizmann Institute of Science. One- to two-month old rats were used for vaccination experiments. The experiments were performed under the supervision and guidelines of the Animal Welfare Committee.

Antigens and Adjuvants

Peptides were synthesized as previously described (Quintana et al 2002). The HSP65 Mt176-190 peptide used was EESNTFGLQLELTEG (SEQ ID NO:155).

C1 and C2 peptides: see Table 1.

Purified recombinant HSP65 was generously provided by Prof. Ruurd van der Zee (Institute of Infectious Diseases and Immunology, Faculty of Veterinary Medicine, Utrecht, The Netherlands).

The β chain of the C1 and C2 rat molecules were subcloned from pcDNA3 into the BamHI/HindIII sites of the pQE-80L plasmid (Qiagen) for bacterial expression using standard molecular biology techniques. The C1 and C2 recombinant proteins (rβC1 and rβC2) were expressed and purified following the manufacturer's instructions.

M. tuberculosis Strain H37Ra and incomplete Freund's adjuvant (IFA) were purchased from Difco (Detroit, Mich., USA). Tuberculin purified protein derivative (PPD) was provided by the Statens Seruminstitut (Copenhagen, Denmark). Ovalbumin (OVA) and Concanavalin A (Con A) were purchased from Sigma (Rehovot, Israel).

DNA Plasmids and Vaccination

The pβC1 and pβC2 vectors were generated in the following way. The C1 or C2 regions of the β chain of the tcr gene were amplified by PCR from cDNA prepared form lymph node cells of Lewis rats using specific oligonucleotides containing restriction sites for the enzymes BamHI (oligonucleotide 5') or HindIII (oligonucleotide 3'). The amplicons were then cloned into the pcDNA3 or pQE vectors (Invitrogen, NV, Leek, The Netherlands) using standard molecular biology techniques. The plasmids were sequenced to confirm correct insertion of the cDNA and transcribed in vitro to check that they were functional.

Plasmid DNA was prepared in large scale and injected after pretreatment with cardiotoxin (Sigma, Rehovot, Israel) as previously described (Quintana et al., 2002). Briefly, rats were vaccinated in the quadriceps three times (on days −40, −26 −12 relative to AA induction) with 150 μg of pcDNA3, pβC1 or pβC2. Endotoxin levels were checked by *Limulus Amoebocyte* Lysate and found always to be under acceptable levels for in vivo use (less than 0.02 EU/μg DNA). AA was induced 12 days after the last injection of DNA. The empty vector pcDNA3 was used as a DNA vaccination control.

AA Induction and Assessment

AA was induced as described (Quintana et al 2002), using 1 mg per rat of heat-killed Mt strain H37Ra (Difco). Each experimental and control group contained at least 8 rats. The day of AA induction was designated as day 0, and disease severity was assessed by direct observation of all 4 limbs in each animal. A relative score between 0 and 4 was assigned to each limb, based on the degree of joint inflammation, redness and deformity; thus the maximum possible score for an individual animal was 16 (Quintana et al 2002). The mean AA score (±SEM) is shown for each experimental group. Arthritis was also quantified by measuring hind limb diameter with a caliper. Measurements were taken on the day of the induction of AA and 26 days later (at the peak of AA); the results are presented as the mean±SEM of the difference between the two values for all the animals in each group. The person who scored the disease was blinded to the identity of the groups. Experiments were repeated at least 3 times and produced similar results.

T-Cell Proliferation

Unless otherwise stated, T-cell proliferation assays were performed at day 26 after the induction of AA, when the disease is at its peak, as previously described (Quintana et al 2002). Briefly, popliteal and inguinal lymph node cells (LNC), were cultured in quadruplicates in 200 μl round bottom microtiter wells (Costar Corp., Cambridge, USA) at $2 \times 10^5$ cells per well with or without antigen. The T-cell mitogen Concanavalin A (Con A) was used as a positive control for T-cell proliferation. Cultures were incubated for 96 hrs at 37° C. in a humidified atmosphere of 5% $CO_2$. T-cell responses were detected by the incorporation of [methyl-3H]-thymidine (Amersham, Buckinghamshire, UK; 1 μCi/well), which was added to the wells for the last 18 hours. The stimulation index (SI) was computed as the ratio of the mean c.p.m. of antigen- or mitogen-containing wells to control wells cultured with medium alone. The results of T-cell proliferation experiments are shown as SI±SEM, T-cell responses with SI<2 were considered not significant.

For ergotypic stimulation, the Lewis rat 2 clones were used—the Lewis rat A2 T cell clone, specific for the peptide Mt176-190 and the p277 clone, specific for the peptide HSP60 residues 436-460.

Vaccination with Peptides or Recombinant Proteins
Female Lewis rats were immunized ip with a single dose of 100 μg of peptide or recombinant protein emulsified in IFA.

Adoptive Transfer of Cells

Spleen cells were prepared from peptide-vaccinated rats, either 7 days after peptide vaccination, or 26 days after AA was induced following peptide vaccination. The splenocytes ($10^7$ cells per ml) were activated with 2.5 μg/ml of Con A for 48 hr at 37° C. in a humidified atmosphere of 5% $CO_2$. The cells were washed with sterile PBS and injected iv into naïve rats ($5 \times 10^7$ cells per rat). Three days after the transfer of the splenocytes, AA was induced.

Example 1

DNA vaccination with C1 or C2 Protects from Adjuvant Arthritis

Figure 1B:
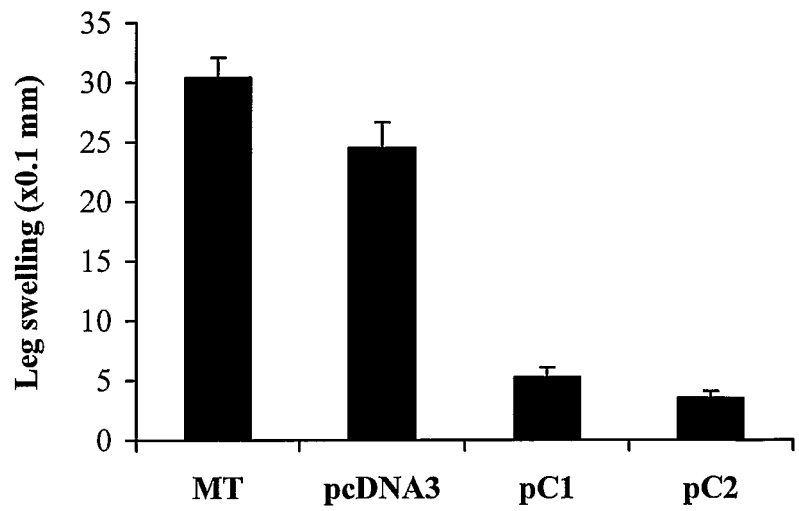

The inventors and coworkers previously demonstrated that DNA vaccination with the α chain of the IL-2 receptor (CD25) inhibited the development of AA (Mimran et al. 2004). We have now cloned the C1 and the C2 variant molecules of the β chain of the constant domain of the rat T-cell receptor (TCR) in the pCDNA3 vector, suitable for DNA vaccination studies. In this way, we generated pβC1 and pβC2 vaccination constructs. Lewis rats were vaccinated with pβC1, pβC2 or with pcDNA3 as a control, and AA was induced. FIG. 1A shows vaccination with pβC1 or pβC2 significantly (p<0.001) inhibited arthritis compared to the rats that had been vaccinated with the pcDNA3 control. The protective effect of vaccination with pβC1 or pβC2 was also reflected in a significant reduction in ankle swelling (FIG. 1B).

Example 2

Immune Responses of Rats Protected from AA by pβC1 or pβC2 Vaccination

Figure 2A:
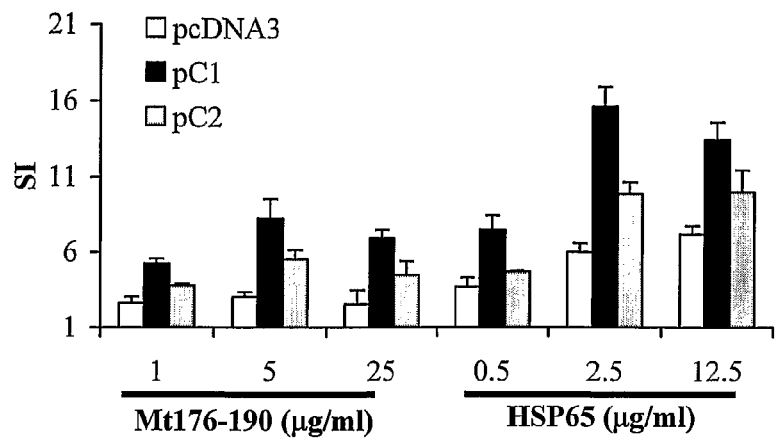
FIG. 2 illustrates T cell response after DNA vaccination. Note that in FIG. 2 pC1 denotes pβC1 and pC2 denotes pβC2.
Figure 2B:
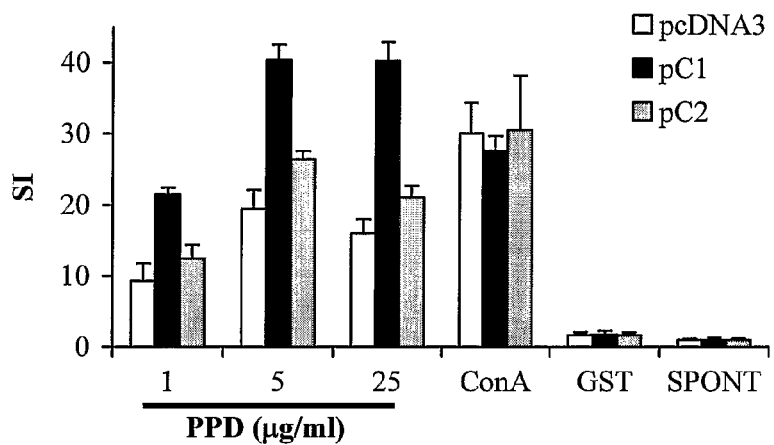
Figure 2C:
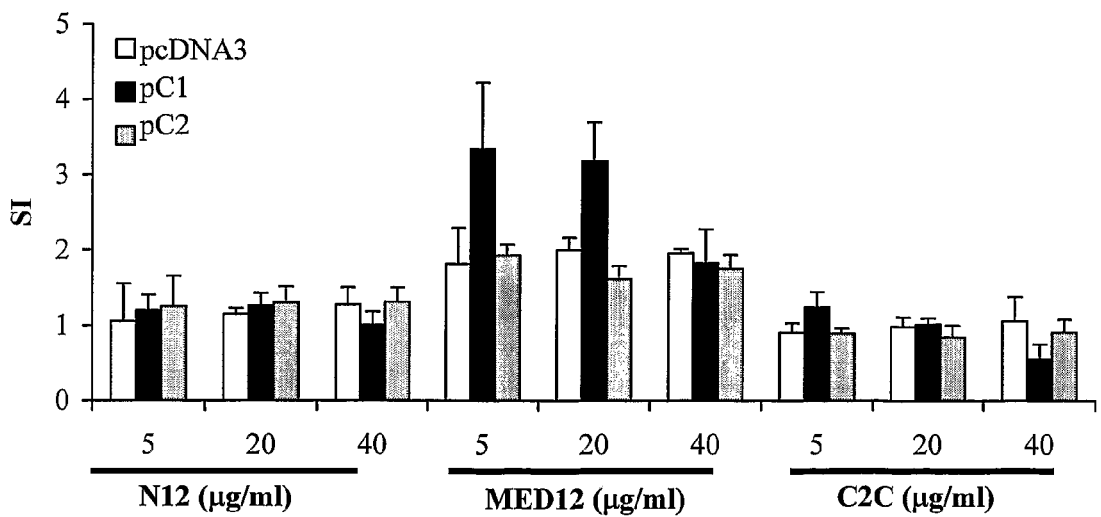

To study the immune responses associated with the inhibition of AA by DNA vaccination with pβC1 or pβC2, we analyzed the T-cell responses of immunized rats 26 days after the induction of AA. We stimulated draining lymph node cells (LNC) in vitro with a collective of Mycobacterial antigens known to be associated with AA: HSP65, PPD and Mt176-190. The Mt176-190 peptide contains the 180-188 epitope of HSP65 described by van Eden et al which is recognized by HSP65-specific T-cell clones that can transfer AA (van Eden et al 1985). We also studied the immune response directed to recombinant βC1 and recombinant βC2, or to βC1/2 peptides predicted to bind the MHC class II molecule of the Lewis rat (see Table 1). Glutathione-S-transferase (GST) was included as a control antigen. None of the experimental groups showed significant responses to GST, and they did not differ in their responses to concanavalin A (Con A) (FIG. 2B). Nevertheless, inhibition of AA by DNA vaccination with the pβC1 or pβC2 constructs was associated with the up-regulation of the T-cell proliferative responses to the panel of Mycobacterial antigens (PPD, HSP65 and Mt176-190; FIG. 2A-B). This enhancement of T-cell proliferation was also found to accompany other immune treatments that inhibited arthritis (Mimran et al 2004; Quintana et al 2002; Quintana et al 2003 Hogervorst et al 1991) In addition, FIG. 2C shows that pβC1 vaccination induced significant responses directed to the peptide of SEQ ID NO. 149 (MED12).

TABLE 1

| rat C1 and C2 sequences |
|---|
| A. Constant domains of rat TCR beta chain variants |
| C1 T-cell receptor beta chain (gi: 1332388; SEQ IT NO: 153)<br>  1 dlktvtppkv slfepseaei adkqkatlvc largffpdhv elswwvngke irngvstdpq<br> 61 aykesnnity clssrlrvsa pfwhnprnhf rcqvqfyglt eednwsedsp kpvtqnisae<br>121 awgradcrit sasyqqgvls atilyeilig klyavlvstl vvmtmvkrks s |
| C2 T-Cell receptor beta chain (gi: 1332389; SEQ ID NO: 154)<br>  1 dlktvtppkv slfepseaei tdkqkatlvc largffpdhv elswwvngke irngvstdpq<br> 61 aykesnnity clssrlrvsa pfwhnprnhf rcqvqfyglt eednwsedsp kpvtqnisae<br>121 awgradcgit sasyhqgvls atilyeillg katlyavlvs alvlmamvkk kns |

TABLE 1-continued rat C1 and C2 sequences

B. N12, MED12 and C2C peptides that were identified as MHC class II binders, based on the binding motifs described by Reizis et al.
N12 (C1) 5 vtppkvslfepseaeia 21

| | | |
|---|---|---|
| C1 | vtppkvslfepseaeia | SEQ ID NO: 147 |
| C2 | vtppkvslfepseaeit | SEQ ID NO: 148 |

MED12 (C1) 108 dspkpvtqnisaeawgr 124

| | | |
|---|---|---|
| C1 | dspkpvtqnisaeawgr | SEQ ID NO: 149 |
| C2 | dspkpvtqnisaeawgr | SEQ ID NO: 150 |

C2C(C2) 157 vlvs alvlmamvkk kns 173

| | | |
|---|---|---|
| C1 | vlvstlvvmtmvkrkss | SEQ ID NO: 151 |
| C2 | vlvsalvlmamvkkkns | SEQ ID NO: 152 |

Example 3

DNA Vaccination with pβC1 or pβC2 Activates Anti-Ergotypic Responses

Figure 3A:
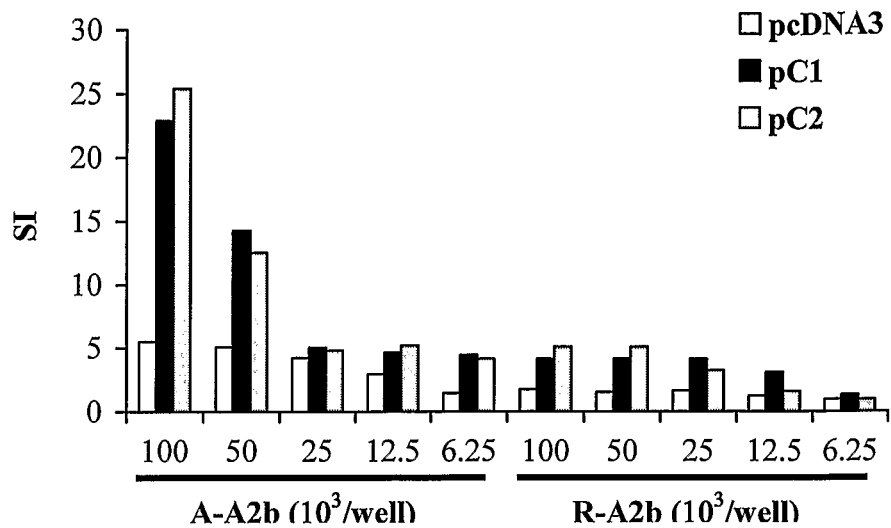
FIG. 3 illustrates anti-ergotypic responses after DNA vaccination. Note that in FIG. 3 pC1 denotes pβC1 and pC2 denotes pβC2.
Figure 3B:
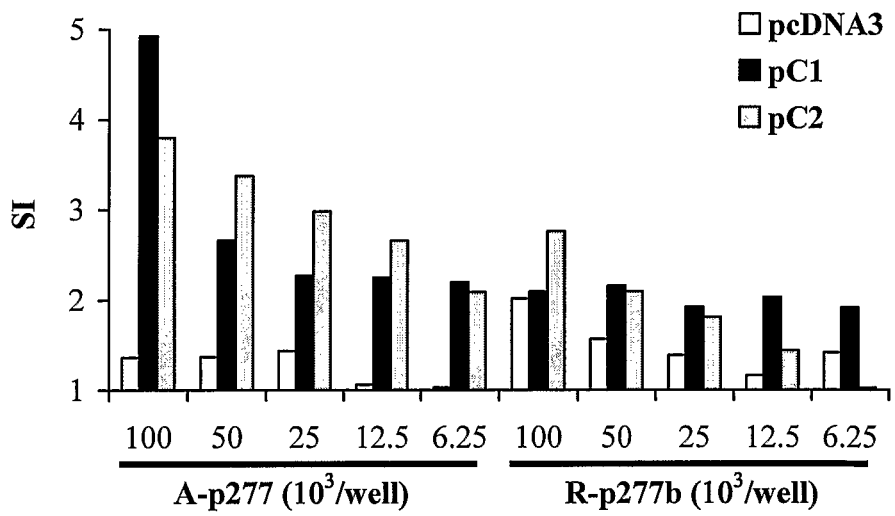

To demonstrate that vaccination with pβC1 or pβC2 induced anti-ergotypic T cells, we studied the proliferative response directed to resting or activated T cells following vaccination. FIG. 3 shows that LNC isolated from pβC1 or pβC2-vaccinated rats have strong anti-ergotypic responses. In FIG. 3A, A-A2b denotes activated A2b T cell clones, while R-A2b denotes resting A2b T cell clones. In FIG. 3B, A-p277 denotes activated p277 T cell clones, while R-p277 denotes resting p277 T cell clones. Thus, C1 or C2 ergotope determinants are generated by the processing of endogenous TCR in activated T cells but not by resting T cells.

Example 4

Vaccination with Recombinant C1, C2, or C1/2 Peptides Inhibits AA

Figure 4A:
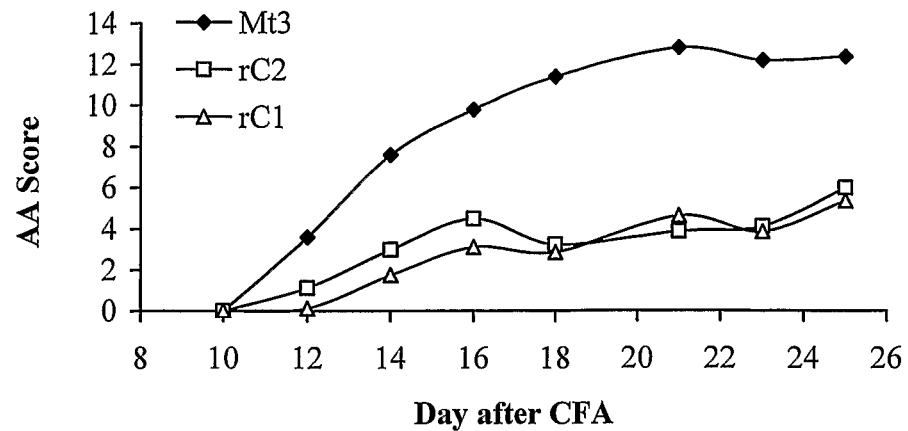
FIG. 4 illustrates inhibition of AA by vaccination with recombinant C1, C2 or C1/2 derived peptides. Note that in FIG. 4 rC1 denotes rβC1 and rC2 denotes rβC2.
Figure 4B:
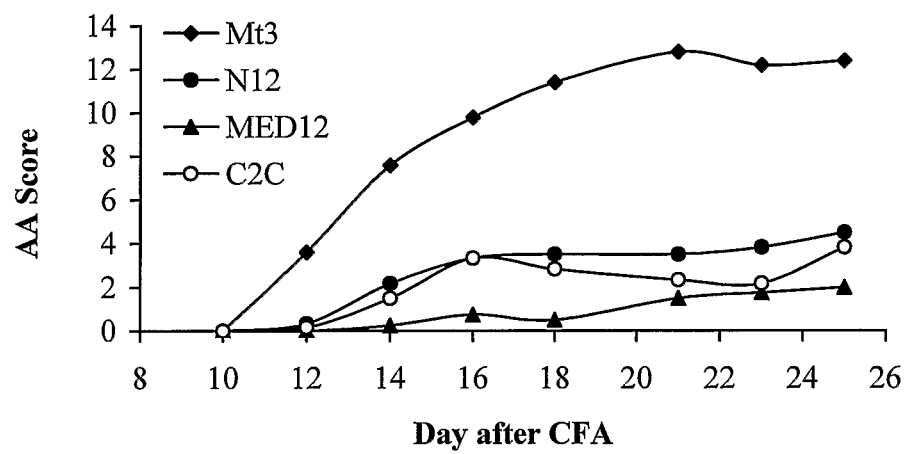

We studied the immune effects of vaccination with recombinant C1 (rβC1) or C2 (rβC2), or with C1/2-derived peptides (Table 1). Female Lewis rats were immunized with a single ip dose of 100 μg of protein or peptide in IFA, and seven days later AA was induced. FIG. 4 shows that the severity of the disease was significantly decreased in rats vaccinated with rβC1, rβC2 (FIG. 4A) or with any of the βC1/2 peptides N12 (SEQ ID NO:147), MED12 (SEQ ID NO:149) or C2C (SEQ ID NO:152) (FIG. 4B). Therefore, vaccination with rβC1, rβC2 or βC1/2 peptides can specifically inhibit AA.

Example 5

Immune Responses in Vaccinated Rats

Figure 5A:
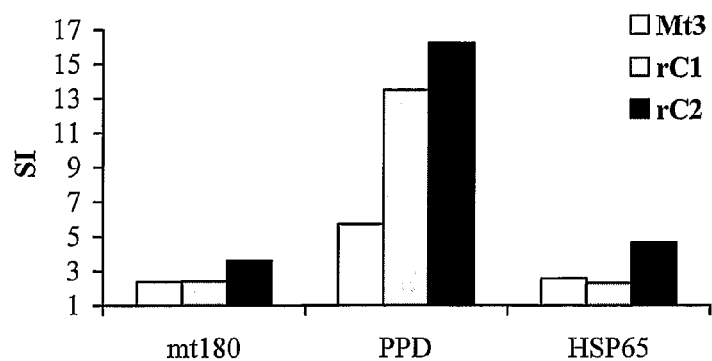
FIG. 5 illustrates T cell responses to C1/2 peptides after vaccination with rβC1 or rβC2. Note that in FIG. 5 rC1 denotes rβC1 and rC2 denotes rβC2, and Mt180 denotes Mt176-190.
Figure 5B:
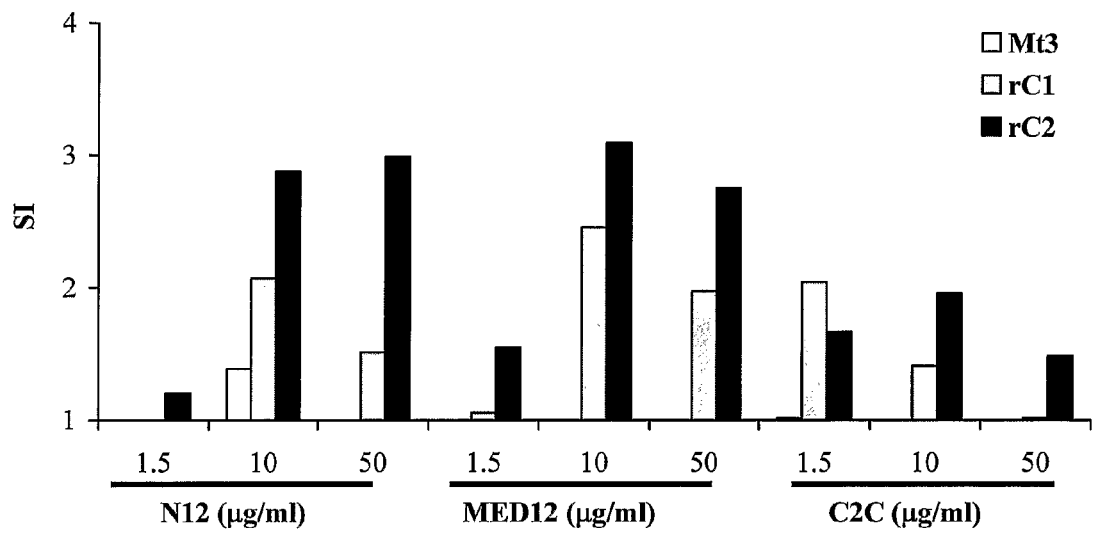

To study the effect of C1/2 vaccination on the immune response to C1/2 peptides and to the target antigens of AA, we vaccinated rats with rβC1 or rβC2, and then induced AA. At day 26, we removed the draining lymph nodes and measured the T-cell proliferative responses to peptides N12 (SEQ ID NO:147), MED12 (SEQ ID NO:149) or C2C (SEQ ID NO:152), or to the Mycobacterial antigens. FIG. 5A shows that vaccination with whole rβC1 or rβC2 induced a proliferative response to the TCR-C peptides; there was no response to the control peptide Mt3. Thus the C1/2 peptides are immunologically dominant. Moreover, vaccination using rβC1 or rβC2, like DNA vaccination with pβC1 or pβC2 (see FIG. 2), also up-regulated the proliferative responses to Mycobacterial antigens (FIG. 5B), which is associated with inhibition of the arthritis (Mimran et al 2004; Quintana et al 2002; Quintana et al 2003; Hogervorst et al 1991).

Example 6

C1/2 Peptides are Immunogenic

Figure 6A:
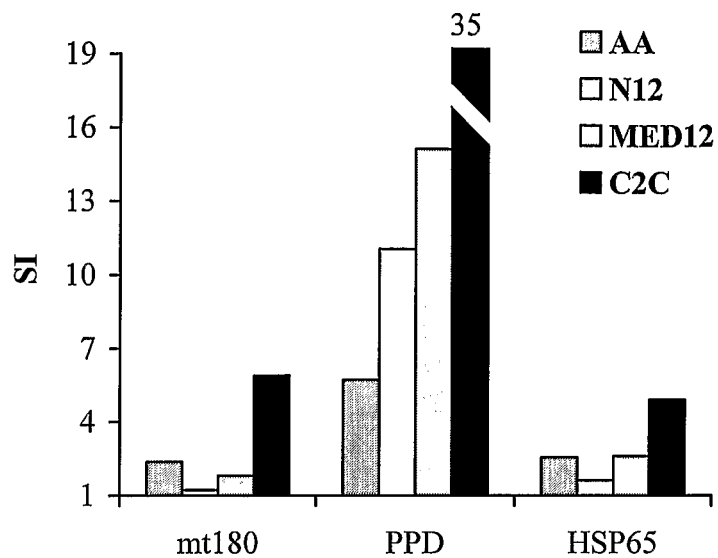
FIG. 6 illustrates T cell responses after vaccination with rβC1 or rβC2. Note that in FIG. 6 Mt180 denotes Mt176-190.
Figure 6B:
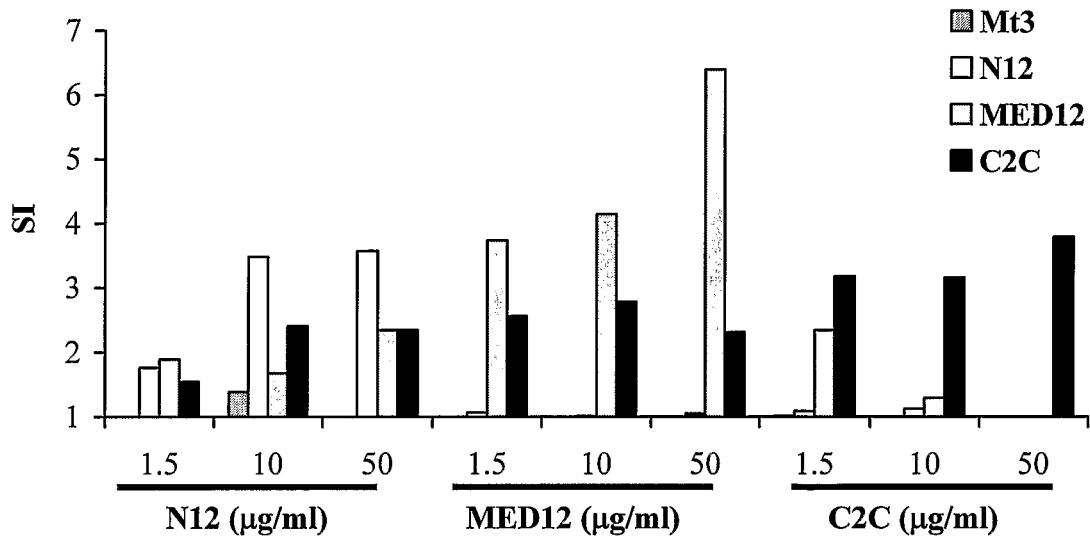

Study of the T-cell responses in rats that had been vaccinated with the C1/2 peptides N12, MED12 or C2C revealed that the three peptides were immunogenic; significant T-cell responses could be detected in the immunized rats to each peptide (FIG. 6B). In addition, LNC taken from peptide immunized rats showed increased proliferative responses to PPD. LNC from C2C-vaccinated rats also showed increased proliferative responses to mt180 and HSP65 (FIG. 6A). None of the experimental groups showed significant responses to OVA, and they did not differ in their response to Con A.

Example 7

Adoptive Transfer of Vaccination-Induced Regulation

Figure 7A:
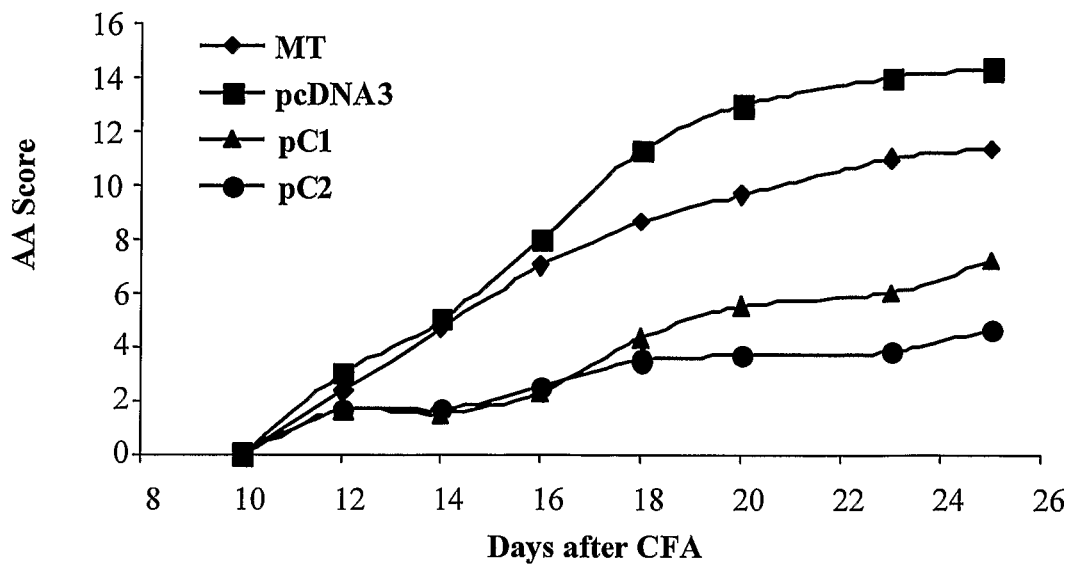
FIG. 7 illustrates inhibition of AA by transfer of Con A-activated splenocytes from pC1 or pC2 vaccinated rates. Note that in FIG. 7 pC1 denotes pβC1 and pC2 denotes pβC2.
Figure 7B:
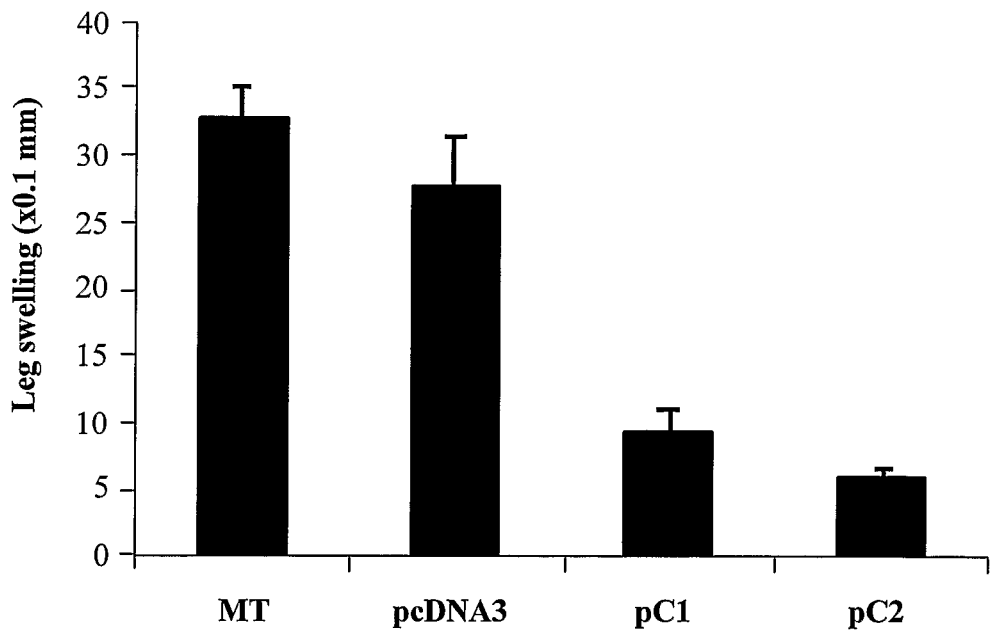
Figure 8A:
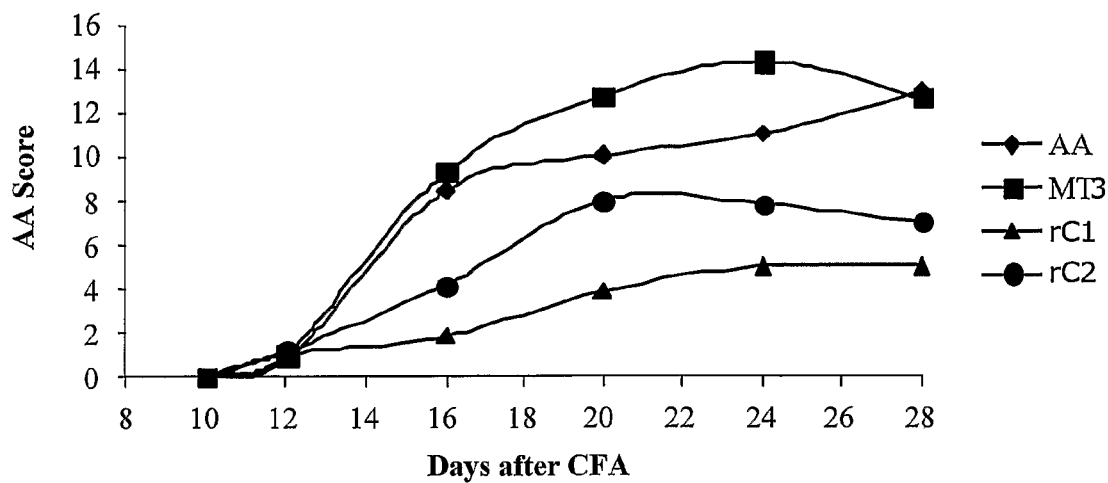
FIG. 8 illustrates inhibition of AA by transfer of Con A-activated splenocytes from rC1 or rC2 vaccinated rates. Note that in FIG. 8 rC1 denotes rβC1 and rC2 denotes rβC2.
Figure 8B:
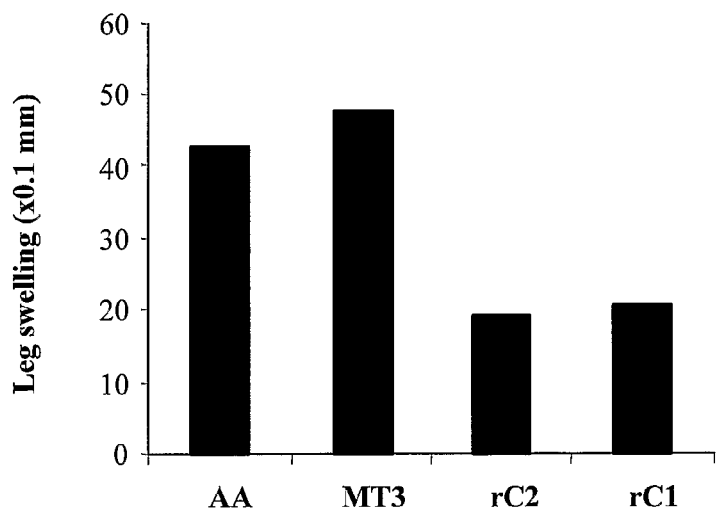

To learn whether the inhibition of AA triggered by vaccination with C1 or C2, either as DNA vaccines or recombinant proteins could be adoptively transferred by activated T-cells, we vaccinated rats with pβC1, pβC2 (FIG. 7), rβC1 or rβC2 (FIG. 8), induced AA, and obtained splenocytes for adaptive transfer 26 days after the induction of AA. The splenocytes were activated in vitro with Con A and transferred into naïve rats, and the rats were challenged three days later with Mt and followed for the development of AA. Inhibition of AA by vaccination with C1 or C2 could be adoptively transferred by activated T-cells, as reflected in disease severity (FIGS. 7A and 8A) and ankle swelling (FIGS. 7B and 8B).

Example 8

T-cell Lines to C1/2 Determinants

To further study the specificity of the C1/2 determinants involved in the protection triggered by vaccination with C1 or C2, we raised T cell lines against the N12, MED12 and C2C peptides that were identified as MHC class II binders, based on the binding motifs described by Reizis et al.

Figure 9A:
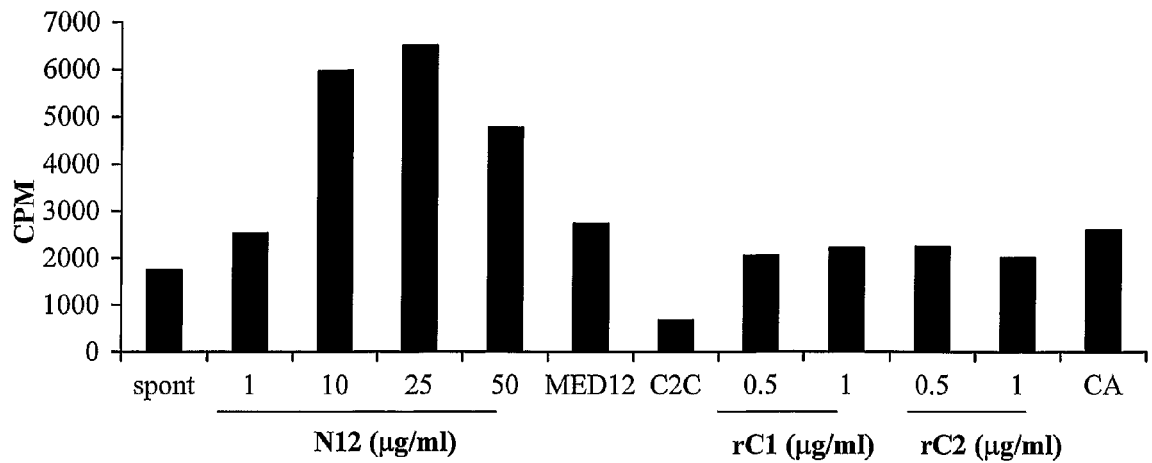
FIG. 9 illustrates proliferative response of T-cell lines to C1/2 determinants. Note that in panel 1 of FIG. 9 MED12 and C2C are at a concentration of 10 µg/ml. Note that in FIG. 9 rC1 denotes rβC1 and rC2 denotes rβC2.
Figure 9B:
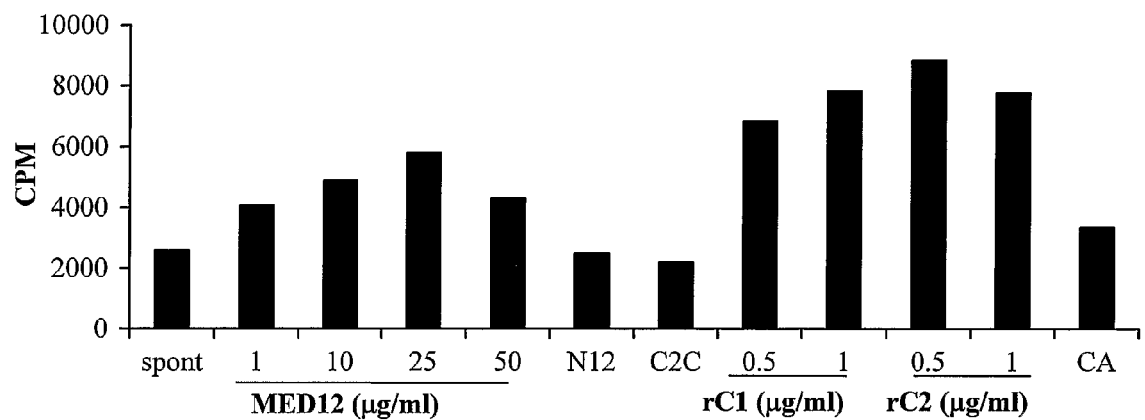
Figure 9C:
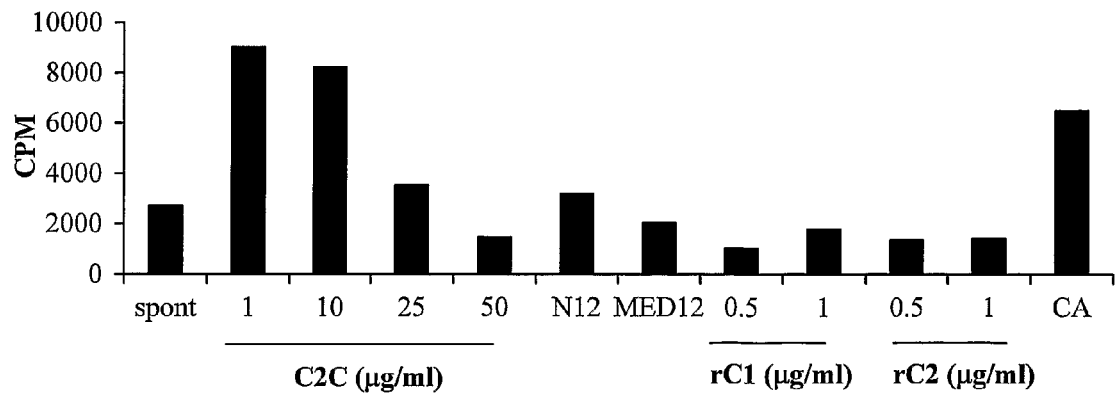

Female Lewis rats were immunized with a single ip dose of 100 μg of peptide in IFA, and seven days later AA was induced. At day 26, LNC were prepared and specific T cell lines were generated by repeated stimulation with peptides N12, MED12 or C2C, as described by Mor et al. FIG. 9 shows that, following 3 cycles of stimulation, we obtained peptide-specific lines: N12-specific (FIG. 9A), MED12-specific (FIG. 9B) and C2C-specific (FIG. 9C). Each line reacted with the peptide against which it was raised and showed no cross-reactivity with the other C1/2-derived peptides. In addition, only the line raised against MED12 could be activated by APC fed with rβC1 or rβC2, suggesting that the epitope contained in MED12 can be generated after processing of the full-length molecule.

Example 9

T-cell Lines to C1/2 Determinants Inhibit AA

Figure 10A:
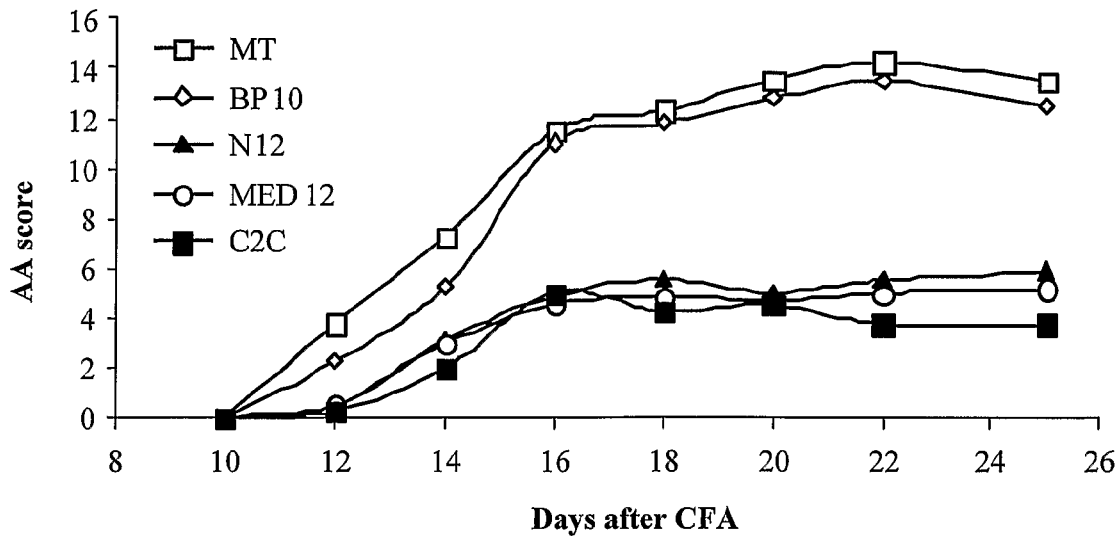
FIG. 10 illustrates inhibition of AA by transfer of T-cell lines to C1/2 determinants.
Figure 10B:
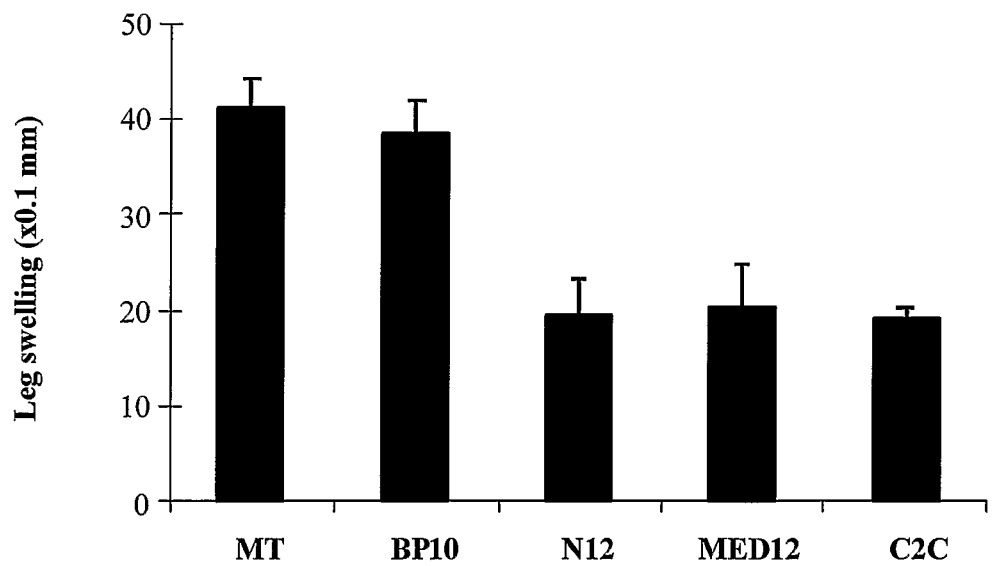

To learn whether T-cell lines reactive with C1/2 determinants could transfer the inhibition of AA, we transferred ip the activated cells ($15 \times 10^5$ cells/rat) at days −3, 4 and 11 relative to the induction of AA. As a control, we used a T-cell line raised against guinea pig myelin basic protein (BP10). FIG. 10 shows that the recipients of the T-cell lines specific for C1/2 determinants (N12, MED12 or C2C) manifested a significantly milder disease than recipients of the control line BP10, as reflected in disease severity (FIG. 10A) and ankle swelling (FIG. 10B).

Example 10

T-Cell Lines to C1/2 Determinants Proliferate to Activated T Cells

Figure 11A:
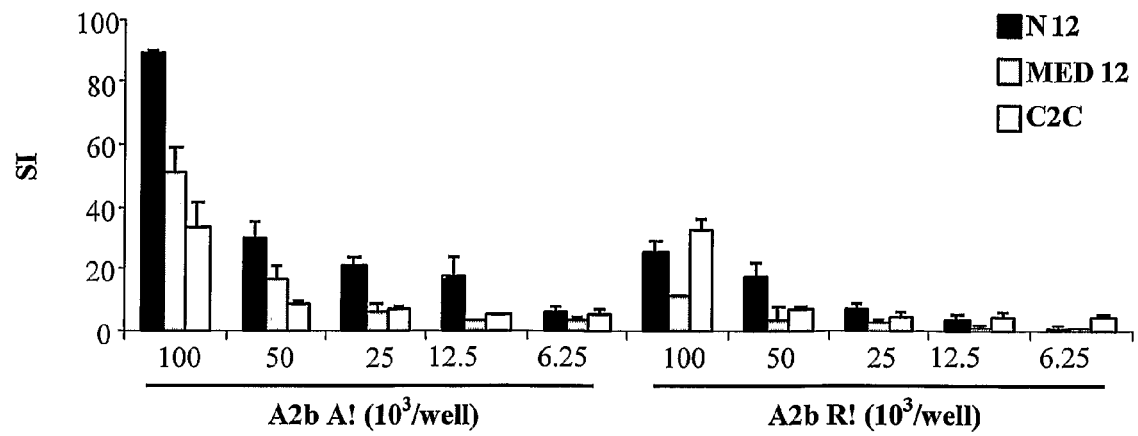
FIG. 11 illustrates anti-ergotypic responses of T-cell lines to C1/2 determinants.
Figure 11B:
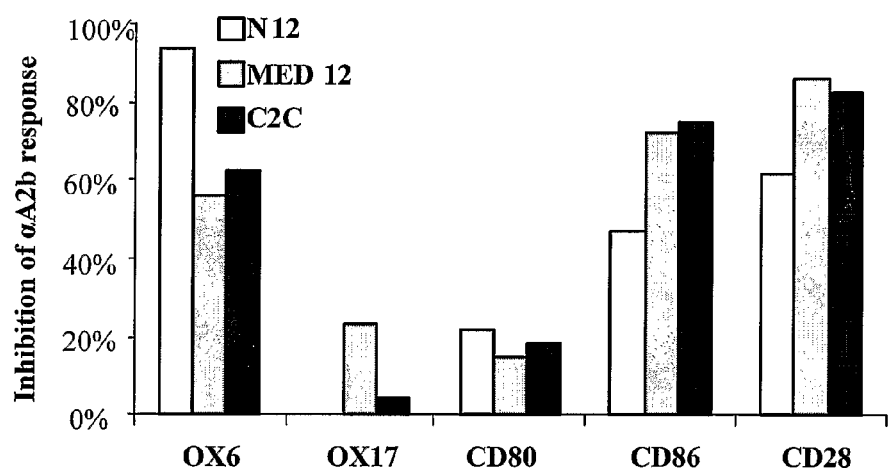

We studied the proliferative responses of the T-cell lines to C1/2 determinants triggered by co-incubation with activated or resting T cell lines. FIG. 11A shows that the N12, MED12 and C2C lines proliferate upon incubation with activated A2b T cells. Experiments done in the presence of blocking antibodies indicated that the proliferative response to activated T cells was mediated by MHC class II, CD28 and CD86 interactions (FIG. 11B). Thus, T-cell lines to C1/2 determinants are anti-ergotypic.

Figure 12:
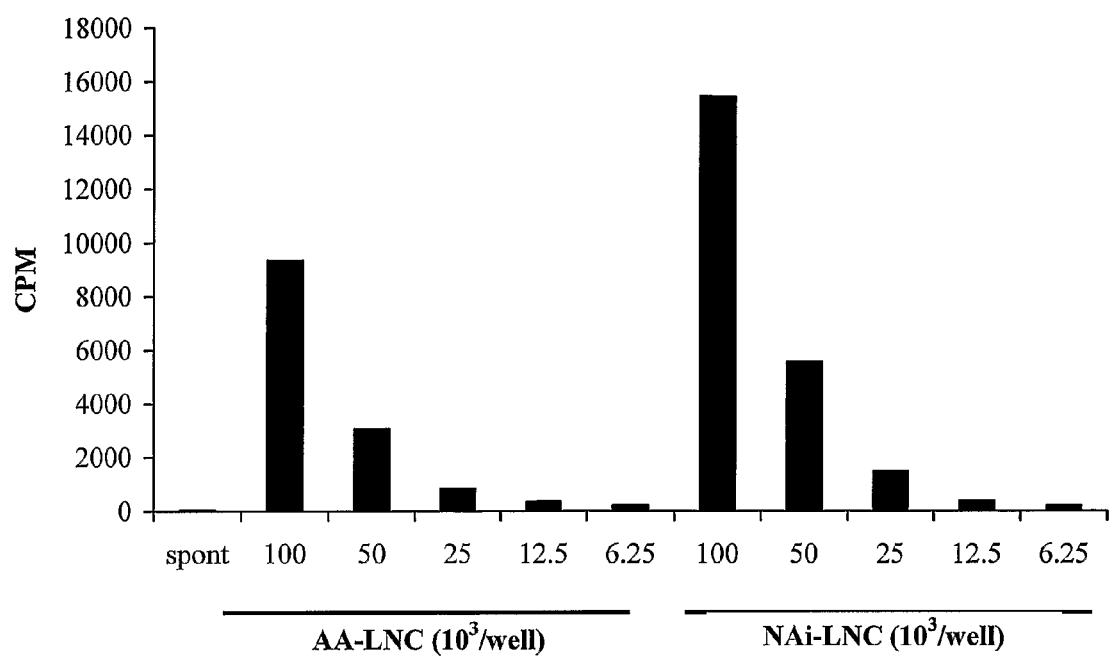
FIG. 12 illustrates proliferative responses of T cell lines to C1/2 determinants.

In addition, we followed the proliferative response directed to activated LNC isolated from arthritic or naïve rats. The T-cell lines to C1/2 determinants proliferated upon activation with LNC that were previously activated with Con A (2.5 µg/ml) (FIG. 12). This proliferation could be inhibited with specific antibodies directed against CD28 and OX6.

Example 11

Location of HLA-DR Binding Regions in the Constant Domain of the T Cell Receptor Using ProPred Algorithm for Identifying HLA-DR Binding Sites A search was performed for HLA-DR binding regions in the constant domain of the T Cell Receptor using the ProPred Algorithm of Singh, H. and Raghava (2001). More specifically, the following specific chains were searched: alpha (Accession No. gi:1335335), beta-1 (Accession No. gi:338831), beta-2 (Accession No. gi:88760), delta (Accession No. gi:107835), gamma (Accession Nos: A26659, AAB63314, AAB63312, and AAB63313). The following MHC-II alleles were considered in the analysis: DRB1_0101, DRB1_0102, DRB1_0301, DRB1_0305, DRB1_0306, DRB1_0307, DRB1_0308, DRB1_0309, DRB1_0311, DRB1_0401, DRB1_0402, DRB1_0404, DRB1_0405, DRB1_0408, DRB1_0410, DRB1_0421, DRB1_0423, DRB1_0426, DRB1_0701, DRB1_0703, DRB1_0801, DRB1_0802, DRB1_0804, DRB1_0806, DRB1_0813, DRB1_0817, DRB1_1101, DRB1_1102, DRB1_1104, DRB1_1106, DRB1_1107, DRB1_1114, DRB1_1120, DRB1_1121, DRB1_1128, DRB1_1301, DRB1_1302, DRB1_1304, DRB1_1305, DRB1_1307, DRB1_1311, DRB1_1321, DRB1_1322, DRB1_1323, DRB1_1327, DRB1_1328, DRB1_1501, DRB1_1502, DRB1_1506, DRB5_0101, and DRB5_0105. The results are presented in Tables 2-9, presenting predicted MHC-II binding peptides. It is noted that all of the peptides presented in Tables 2-9 are arbitrarily exactly nine amino acids long. It is explicitly to be understood that the peptides used in accordance with the present invention may include either extensions or truncations as long as they preserve the intended function of suppressing autoimmune inflammatory disease.

TABLE 2

MHC-II Binding Peptides for the Alpha Chain

| SEQ ID NO: | Amino Acid Sequence |
|---|---|
| 1 | Phe-Lys-Ser-Asn-Ser-Ala-Val-Ala-Trp |
| 2 | Val-Ala-Trp-Ser-Asn-Lys-Ser-Asp-Phe |
| 3 | Tyr-Ile-Thr-Asp-Lys-Thr-Val-Leu-Asp |
| 4 | Tyr-Gln-Leu-Arg-Asp-Ser-Lys-Ser-Ser |
| 5 | Phe-Asp-Ser-Gln-Thr-Asn-Val-Ser-Gln |
| 6 | Val-Tyr-Gln-Leu-Arg-Asp-Ser-Lys-Ser |
| 7 | Val-Leu-Asp-Met-Arg-Ser-Met-Asp-Phe |
| 8 | Val-Tyr-Ile-Thr-Asp-Lys-Thr-Val-Leu |
| 9 | Ile-Thr-Asp-Lys-Thr-Val-Leu-Asp-Met |
| 10 | Val-Cys-Leu-Phe-Thr-Asp-Phe-Asp-Ser |
| 11 | Met-Arg-Ser-Met-Asp-Phe-Lys-Ser-Asn |
| 12 | Phe-Gln-Asn-Leu-Ser-Val-Ile-Gly-Phe |
| 13 | Phe-Arg-Ile-Leu-Leu-Leu-Lys-Val-Ala |
| 14 | Ile-Leu-Leu-Leu-Lys-Val-Ala-Gly-Phe |
| 15 | Leu-Leu-Lys-Val-Ala-Gly-Phe-Asn-Leu |
| 16 | Phe-Asn-Leu-Leu-Met-Thr-Leu-Arg-Leu |
| 17 | Val-Lys-Leu-Val-Glu-Lys-Ser-Phe-Glu |
| 18 | Leu-Leu-Met-Thr-Leu-Arg-Leu-Trp-Ser |
| 19 | Phe-Asn-Asn-Ser-Ile-Ile-Pro-Glu-Asp |
| 20 | Phe-Glu-Thr-Asp-Thr-Asn-Leu-Asn-Phe |
| 21 | Ile-Ile-Pro-Glu-Asp-Thr-Phe-Phe-Pro |
| 22 | Ile-Gly-Phe-Arg-Ile-Leu-Leu-Leu-Lys |
| 23 | Val-Ile-Gly-Phe-Arg-Ile-Leu-Leu-Leu |
| 24 | Leu-Lys-Val-Ala-Gly-Phe-Asn-Leu-Leu |
| 25 | Leu-Leu-Leu-Lys-Val-Ala-Gly-Phe-Asn |
| 26 | Leu-Met-Thr-Leu-Arg-Leu-Trp-Ser-Ser |
| 27 | Val-Ala-Gly-Phe-Asn-Leu-Leu-Met-Thr |

TABLE 3

MHC-II Binding Peptides for the Beta Chain Variant Molecule 1

| SEQ ID NO: | Amino Acid Sequence |
|---|---|
| 28 | Leu-Asn-Lys-Val-Phe-Pro-Pro-Glu-Va |
| 29 | Leu-Val-Cys-Leu-Ala-Thr-Gly-Phe-Phe |
| 30 | Phe-Phe-Pro-Asp-His-Val-Glu-Leu-Ser |
| 31 | Trp-Trp-Val-Asn-Gly-Lys-Glu-Val-His |
| 32 | Trp-Val-Asn-Gly-Lys-Glu-Val-His-Ser |
| 33 | Phe-Glu-Pro-Ser-Glu-Ala-Glu-Ile-Ser |

TABLE 3-continued

MHC-II Binding Peptides for the Beta Chain Variant Molecule 1

| SEQ ID NO: | Amino Acid Sequence |
|---|---|
| 34 | Val-Ala-Val-Phe-Glu-Pro-Ser-Glu-Ala |
| 35 | Val-Asn-Gly-Lys-Glu-Val-His-Ser-Gly |
| 36 | Val-Ser-Thr-Asp-Pro-Gln-Pro-Leu-Lys |
| 37 | Ile-Val-Ser-Ala-Glu-Ala-Trp-Gly-Arg |
| 38 | Leu-Arg-Val-Ser-Ala-Thr-Phe-Trp-Gln |
| 39 | Tyr-Cys-Leu-Ser-Ser-Arg-Leu-Arg-Val |
| 40 | Phe-Arg-Cys-Gln-Val-Gln-Phe-Tyr-Gly |
| 41 | Tyr-Gly-Leu-Ser-Glu-Asn-Asp-Glu-Trp |
| 42 | Val-Thr-Gln-Ile-Val-Ser-Ala-Glu-Ala |
| 43 | Val-Gln-Phe-Tyr-Gly-Leu-Ser-Glu-Asn |
| 44 | Leu-Ser-Ser-Arg-Leu-Arg-Val-Ser-Ala |
| 45 | Trp-Gln-Asn-Pro-Arg-Asn-His-Phe-Arg |
| 46 | Tyr-Glu-Ile-Leu-Leu-Gly-Lys-Ala-Thr |
| 47 | Tyr-Ala-Val-Leu-Val-Ser-Ala-Leu-Val |
| 48 | Leu-Val-Ser-Ala-Leu-Val-Leu-Met-Ala |
| 49 | Leu-Val-Leu-Met-Ala-Met-Val-Lys-Arg |
| 50 | Val-Ser-Tyr-Gln-Gln-Gly-Val-Leu-Ser |
| 51 | Val-Leu-Val-Ser-Ala-Leu-Val-Leu-Met |
| 52 | Val-Leu-Met-Ala-Met-Val-Lys-Arg-Lys |
| 53 | Ile-Leu-Tyr-Glu-Ile-Leu-Leu-Gly-Lys |
| 54 | Leu-Leu-Gly-Lys-Ala-Thr-Leu-Tyr-Ala |
| 55 | Leu-Tyr-Ala-Val-Leu-Val-Ser-Ala-Leu |
| 56 | Val-Leu-Ser-Ala-Thr-Ile-Leu-Tyr-Glu |
| 57 | Leu-Ser-Ala-Thr-Ile-Leu-Tyr-Glu-Ile |
| 58 | Leu-Met-Ala-Met-Val-Lys-Arg-Lys-Asp |
| 59 | Val-Ser-Ala-Leu-Val-Leu-Met-Ala-Met |
| 60 | Met-Ala-Met-Val-Lys-Arg-Lys-Asp-Phe |

TABLE 4

MHC-II Binding Peptides for the Beta Chain Variant Molecule 2

| SEQ ID NO. | Amino Acid Sequence |
|---|---|
| 31 | Trp-Trp-Val-Asn-Gly-Lys-Glu-Val-His |
| 32 | Trp-Val-Asn-Gly-Lys-Glu-Val-His-Ser |
| 33 | Phe-Glu-Pro-Ser-Glu-Ala-Glu-Ile-Ser |
| 34 | Val-Ala-Val-Phe-Glu-Pro-Ser-Glu-Ala |
| 35 | Val-Asn-Gly-Lys-Glu-Val-His-Ser-Gly |
| 36 | Val-Ser-Thr-Asp-Pro-Gln-Pro-Leu-Lys |

TABLE 4-continued

MHC-II Binding Peptides for the Beta Chain Variant Molecule 2

| SEQ ID NO. | Amino Acid Sequence |
|---|---|
| 37 | Ile-Val-Ser-Ala-Glu-Ala-Trp-Gly-Arg |
| 38 | Leu-Arg-Val-Ser-Ala-Thr-Phe-Trp-Gln |
| 39 | Tyr-Cys-Leu-Ser-Ser-Arg-Leu-Arg-Val |
| 40 | Phe-Arg-Cys-Gln-Val-Gln-Phe-Tyr-Gly |
| 41 | Tyr-Gly-Leu-Ser-Glu-Asn-Asp-Glu-Trp |
| 42 | Val-Thr-Gln-Ile-Val-Ser-Ala-Glu-Ala |
| 43 | Val-Gln-Phe-Tyr-Gly-Leu-Ser-Glu-Asn |
| 44 | Leu-Ser-Ser-Arg-Leu-Arg-Val-Ser-Ala |
| 45 | Trp-Gln-Asn-Pro-Arg-Asn-His-Phe-Arg |
| 46 | Tyr-Glu-Ile-Leu-Leu-Gly-Lys-Ala-Thr |
| 47 | Tyr-Ala-Val-Leu-Val-Ser-Ala-Leu-Val |
| 48 | Leu-Val-Ser-Ala-Leu-Val-Leu-Met-Ala |
| 49 | Leu-Val-Leu-Met-Ala-Met-Val-Lys-Arg |
| 51 | Val-Leu-Val-Ser-Ala-Leu-Val-Leu-Met |
| 52 | Val-Leu-Met-Ala-Met-Val-Lys-Arg-Lys |
| 53 | Ile-Leu-Tyr-Glu-Ile-Leu-Leu-Gly-Lys |
| 54 | Leu-Leu-Gly-Lys-Ala-Thr-Leu-Tyr-Ala |
| 55 | Leu-Tyr-Ala-Val-Leu-Val-Ser-Ala-Leu |
| 56 | Val-Leu-Ser-Ala-Thr-Ile-Leu-Tyr-Glu |
| 57 | Leu-Ser-Ala-Thr-Ile-Leu-Tyr-Glu-Ile |
| 58 | Leu-Met-Ala-Met-Val-Lys-Arg-Lys-Asp |
| 59 | Val-Ser-Ala-Leu-Val-Leu-Met-Ala-Met |
| 61 | Leu-Lys-Asn-Val-Phe-Pro-Pro-Glu-Val |
| 62 | Leu-Val-Cys-Leu-Ala-Thr-Gly-Phe-Tyr |
| 63 | Phe-Tyr-Pro-Asp-His-Val-Glu-Leu-Ser |
| 64 | Met-Ala-Met-Val-Lys-Arg-Lys-Asp-Ser |

TABLE 5

MHC-II Binding Peptides for the Delta Chain

| SEQ ID NO. | Amino Acid Sequence |
|---|---|
| 65 | Phe-Val-Met-Lys-Asn-Gly-Thr-Asn-Val |
| 66 | Ile-Asn-Leu-Val-Ser-Ser-Lys-Lys-Ile |
| 67 | Ile-Arg-Ile-Asn-Leu-Val-Ser-Ser-Lys |
| 68 | Leu-Val-Ser-Ser-Lys-Lys-Ile-Thr-Glu |
| 69 | Ile-Val-Ile-Ser-Pro-Ser-Gly-Lys-Tyr |
| 70 | Tyr-Pro-Lys-Asp-Ile-Arg-Ile-Asn-Leu |
| 71 | Val-Met-Lys-Asn-Gly-Thr-Asn-

TABLE 5-continued

MHC-II Binding Peptides for the Delta Chain

| SEQ ID NO. | Amino Acid Sequence |
|---|---|
| 72 | Val-Lys-Leu-Gly-Lys-Tyr-Glu-Asp-Ser |
| 73 | Met-Lys-Asn-Gly-Thr-Asn-Val-Ala-Cys |
| 74 | Val-Phe-Val-Met-Lys-Asn-Gly-Thr-Asn |
| 75 | Phe-Tyr-Pro-Lys-Asp-Ile-Arg-Ile-Asn |
| 76 | Tyr-Asn-Ala-Val-Lys-Leu-Gly-Lys-Tyr |
| 77 | Val-Gln-His-Asp-Asn-Lys-Thr-Val-His |
| 78 | Val-Lys-Thr-Asp-Ser-Thr-Asp-His-Val |
| 79 | Val-Asn-Met-Met-Ser-Leu-Thr-Val-Leu |
| 80 | Met-Met-Ser-Leu-Thr-Val-Leu-Gly-Leu |
| 81 | Leu-Arg-Met-Leu-Phe-Ala-Lys-Thr-Val |
| 82 | Met-Leu-Phe-Ala-Lys-Thr-Val-Ala-Val |
| 83 | Val-Asn-Phe-Leu-Leu-Thr-Ala-Lys-Leu |
| 84 | Ile-Val-His-Thr-Glu-Lys-Val-Asn-Met |
| 85 | Phe-Leu-Leu-Thr-Ala-Lys-Leu-Phe-Phe |
| 86 | Val-His-Thr-Glu-Lys-Val-Asn-Met-Met |
| 87 | Phe-Ala-Lys-Thr-Val-Ala-Val-Asn-Phe |
| 88 | Leu-Leu-Thr-Ala-Lys-Leu-Phe-Phe-Leu |
| 89 | Leu-Phe-Ala-Lys-Thr-Val-Ala-Val-Asn |
| 90 | Leu-Gly-Leu-Arg-Met-Leu-Phe-Ala-Lys |
| 91 | Val-Leu-Gly-Leu-Arg-Met-Leu-Phe-Ala |
| 92 | Val-Ala-Val-Asn-Phe-Leu-Leu-Thr-Ala |

TABLE 6

MHC-II Binding Peptides for the Gamma Chain Variant Molecule

| SEQ ID NO: | Amino Acid Sequence |
|---|---|
| 93 | Phe-Phe-Pro-Asp-Val-Ile-Lys-Ile-His |
| 94 | Ile-Lys-Ile-His-Trp-Gln-Glu-Lys-Lys |
| 95 | Phe-Leu-Pro-Ser-Ile-Ala-Glu-Thr-Lys |
| 96 | Leu-Gln-Lys-Ala-Gly-Thr-Tyr-Leu-Cys |
| 97 | Trp-Gln-Glu-Lys-Lys-Ser-Asn-Thr-Ile |
| 98 | Val-Ser-Pro-Lys-Pro-Thr-Ile-Phe-Leu |
| 99 | Leu-Cys-Leu-Leu-Glu-Lys-Phe-Phe-Pro |
| 100 | Ile-His-Trp-Gln-Glu-Lys-Lys-Ser-Asn |
| 101 | Val-Ile-Lys-Ile-His-Trp-Gln-Glu-Lys |
| 102 | Ile-Lys-Thr-Asp-Val-Ile-Thr-Met-Asp |
| 103 | Ile-Thr-Met-Asp-Pro-Lys-Asp-Asn-Cys |
| 104 | Ile-Val-Arg-His-Glu-Asn-Asn-Lys-Asn |

TABLE 6-continued

MHC-II Binding Peptides for the Gamma Chain Variant Molecule

| SEQ ID NO: | Amino Acid Sequence |
|---|---|
| 105 | Val-Arg-His-Glu-Asn-Asn-Lys-Asn-Gly |
| 106 | Phe-Pro-Pro-Ile-Lys-Thr-Asp-Val-Ile |
| 107 | Met-Lys-Thr-Asn-Asp-Thr-Tyr-Met-Lys |
| 108 | Tyr-Met-Lys-Phe-Ser-Trp-Leu-Thr-Val |
| 109 | Val-Ile-Thr-Met-Asp-Pro-Lys-Asp-Asn |
| 110 | Phe-Ser-Trp-Leu-Thr-Val-Pro-Glu-Lys |
| 111 | Trp-Leu-Thr-Val-Pro-Glu-Lys-Ser-Leu |
| 112 | Tyr-Leu-Leu-Leu-Leu-Lys-Ser-Val |
| 113 | Leu-Leu-Leu-Leu-Lys-Ser-Val-Val-Tyr |
| 114 | Val-Val-Tyr-Phe-Ala-Ile-Ile-Thr-Cys |
| 115 | Tyr-Phe-Ala-Ile-Ile-Thr-Cys-Cys-Leu |
| 116 | Phe-Ala-Ile-Ile-Thr-Cys-Cys-Leu-Leu |
| 117 | Leu-Leu-Leu-Gln-Leu-Thr-Asn-Thr-Ser |
| 118 | Leu-Leu-Gln-Leu-Thr-Asn-Thr-Ser-Ala |
| 119 | Met-Tyr-Leu-Leu-Leu-Leu-Lys-Ser |
| 120 | Leu-Leu-Leu-Leu-Lys-Ser-Val-Val |
| 121 | Leu-Leu-Leu-Lys-Ser-Val-Val-Tyr-Phe |
| 122 | Tyr-Met-Tyr-Leu-Leu-Leu-Leu-Lys |
| 123 | Leu-Leu-Lys-Ser-Val-Val-Tyr-Phe-Ala |
| 124 | Val-Tyr-Phe-Ala-Ile-Ile-Thr-Cys-Cys |
| 125 | Leu-Gln-Leu-Thr-Asn-Thr-Ser-Ala-Tyr |
| 126 | Leu-Leu-Arg-Arg-Thr-Ala-Phe-Cys-Cys |
| 127 | Leu-Thr-Asn-Thr-Ser-Ala-Tyr-Tyr-Met |
| 128 | Tyr-Tyr-Met-Tyr-Leu-Leu-Leu-Leu |
| 129 | Leu-Lys-Ser-Val-Val-Tyr-Phe-Ala-Ile |
| 130 | Ile-Ile-Thr-Cys-Cys-Leu-Leu-Arg-Arg |

TABLE 7

MHC-II Binding Peptides for the Gamma Chain Variant Molecule

| SEQ ID NO. | Amino Acid Sequence |
|---|---|
| 93 | Phe-Phe-Pro-Asp-Val-Ile-Lys-Ile-His |
| 94 | Ile-Lys-Ile-His-Trp-Gln-Glu-Lys-Lys |
| 95 | Phe-Leu-Pro-Ser-Ile-Ala-Glu-Thr-Lys |
| 96 | Leu-Gln-Lys-Ala-Gly-Thr-Tyr-Leu-Cys |
| 97 | Trp-Gln-Glu-Lys-Lys-Ser-Asn-Thr-Ile |
| 98 | Val-Ser-Pro-Lys-Pro-Thr-Ile-Phe-Leu |

TABLE 7-continued

MHC-II Binding Peptides for the Gamma Chain Variant Molecule

| SEQ ID NO. | Amino Acid Sequence |
|---|---|
| 99 | Leu-Cys-Leu-Leu-Glu-Lys-Phe-Phe-Pro |
| 100 | Ile-His-Trp-Gln-Glu-Lys-Lys-Ser-Asn |
| 101 | Val-Ile-Lys-Ile-His-Trp-Gln-Glu-Lys |
| 102 | Ile-Lys-Thr-Asp-Val-Ile-Thr-Met-Asp |
| 103 | Ile-Thr-Met-Asp-Pro-Lys-Asp-Asn-Cys |
| 104 | Ile-Val-Arg-His-Glu-Asn-Asn-Lys-Asn |
| 105 | Val-Arg-His-Glu-Asn-Asn-Lys-Asn-Gly |
| 106 | Phe-Pro-Pro-Ile-Lys-Thr-Asp-Val-Ile |
| 107 | Met-Lys-Thr-Asn-Asp-Thr-Tyr-Met-Lys |
| 108 | Tyr-Met-Lys-Phe-Ser-Trp-Leu-Thr-Val |
| 109 | Val-Ile-Thr-Met-Asp-Pro-Lys-Asp-Asn |
| 110 | Phe-Ser-Trp-Leu-Thr-Val-Pro-Glu-Lys |
| 111 | Trp-Leu-Thr-Val-Pro-Glu-Lys-Ser-Leu |
| 112 | Tyr-Leu-Leu-Leu-Leu-Lys-Ser-Val |
| 113 | Leu-Leu-Leu-Leu-Lys-Ser-Val-Val-Tyr |
| 114 | Val-Val-Tyr-Phe-Ala-Ile-Ile-Thr-Cys |
| 115 | Tyr-Phe-Ala-Ile-Ile-Thr-Cys-Cys-Leu |
| 116 | Phe-Ala-Ile-Ile-Thr-Cys-Cys-Leu-Leu |
| 117 | Leu-Leu-Leu-Gln-Leu-Thr-Asn-Thr-Ser |
| 118 | Leu-Leu-Gln-Leu-Thr-Asn-Thr-Ser-Ala |
| 119 | Met-Tyr-Leu-Leu-Leu-Leu-Lys-Ser |
| 120 | Leu-Leu-Leu-Leu-Leu-Lys-Ser-Val-Val |
| 121 | Leu-Leu-Leu-Lys-Ser-Val-Val-Tyr-Phe |
| 122 | Tyr-Met-Tyr-Leu-Leu-Leu-Leu-Lys |
| 123 | Leu-Leu-Lys-Ser-Val-Val-Tyr-Phe-Ala |
| 124 | Val-Tyr-Phe-Ala-Ile-Ile-Thr-Cys-Cys |
| 125 | Leu-Gln-Leu-Thr-Asn-Thr-Ser-Ala-Tyr |
| 126 | Leu-Leu-Arg-Arg-Thr-Ala-Phe-Cys-Cys |
| 127 | Leu-Thr-Asn-Thr-Ser-Ala-Tyr-Tyr-Met |
| 128 | Tyr-Tyr-Met-Tyr-Leu-Leu-Leu-Leu |
| 129 | Leu-Lys-Ser-Val-Val-Tyr-Phe-Ala-Ile |
| 130 | Ile-Ile-Thr-Cys-Cys-Leu-Leu-Arg-Arg |
| 131 | Phe-Phe-Pro-Asp-Val-Ser-Pro-Lys-Pro |

TABLE 8

MHC-II Binding Peptides for the Gamma Chain Variant Molecule

| SEQ ID NO. | Amino Acid Sequence |
|---|---|
| 93 | Phe-Phe-Pro-Asp-Val-Ile-Lys-Ile-His |
| 94 | Ile-Lys-Ile-His-Trp-Gln-Glu-Lys-Lys |
| 95 | Phe-Leu-Pro-Ser-Ile-Ala-Glu-Thr-Lys |
| 96 | Leu-Gln-Lys-Ala-Gly-Thr-Tyr-Leu-Cys |
| 97 | Trp-Gln-Glu-Lys-Lys-Ser-Asn-Thr-Ile |
| 98 | Val-Ser-Pro-Lys-Pro-Thr-Ile-Phe-Leu |
| 99 | Leu-Cys-Leu-Leu-Glu-Lys-Phe-Phe-Pro |
| 100 | Ile-His-Trp-Gln-Glu-Lys-Lys-Ser-Asn |
| 104 | Ile-Val-Arg-His-Glu-Asn-Asn-Lys-Asn |
| 105 | Val-Arg-His-Glu-Asn-Asn-Lys-Asn-Gly |
| 106 | Phe-Pro-Pro-Ile-Lys-Thr-Asp-Val-Ile |
| 107 | Met-Lys-Thr-Asn-Asp-Thr-Tyr-Met-Lys |
| 108 | Tyr-Met-Lys-Phe-Ser-Trp-Leu-Thr-Val |
| 109 | Val-Ile-Thr-Met-Asp-Pro-Lys-Asp-Asn |
| 112 | Tyr-Leu-Leu-Leu-Leu-Lys-Ser-Val |
| 113 | Leu-Leu-Leu-Leu-Lys-Ser-Val-Val-Tyr |
| 114 | Val-Val-Tyr-Phe-Ala-Ile-Ile-Thr-Cys |
| 115 | Tyr-Phe-Ala-Ile-Ile-Thr-Cys-Cys-Leu |
| 116 | Phe-Ala-Ile-Ile-Thr-Cys-Cys-Leu-Leu |
| 117 | Leu-Leu-Leu-Gln-Leu-Thr-Asn-Thr-Ser |
| 118 | Leu-Leu-Gln-Leu-Thr-Asn-Thr-Ser-Ala |
| 119 | Met-Tyr-Leu-Leu-Leu-Leu-Lys-Ser |
| 120 | Leu-Leu-Leu-Leu-Leu-Lys-Ser-Val-Val |
| 121 | Leu-Leu-Leu-Lys-Ser-Val-Val-Tyr-Phe |
| 122 | Tyr-Met-Tyr-Leu-Leu-Leu-Leu-Lys |
| 123 | Leu-Leu-Lys-Ser-Val-Val-Tyr-Phe-Ala |
| 124 | Val-Tyr-Phe-Ala-Ile-Ile-Thr-Cys-Cys |
| 125 | Leu-Gln-Leu-Thr-Asn-Thr-Ser-Ala-Tyr |
| 127 | Leu-Thr-Asn-Thr-Ser-Ala-Tyr-Tyr-Met |
| 128 | Tyr-Tyr-Met-Tyr-Leu-Leu-Leu-Leu |
| 129 | Leu-Lys-Ser-Val-Val-Tyr-Phe-Ala-Ile |
| 131 | Phe-Phe-Pro-Asp-Val-Ser-Pro-Lys-Pro |
| 132 | Ile-Lys-Ile-His-Trp-Gln-Lys-Gln-Leu |
| 133 | Phe-Phe-Pro-Asp-Ile-Ile-Lys-Ile-His |
| 134 | Ile-Ile-Lys-Ile-His-Trp-Gln-Glu-Lys |
| 135 | Ile-Lys-Thr-Asp-Val-Thr-Thr-Val-Asp |
| 136 | Phe-Ser-Trp-Leu-Thr-Val-Pro-Glu-Glu |
| 137 | Ile-Thr-Met-Asp-Pro-Lys-Asp-Asn-Trp |

TABLE 8-continued

MHC-II Binding Peptides for the Gamma Chain Variant Molecule

| SEQ ID NO. | Amino Acid Sequence |
|---|---|
| 138

TABLE 10-continued

TCR constant domain chains

C. TCR beta-2 chain constant domain (gi: 88760, SEQ ID NO: 170):

```
edlknvfppe vavfepseae ishtqkatlv clatgfypdh velswwvngk evhsgvstdp qplkeqpaln
dsryclssrl rvsatfwqnp rnhfrcqvqf yglsendewt qdrakpvtqi vsaeawgrad cgftsesyqq gvlsatilye
illgkatlya vlvsalvlma mvkrkdsrg
Coding sequence - gi: 338832, SEQ ID NO: 178.
```

D. TCR delta chain constant domain - gi: 107835, SEQ ID NO: 171:

```
sqphtkpsvf vmkngtnvac lvkefypkdi rinlvsskki tefdpaivis psgkynavkl gkyedsnsvt
csvqhdnktv hstdfevktd stdhvkpket entkqpsksc hkpkaivhte kvnmmsltvl glrmlfaktv
avnflltakl ffl
Coding sequence - gi: 339030, SEQ ID NO: 179.
```

E. TCR gamma-1 chain constant domain - A26659, SEQ ID NO: 172:

```
dkqldadvsp kptiflpsia etklqkagty lcllekffpd vikihwqekk sntilgsqeg ntmktndtym
kfswltvpek sldkehrciv rhennkngvd qeiifppikt dvitmdpkdn cskdandtll lqltntsayy myllllksv
vyfaiitccl lrrtafccng eks
```

F. TCR gamma chain constant domain - AAB63314, SEQ ID NO: 173:

```
vspkptiflp siaetklqka gtylcllekf fpdvikihwq ekksntilgs qegntmktnd tymkfswltv peksldkehr
civrhennkn gvdqeiifpp iktdvitmdp kdncskdand tlllqltnts ayymylllll ksvvyfaiit ccllrrtafc
cngeks
Coding sequence - gi: 2072752, SEQ ID NO: 180.
```

G. TCR gamma chain constant domain (AAB63312, SEQ ID NO: 174):

```
kqldadvspk ptiflpsiae tklqkagtyl cllekffpdi ikihwqekks ntilgsqegn tmktndtymk fswltvpees
ldkehrcivr hennkngidq eiifppiktd vttvdpkdsy skdandvttv dpkynyskda ndvitmdpkd
nwskdandtl llqltntsay ymylllllks vvyfaiitcc llgrtafccn geks
Coding sequence - gi: 2072750, SEQ ID NO: 181:
```

H. TCR gamma chain constant domain -AAB63313, SEQ ID NO: 175:

```
kqldadvspk ptiflpsiae tklqkagtyl cllekffpdi ikihwqekks ntilgsqegn tmktndtymk fswltvpees
ldkebrcivr hennkngidq eiifppiktd vttvdpkyny skdandvitm dpkdnwskda idtlllqltn
tsayymylll llksgvyfai itccllrrta fccngeks
Coding sequence (gi: 2072751, SEQ ID NO: 182):
```

Example 12

Screening for Immunogenic TCR Constant Domain Peptides Using Antigen Array Technology The antigenicity of peptides derived from human T-cell receptor gamma-chain constant region (accession no: AAB63314; SEQ ID NO:173) was assayed using antigen array technology, as detailed below.

Serum samples: Blood samples were obtained by random availability from 12 healthy adults and from 9 adults newly diagnosed with lung cancer, before treatment. All samples were collected with informed consent and approval of the Helsinki committee of the Sheba Medical Center, Tel Hashomer, Israel. The blood samples were allowed to clot at room temperature. After centrifugation, sera were collected and stored at −20° C.

Antigen microarray: Antigens diluted in PBS were placed in 384-well plates at a concentration of 1 µg/µl. We used a robotic MicroGrid arrayer with solid spotting pins of 0.2 mm in diameter (BioRobotics, Cambridge, U.K.) to spot the antigens onto ArrayIt SuperEpoxi microarray substrate slides (TeleChem, Sunnyvale, Calif.). the antigens were spotted in replicates of 4, and the microarrays were blocked for 1 h at 37° C. with 1% bovine serum albumin, and incubated under a cover-slip overnight at 4° C. with a 1:5 dilution of the test serum in blocking buffer. The quantitative range of signal intensity of binding to each antigen spot was 0.01-65,000, and this range of detection made it possible to record reliable data with little dilution of test samples. The arrays were then washed and incubated for 1 hour at 37° C. with a 1:500 dilution of detection antibodies. Two detection antibodies were used: a goat anti-human IgG Cy3-conjugated antibody and a goat anti-human IgM Cy5-conjugated antibody, purchased from Jackson ImmunoResearch, West Grove, Pa. The arrays were washed again, spin-dried, and scanned with a ScanArray 4000× scanner (GSI Luminomics, Billerica, Mass.). The results were recorded as TIFF files. Image acquisition by laser and quantification were done as described (Quintana et al., 2004).

Data preprocessing and background filtering: Antigen reactivity was defined by the mean intensity of the 4 replicates of binding to that antigen on the microarray. We identified positive antibodies in the following way: To establish the minimum level of significant antibody binding, we calculated the mean reactivity level of 32 spots incubated with phosphate buffered saline (PBS) in place of an antigen on each microarray slide. A signal was scored as positive when it expressed intensity greater than the upper limit of the PBS control, which was defined as the mean intensity of the PBS spots plus 2-times the standard deviation. Signal intensity above the PBS background was considered positive antibody binding.

Peptide antigens having an amino acid sequence as set forth in SEQ ID NOS:157-163, presented in Table 11, were identified, using an algorithm for prediction of immunogenic sequences (http://bio.dfci.harvard.edu/Tools/antigenic.h- tml), from seven different parts of the protein (see the starting and ending aa positions). Peptides having an amino acid sequence as set forth in SEQ ID NOS:158, 161 and 164-167, were synthesized and used for the analysis. The tested peptides (Table 12) were as follows:

a) SEQ ID NO:164—a combination of SEQ ID NOS:157 and 159 in tandem;
b) SEQ ID NO:158;
c) SEQ ID NO:165—a combination of SEQ ID NOS:160 and 162 in tandem;
d) SEQ ID NO:161;
e) SEQ ID NOS:166 and 167 are two partially overlapping 20 mers of SEQ ID NO:163.

sequence as set forth in SEQ ID NO:164. IgG antibodies reactive with all but the peptide denoted by SEQ ID NO:164 were found in the sera of lung cancer subjects, indicating the ability of these peptides to elicit IgG antibodies in humans. Antibodies from control subjects responded only to the peptide denoted by SEQ ID NO:158. Thus, according to certain particular embodiments, immunogenic peptides and probes of the invention include, without limitation, the peptides having an amino acid sequence as set forth in any one of SEQ ID NOS:157-167, preferably peptides having an amino acid sequence as set forth in any one of SEQ ID NOS:161 and 165-167.

TABLE 11

Predicted Immunogenic Sequences (According To Algorithm)

| SEQ ID NO: | Start Position | SEQUENCE | End Position | Length (aa) |
|---|---|---|---|---|
| 157 | 4 | KPTIFLPS | 11 | 8 |
| 158 | 19 | KAGTYLCLLEKFFPDVIKI | 37 | 19 |
| 159 | 66 | SWLTVPE | 72 | 7 |
| 160 | 77 | KEHRCIV | 83 | 7 |
| 161 | 93 | DQEIIFPPIKT | 103 | 11 |
| 162 | 120 | DTLLLQL | 126 | 7 |
| 163 | 131 | AYYMYLLLLLKSVVYFAIITCCLLRRTAFCCN | 162 | 32 |

TABLE 12

Peptides Synthesized

| SEQ ID NO: | Derived from peptides (SEQ ID NOS.) | SEQUENCE | Length (aa) |
|---|---|---|---|
| 158 | 158 | KAGTYLCLLEKFFPDVIKI | 19 |
| 161 | 161 | DQEIIFPPIKT | 11 |
| 164 | 157 + 159 | KPTIFLPSSWLTVPE | 15 |
| 165 | 160 + 162 | KEHRCIVDTLLLQL | 14 |
| 166 | 163 | AYYMYLLLLLKSVVYFAIIT | 20 |
| 167 |  | VVYFAIITCCLLRRTAFCCN | 20 |

The presence of IgG and IgM in sera obtained from patients with lung cancer and from healthy controls was determined using the antigen microarray, as detailed above. The results, presented in Table 13, represent the mean reactivity of 12 control subjects and 9 lung cancer subjects.

Results: immunoglobulins from lung cancer subjects reacted with all but the peptide having an amino acid

TABLE 13

| | Antigen Binding (Mean Intensity) | | | |
|---|---|---|---|---|
| Peptide | HEALTHY CONTROLS | | LUNG CANCER | |
| (SEQ ID NO:) | IgM | IgG | IgM | IgG |
| 158 | 1753 | 2233 | 2381 | 2116 |
| 161 | 86 | −147 | 160 | 846 |
| 164 | −24 | −240 | 86 | −114 |
| 165 | 97 | 95 | 103 | 1095 |
| 166 | 87 | 199 | 140 | 996 |
| 167 | 548 | 376 | 512 | 1928 |

Table 14 indicates the nucleotide sequences of the peptides:

TABLE 14 corresponding nucleotide sequences

| Peptide SEQ ID NO: | Nucleotide SEQ ID NO: | Nucleotide sequence |
|---|---|---|
| 157 | 183 | aagcccactatttttcttccttca |
| 158 | 184 | aaggctggaacatacctttgtcttcttgagaaattttccctgatgttattaagata |

TABLE 14-continued corresponding nucleotide sequences

| Peptide SEQ ID NO: | Nucleotide SEQ ID NO: | Nucleotide sequence |
|---|---|---|
| 159 | 185 | agctggttaacggtgccagaa |
| 160 | 186 | aaagaacacagatgtatcgtc |
| 161 | 187 | gatcaagaaattatctttcctccaataaagaca |
| 162 | 188 | gatacactactgctgcagctc |
| 163 | 189 | gcatattacatgtacctcctcctgctcctcaagagtgtggtctattttgccatcatcacct gctgtctgcttagaagaacggctttctgc tgcaat |
| 164 | 190 | aagcccactattttcttccttca agctggttaacggtgccagaa |
| 165 | 191 | aaagaacacagatgtatcgtc gatacactactgctgcagctc |
| 166 | 192 | gcatattacatgtacctcctcctgctcctc aagagtgtggtctattttgccatcatcacc |
| 167 | 193 | t gctgtctgcttagaagaacggctttctgc tgcaat |

Example 13

Generation of Human T Cell Lines Directed to TCR Constant Domain Peptides and Determination of an Anti-Ergotypic Response Human T cell lines directed to TCR constant domain epitopes are prepared as follows: peripheral blood mononuclear cells (PBMC) are separated from 50 ml heparinized venous blood on ficoll hypaque, plated in round bottom 96-well microplates, $2\times10^5$ cells per well in the presence of 10-50 µg/ml of the TCR constant domain peptide. The cells are cultured in medium RPMI-1640 (Gibco) supplemented with 10% human serum, 100 U/ml penicillin, 100 µg/ml streptomycin, and 0.1% glutamine in 37° C., 5% $CO_2$ incubator. Following cultivation for 7-14 days, the cultures are split and subcultures are prepared on $10^5$ irradiated (400 Gy) autologous PBMC feeders and restimulated with the peptide. The index of cell stimulation (SI) in response to the peptide is examined after additional 72 h in culture using $^3$H-thymidine incorporation assays (Amersham, Arlington Heights, Ill.). Wells exhibiting a minimal SI>3 (threefold increase in $^3$H-thymidine incorporation relative to the average incorporation in reference control wells not stimulated with peptide) are selected for line propagation and expanded with IL-2 (50 IU/ml, Roche).

To verify that the resulting T cell line is anti-ergotypic, proliferation to autologous activated T cells is determined. To this end, autologous T cells are isolated on a Ficoll gradient, washed, and incubated (2 h, 37° C., 7.5% $CO_2$, humidified atmosphere) on petri dishes. The nonadherent cells are then collected and incubated (1 h, 37° C., 7.5% $CO_2$, humidified atmosphere) on nylon wool columns (Novamed, Jerusalem, Israel). Unbound cells are eluted from the columns by extensive washings. The resulting T cells are activated on anti-CD3 mAb pre-coated 24-well plates (0.5 µg/ml; non tissue culture grade plates) and irradiated (5000 rads). In other experiments, autologous activated T cells are obtained by purification using Macs columns (Miltenyi), activation with anti-CD3 and anti-CD28 Abs, and irradiation. Proliferation of the TCR constant domain peptide-specific T cell line in the presence of the irradiated activated autologous T cells is then determined as described above.

REFERENCES

Cohen, I. R. 2001. *Vaccine* 20:706.
Kumar et al., 2001. *Int Immunol* 13:835.
Hogervorst et al., 1991. *Infect Immun* 59:2029.
Lohse et al., 1989. *Science* 244:820.
Mimran et al., 2004. *J Clin Invest* 113:924.
Minami et al., 1993. *Annu Rev Immunol* 11:245.
Mor et al., 1996. *J Immunol* 157:4855.
Quintana et al., 2002. *J Immunol* 169:3422.
Quintana et al., 2003. *J Immunol* 171:3533
Reizis et al., 1996. *Int Immunol* 8:1825.
Shapira et al., 1993. *J Clin Invest* 91:388.
Singh, H. and Raghava, G. P. S. 2001. *Bioinformatics* 17: 1236-7
Taniguchi, T., and Y. Minami. 1993. *Cell* 73:5.
Van der Aa et al., 2003. *Clin Exp Immunol* 131:155
van Eden et al., 1985. *Proc Natl Acad Sci USA* 82:5117.
Zhang et al., 1993. *Science* 261:1451.
Manolios et al., 1997. *Nat Med* 3: 84-88.
Ben-Nun et al., 1987. *Nature* 292:60.
Holoshitz et. al., 1983. *Science* 219:56.
Achiron et al., 2004. *Clin. Immunol:*113 155-160.
Sambrook et al., 1989. Molecular Cloning: A Laboratory Manual, Cold Spring Harbor Labs Press.
Wolff et al., 1990. *Science* 247, 1465-1468
Stribling et al., 1992. *Proc. Natl. Acad. Sci. USA* 189:11277-11281.
Quintana et al., 2004. *Proc Natl Acad Sci USA* 101 Suppl 2:14615-14621.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials and steps for carrying out various disclosed functions may take a variety of alternative forms without departing from the invention.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A vaccine composition comprising (a) a metabolizable lipid emulsion as an adjuvant; and (b)
   a peptide as set forth in SEQ ID NO: 152 (VLVSALVL-MAMVKKKNS) as an immunogen.

2. A method of treating rheumatoid arthritis comprising administering to a subject in need thereof a therapeutically effective amount of a vaccine composition according to claim 1.

3. The method of claim 2, wherein the peptide elicits an immune response to the constant domain of a TCR chain as measured by an increased anti-ergotypic T cell activity.

4. The method of claim 2, wherein said composition is administered to said subject prior to the appearance of disease symptoms.

* * * * *

SEQUENCE LISTING

```
<160> NUMBER OF SEQ ID NOS: 193

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Phe Lys Ser Asn Ser Ala Val Ala Trp
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Val Ala Trp Ser Asn Lys Ser Asp Phe
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Tyr Ile Thr Asp Lys Thr Val Leu Asp
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Tyr Gln Leu Arg Asp Ser Lys Ser Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Phe Asp Ser Gln Thr Asn Val Ser Gln
1               5

<210> SEQ ID NO 6
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Val Tyr Gln Leu Arg Asp Ser Lys Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Val Leu Asp Met Arg Ser Met Asp Phe
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Val Tyr Ile Thr Asp Lys Thr Val Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Ile Thr Asp Lys Thr Val Leu Asp Met
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Val Cys Leu Phe Thr Asp Phe Asp Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Met Arg Ser Met Asp Phe Lys Ser Asn
1               5

<210> SEQ ID NO 12
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 12

Phe Gln Asn Leu Ser Val Ile Gly Phe
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Phe Arg Ile Leu Leu Leu Lys Val Ala
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Ile Leu Leu Leu Lys Val Ala Gly Phe
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Leu Leu Lys Val Ala Gly Phe Asn Leu
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Phe Asn Leu Leu Met Thr Leu Arg Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Val Lys Leu Val Glu Lys Ser Phe Glu
1               5

<210> SEQ ID NO 18
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 18

Leu Leu Met Thr Leu Arg Leu Trp Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Phe Asn Asn Ser Ile Ile Pro Glu Asp
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Phe Glu Thr Asp Thr Asn Leu Asn Phe
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Ile Ile Pro Glu Asp Thr Phe Phe Pro
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Ile Gly Phe Arg Ile Leu Leu Leu Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Val Ile Gly Phe Arg Ile Leu Leu Leu
1               5

<210> SEQ ID NO 24
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 24

Leu Lys Val Ala Gly Phe Asn Leu Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Leu Leu Leu Lys Val Ala Gly Phe Asn
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Leu Met Thr Leu Arg Leu Trp Ser Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Val Ala Gly Phe Asn Leu Leu Met Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Leu Asn Lys Val Phe Pro Pro Glu Val
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

Leu Val Cys Leu Ala Thr Gly Phe Phe
1               5

<210> SEQ ID NO 30
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 30

Phe Phe Pro Asp His Val Glu Leu Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31

Trp Trp Val Asn Gly Lys Glu Val His
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide

<400> SEQUENCE: 32

Trp Val Asn Gly Lys Glu Val His Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Phe Glu Pro Ser Glu Ala Glu Ile Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Val Ala Val Phe Glu Pro Ser Glu Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide

<400> SEQUENCE: 35

Val Asn Gly Lys Glu Val His Ser Gly
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide
```

<400> SEQUENCE: 36

Val Ser Thr Asp Pro Gln Pro Leu Lys
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

<400> SEQUENCE: 37

Ile Val Ser Ala Glu Ala Trp Gly Arg
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Leu Arg Val Ser Ala Thr Phe Trp Gln
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Tyr Cys Leu Ser Ser Arg Leu Arg Val
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Phe Arg Cys Gln Val Gln Phe Tyr Gly
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Tyr Gly Leu Ser Glu Asn Asp Glu Trp
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 42

Val Thr Gln Ile Val Ser Ala Glu Ala
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Val Gln Phe Tyr Gly Leu Ser Glu Asn
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Leu Ser Ser Arg Leu Arg Val Ser Ala
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Trp Gln Asn Pro Arg Asn His Phe Arg
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Tyr Glu Ile Leu Leu Gly Lys Ala Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

Tyr Ala Val Leu Val Ser Ala Leu Val
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48
```

```
Leu Val Ser Ala Leu Val Leu Met Ala
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Leu Val Leu Met Ala Met Val Lys Arg
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

Val Ser Tyr Gln Gln Gly Val Leu Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Val Leu Val Ser Ala Leu Val Leu Met
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

Val Leu Met Ala Met Val Lys Arg Lys
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide

<400> SEQUENCE: 53

Ile Leu Tyr Glu Ile Leu Leu Gly Lys
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54
```

```
Leu Leu Gly Lys Ala Thr Leu Tyr Ala
1               5
```

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55

```
Leu Tyr Ala Val Leu Val Ser Ala Leu
1               5
```

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

```
Val Leu Ser Ala Thr Ile Leu Tyr Glu
1               5
```

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

```
Leu Ser Ala Thr Ile Leu Tyr Glu Ile
1               5
```

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

```
Leu Met Ala Met Val Lys Arg Lys Asp
1               5
```

<210> SEQ ID NO 59
<211> LENGTH: 9
<212> TYPE: PRT
<213> ORGANISM: Artificial Sequence
<220> FEATURE:
<223> OTHER INFORMATION: Synthetic peptide

<400> SEQUENCE: 59

```
Val Ser Ala Leu Val Leu Met Ala Met
1               5
```

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

```
Met Ala Met Val Lys Arg Lys Asp Phe
```

```
<210> SEQ ID NO 61
<211> LENGTH: 9
<212> TYPE: PRT
<213> ORGANISM: Artificial Sequence
<220> FEATURE:
<223> OTHER INFORMATION: Synthetic peptide

<400> SEQUENCE: 61

Leu Lys Asn Val Phe Pro Pro Glu Val
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Leu Val Cys Leu Ala Thr Gly Phe Tyr
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Phe Tyr Pro Asp His Val Glu Leu Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Met Ala Met Val Lys Arg Lys Asp Ser
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide

<400> SEQUENCE: 65

Phe Val Met Lys Asn Gly Thr Asn Val
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide

<400> SEQUENCE: 66

Ile Asn Leu Val Ser Ser Lys Lys Ile
1               5
```

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide

<400> SEQUENCE: 67

Ile Arg Ile Asn Leu Val Ser Ser Lys
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide

<400> SEQUENCE: 68

Leu Val Ser Ser Lys Lys Ile Thr Glu
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide

<400> SEQUENCE: 69

Ile Val Ile Ser Pro Ser Gly Lys Tyr
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide

<400> SEQUENCE: 70

Tyr Pro Lys Asp Ile Arg Ile Asn Leu
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic peptide

<400> SEQUENCE: 71

Val Met Lys Asn Gly Thr Asn Val Ala
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide

<400> SEQUENCE: 72

Val Lys Leu Gly Lys Tyr Glu Asp Ser
1               5

```
<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Met Lys Asn Gly Thr Asn Val Ala Cys
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide

<400> SEQUENCE: 74

Val Phe Val Met Lys Asn Gly Thr Asn
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide

<400> SEQUENCE: 75

Phe Tyr Pro Lys Asp Ile Arg Ile Asn
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide

<400> SEQUENCE: 76

Tyr Asn Ala Val Lys Leu Gly Lys Tyr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic peptide

<400> SEQUENCE: 77

Val Gln His Asp Asn Lys Thr Val His
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide

<400> SEQUENCE: 78

Val Lys Thr Asp Ser Thr Asp His Val
1               5
```

```
<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Val Asn Met Met Ser Leu Thr Val Leu
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide

<400> SEQUENCE: 80

Met Met Ser Leu Thr Val Leu Gly Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic peptide

<400> SEQUENCE: 81

Leu Arg Met Leu Phe Ala Lys Thr Val
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide

<400> SEQUENCE: 82

Met Leu Phe Ala Lys Thr Val Ala Val
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide

<400> SEQUENCE: 83

Val Asn Phe Leu Leu Thr Ala Lys Leu
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic peptide

<400> SEQUENCE: 84

Ile Val His Thr Glu Lys Val Asn Met
1               5

<210> SEQ ID NO 85
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 85

Phe Leu Leu Thr Ala Lys Leu Phe Phe
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic peptide

<400> SEQUENCE: 86

Val His Thr Glu Lys Val Asn Met Met
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic peptide

<400> SEQUENCE: 87

Phe Ala Lys Thr Val Ala Val Asn Phe
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide

<400> SEQUENCE: 88

Leu Leu Thr Ala Lys Leu Phe Phe Leu
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic peptide

<400> SEQUENCE: 89

Leu Phe Ala Lys Thr Val Ala Val Asn
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic peptide

<400> SEQUENCE: 90

Leu Gly Leu Arg Met Leu Phe Ala Lys
1               5

<210> SEQ ID NO 91
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 91

Val Leu Gly Leu Arg Met Leu Phe Ala
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic peptide

<400> SEQUENCE: 92

Val Ala Val Asn Phe Leu Leu Thr Ala
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic peptide

<400> SEQUENCE: 93

Phe Phe Pro Asp Val Ile Lys Ile His
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic peptide

<400> SEQUENCE: 94

Ile Lys Ile His Trp Gln Glu Lys Lys
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic peptide

<400> SEQUENCE: 95

Phe Leu Pro Ser Ile Ala Glu Thr Lys
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic peptide

<400> SEQUENCE: 96

Leu Gln Lys Ala Gly Thr Tyr Leu Cys
1               5

<210> SEQ ID NO 97
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 97

Trp Gln Glu Lys Lys Ser Asn Thr Ile
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic peptide

<400> SEQUENCE: 98

Val Ser Pro Lys Pro Thr Ile Phe Leu
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic peptide

<400> SEQUENCE: 99

Leu Cys Leu Leu Glu Lys Phe Phe Pro
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic peptide

<400> SEQUENCE: 100

Ile His Trp Gln Glu Lys Lys Ser Asn
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic peptide

<400> SEQUENCE: 101

Val Ile Lys Ile His Trp Gln Glu Lys
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic peptide

<400> SEQUENCE: 102

Ile Lys Thr Asp Val Ile Thr Met Asp
1               5

<210> SEQ ID NO 103
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 103

Ile Thr Met Asp Pro Lys Asp Asn Cys
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic peptide

<400> SEQUENCE: 104

Ile Val Arg His Glu Asn Asn Lys Asn
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic peptide

<400> SEQUENCE: 105

Val Arg His Glu Asn Asn Lys Asn Gly
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic peptide

<400> SEQUENCE: 106

Phe Pro Pro Ile Lys Thr Asp Val Ile
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic peptide

<400> SEQUENCE: 107

Met Lys Thr Asn Asp Thr Tyr Met Lys
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic peptide

<400> SEQUENCE: 108

Tyr Met Lys Phe Ser Trp Leu Thr Val
1               5

<210> SEQ ID NO 109
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 109

Val Ile Thr Met Asp Pro Lys Asp Asn
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic peptide

<400> SEQUENCE: 110

Phe Ser Trp Leu Thr Val Pro Glu Lys
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic peptide

<400> SEQUENCE: 111

Trp Leu Thr Val Pro Glu Lys Ser Leu
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic peptide

<400> SEQUENCE: 112

Tyr Leu Leu Leu Leu Leu Lys Ser Val
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic peptide

<400> SEQUENCE: 113

Leu Leu Leu Leu Lys Ser Val Val Tyr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic peptide

<400> SEQUENCE: 114

Val Val Tyr Phe Ala Ile Ile Thr Cys
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic peptide
```

<400> SEQUENCE: 115

Tyr Phe Ala Ile Ile Thr Cys Cys Leu
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic peptide

<400> SEQUENCE: 116

Phe Ala Ile Ile Thr Cys Cys Leu Leu
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic peptide

<400> SEQUENCE: 117

Leu Leu Leu Gln Leu Thr Asn Thr Ser
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic peptide

<400> SEQUENCE: 118

Leu Leu Gln Leu Thr Asn Thr Ser Ala
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic peptide

<400> SEQUENCE: 119

Met Tyr Leu Leu Leu Leu Leu Lys Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic peptide

<400> SEQUENCE: 120

Leu Leu Leu Leu Leu Lys Ser Val Val
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 121

Leu Leu Leu Lys Ser Val Val Tyr Phe
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic peptide

<400> SEQUENCE: 122

Tyr Met Tyr Leu Leu Leu Leu Lys
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic peptide

<400> SEQUENCE: 123

Leu Leu Lys Ser Val Val Tyr Phe Ala
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic peptide

<400> SEQUENCE: 124

Val Tyr Phe Ala Ile Ile Thr Cys Cys
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic peptide

<400> SEQUENCE: 125

Leu Gln Leu Thr Asn Thr Ser Ala Tyr
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic peptide

<400> SEQUENCE: 126

Leu Leu Arg Arg Thr Ala Phe Cys Cys
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic peptide

<400> SEQUENCE: 127
```

```
Leu Thr Asn Thr Ser Ala Tyr Tyr Met
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic peptide

<400> SEQUENCE: 128

Tyr Tyr Met Tyr Leu Leu Leu Leu Leu
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic peptide

<400> SEQUENCE: 129

Leu Lys Ser Val Val Tyr Phe Ala Ile
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic peptide

<400> SEQUENCE: 130

Ile Ile Thr Cys Cys Leu Leu Arg Arg
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic peptide

<400> SEQUENCE: 131

Phe Phe Pro Asp Val Ser Pro Lys Pro
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic peptide

<400> SEQUENCE: 132

Ile Lys Ile His Trp Gln Lys Gln Leu
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic peptide

<400> SEQUENCE: 133
```

```
Phe Phe Pro Asp Ile Ile Lys Ile His
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic peptide

<400> SEQUENCE: 134

Ile Ile Lys Ile His Trp Gln Glu Lys
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic peptide

<400> SEQUENCE: 135

Ile Lys Thr Asp Val Thr Thr Val Asp
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic peptide

<400> SEQUENCE: 136

Phe Ser Trp Leu Thr Val Pro Glu Glu
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic peptide

<400> SEQUENCE: 137

Ile Thr Met Asp Pro Lys Asp Asn Trp
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic peptide

<400> SEQUENCE: 138

Tyr Ser Lys Asp Ala Asn Asp Val Ile
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic peptide

<400> SEQUENCE: 139

Leu Leu Gly Arg Thr Ala Phe Cys Cys
```

```
1               5

<210> SEQ ID NO 140
<211> LENGTH: 9
<212> TYPE: PRT
<213> ORGANISM: Artificial Sequence
<220> FEATURE:
<223> OTHER INFORMATION: Synthetic peptide

<400> SEQUENCE: 140

Ile Ile Thr Cys Cys Leu Leu Gly Arg
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic peptide

<400> SEQUENCE: 141

Leu Leu Leu Leu Leu Lys Ser Gly Val
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic peptide

<400> SEQUENCE: 142

Leu Leu Lys Ser Gly Val Tyr Phe Ala
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic peptide

<400> SEQUENCE: 143

Leu Leu Leu Leu Lys Ser Gly Val Tyr
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic peptide

<400> SEQUENCE: 144

Tyr Leu Leu Leu Leu Leu Lys Ser Gly
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic peptide

<400> SEQUENCE: 145

Leu Leu Leu Lys Ser Gly Val Tyr Phe
1               5
```

<210> SEQ ID NO 146
<211> LENGTH: 9
<212> TYPE: PRT
<213> ORGANISM: Artificial Sequence
<220> FEATURE:
<223> OTHER INFORMATION: Synthetic peptide

<400> SEQUENCE: 146

Leu Lys Ser Gly Val Tyr Phe Ala Ile
1               5

<210> SEQ ID NO 147
<211> LENGTH: 17
<212> TYPE: PRT
<213> ORGANISM: Rattus norvegicus

<400> SEQUENCE: 147

Val Thr Pro Pro Lys Val Ser Leu Phe Glu Pro Ser Glu Ala Glu Ile
1               5                   10                  15

Ala

<210> SEQ ID NO 148
<211> LENGTH: 17
<212> TYPE: PRT
<213> ORGANISM: Rattus norvegicus

<400> SEQUENCE: 148

Val Thr Pro Pro Lys Val Ser Leu Phe Glu Pro Ser Glu Ala Glu Ile
1               5                   10                  15

Thr

<210> SEQ ID NO 149
<211> LENGTH: 17
<212> TYPE: PRT
<213> ORGANISM: Rattus norvegicus

<400> SEQUENCE: 149

Asp Ser Pro Lys Pro Val Thr Gln Asn Ile Ser Ala Glu Ala Trp Gly
1               5                   10                  15

Arg

<210> SEQ ID NO 150
<211> LENGTH: 17
<212> TYPE: PRT
<213> ORGANISM: Rattus norvegicus

<400> SEQUENCE: 150

Asp Ser Pro Lys Pro Val Thr Gln Asn Ile Ser Ala Glu Ala Trp Gly
1               5                   10                  15

Arg

<210> SEQ ID NO 151
<211> LENGTH: 17
<212> TYPE: PRT
<213> ORGANISM: Rattus norvegicus

<400> SEQUENCE: 151

Val Leu Val Ser Thr Leu Val Val Met Thr Met Val Lys Arg Lys Ser
1               5                   10                  15

Ser

<210> SEQ ID NO 152
<211> LENGTH: 17
<212> TYPE: PRT
<213> ORGANISM: Rattus norvegicus

<400> SEQUENCE: 152

Val Leu Val Ser Ala Leu Val Leu Met Ala Met Val Lys Lys Lys Asn
1               5                   10                  15

Ser

<210> SEQ ID NO 153
<211> LENGTH: 171
<212> TYPE: PRT
<213> ORGANISM: Rattus norvegicus

<400> SEQUENCE: 153

Asp Leu Lys Thr Val Thr Pro Pro Lys Val Ser Leu Phe Glu Pro Ser
1               5                   10                  15

Glu Ala Glu Ile Ala Asp Lys Gln Lys Ala Thr Leu Val Cys Leu Ala
            20                  25                  30

Arg Gly Phe Phe Pro Asp His Val Glu Leu Ser Trp Trp Val Asn Gly
        35                  40                  45

Lys Glu Ile Arg Asn Gly Val Ser Thr Asp Pro Gln Ala Tyr Lys Glu
    50                  55                  60

Ser Asn Asn Ile Thr Tyr Cys Leu Ser Ser Arg Leu Arg Val Ser Ala
65                  70                  75                  80

Pro Phe Trp His Asn Pro Arg Asn His Phe Arg Cys Gln Val Gln Phe
                85                  90                  95

Tyr Gly Leu Thr Glu Glu Asp Asn Trp Ser Glu Asp Ser Pro Lys Pro
            100                 105                 110

Val Thr Gln Asn Ile Ser Ala Glu Ala Trp Gly Arg Ala Asp Cys Arg
        115                 120                 125

Ile Thr Ser Ala Ser Tyr Gln Gln Gly Val Leu Ser Ala Thr Ile Leu
    130                 135                 140

Tyr Glu Ile Leu Ile Gly Lys Leu Tyr Ala Val Leu Val Ser Thr Leu
145                 150                 155                 160

Val Val Met Thr Met Val Lys Arg Lys Ser Ser
                165                 170

<210> SEQ ID NO 154
<211> LENGTH: 173
<212> TYPE: PRT
<213> ORGANISM: Rattus norvegicus

<400> SEQUENCE: 154

Asp Leu Lys Thr Val Thr Pro Pro Lys Val Ser Leu Phe Glu Pro Ser
1               5                   10                  15

Glu Ala Glu Ile Thr Asp Lys Gln Lys Ala Thr Leu Val Cys Leu Ala
            20                  25                  30

Arg Gly Phe Phe Pro Asp His Val Glu Leu Ser Trp Trp Val Asn Gly
        35                  40                  45

Lys Glu Ile Arg Asn Gly Val Ser Thr Asp Pro Gln Ala Tyr Lys Glu
    50                  55                  60

Ser Asn Asn Ile Thr Tyr Cys Leu Ser Ser Arg Leu Arg Val Ser Ala
65                  70                  75                  80

Pro Phe Trp His Asn Pro Arg Asn His Phe Arg Cys Gln Val Gln Phe
                85                  90                  95

```
Tyr Gly Leu Thr Glu Glu Asp Asn Trp Ser Glu Asp Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Ala Leu Val Leu Met Ala Met Val Lys Lys Lys Asn Ser
                165                 170
```

```
<210> SEQ ID NO 155
<211> LENGTH: 15
<212> TYPE: PRT
<213> ORGANISM: Mycobacterium tuberculosis

<400> SEQUENCE: 155

Glu Glu Ser Asn Thr Phe Gly Leu Gln Leu Glu Leu Thr Glu Gly
1               5                   10                  15

<210> SEQ ID NO 156
<211> LENGTH: 9
<212> TYPE: PRT
<213> ORGANISM: Homo sapiens

<400> SEQUENCE: 156

Gly Leu Arg Ile Leu Leu Leu Lys Val
1               5

<210> SEQ ID NO 157
<211> LENGTH: 8
<212> TYPE: PRT
<213> ORGANISM: Artificial Sequence
<220> FEATURE:
<223> OTHER INFORMATION: Synthetic peptide

<400> SEQUENCE: 157

Lys Pro Thr Ile Phe Leu Pro Ser
1               5

<210> SEQ ID NO 158
<211> LENGTH: 19
<212> TYPE: PRT
<213> ORGANISM: Artificial Sequence
<220> FEATURE:
<223> OTHER INFORMATION: Synthetic peptide

<400> SEQUENCE: 158

Lys Ala Gly Thr Tyr Leu Cys Leu Leu Glu Lys Phe Phe Pro Asp Val
1               5                   10                  15

Ile Lys Ile

<210> SEQ ID NO 159
<211> LENGTH: 7
<212> TYPE: PRT
<213> ORGANISM: Artificial Sequence
<220> FEATURE:
<223> OTHER INFORMATION: Synthetic peptide

<400> SEQUENCE: 159

Ser Trp Leu Thr Val Pro Glu
1               5
```

<210> SEQ ID NO 160
<211> LENGTH: 7
<212> TYPE: PRT
<213> ORGANISM: Artificial Sequence
<220> FEATURE:
<223> OTHER INFORMATION: Synthetic peptide

<400> SEQUENCE: 160

Lys Glu His Arg Cys Ile Val
1               5

<210> SEQ ID NO 161
<211> LENGTH: 11
<212> TYPE: PRT
<213> ORGANISM: Artificial Sequence
<220> FEATURE:
<223> OTHER INFORMATION: Synthetic peptide

<400> SEQUENCE: 161

Asp Gln Glu Ile Ile Phe Pro Pro Ile Lys Thr
1               5                   10

<210> SEQ ID NO 162
<211> LENGTH: 7
<212> TYPE: PRT
<213> ORGANISM: Artificial Sequence
<220> FEATURE:
<223> OTHER INFORMATION: Synthetic peptide

<400> SEQUENCE: 162

Asp Thr Leu Leu Leu Gln Leu
1               5

<210> SEQ ID NO 163
<211> LENGTH: 32
<212> TYPE: PRT
<213> ORGANISM: Artificial Sequence
<220> FEATURE:
<223> OTHER INFORMATION: Synthetic peptide

<400> SEQUENCE: 163

Ala Tyr Tyr Met Tyr Leu Leu Leu Leu Lys Ser Val Val Tyr Phe
1               5                   10                  15

Ala Ile Ile Thr Cys Cys Leu Leu Arg Arg Thr Ala Phe Cys Cys Asn
            20                  25                  30

<210> SEQ ID NO 164
<211> LENGTH: 15
<212> TYPE: PRT
<213> ORGANISM: Artificial Sequence
<220> FEATURE:
<223> OTHER INFORMATION: Synthetic peptide

<400> SEQUENCE: 164

Lys Pro Thr Ile Phe Leu Pro Ser Ser Trp Leu Thr Val Pro Glu
1               5                   10                  15

<210> SEQ ID NO 165
<211> LENGTH: 14
<212> TYPE: PRT
<213> ORGANISM: Artificial Sequence
<220> FEATURE:
<223> OTHER INFORMATION: Synthetic peptide

<400> SEQUENCE: 165

Lys Glu His Arg Cys Ile Val Asp Thr Leu Leu Leu Gln Leu

-continued

```
1               5                   10
```

<210> SEQ ID NO 166
<211> LENGTH: 20
<212> TYPE: PRT
<213> ORGANISM: Artificial Sequence
<220> FEATURE:
<223> OTHER INFORMATION: Synthetic peptide

<400> SEQUENCE: 166

```
Ala Tyr Tyr Met Tyr Leu Leu Leu Leu Lys Ser Val Val Tyr Phe
1               5                   10                  15

Ala Ile Ile Thr
            20
```

<210> SEQ ID NO 167
<211> LENGTH: 20
<212> TYPE: PRT
<213> ORGANISM: Artificial Sequence
<220> FEATURE:
<223> OTHER INFORMATION: Synthetic peptide

<400> SEQUENCE: 167

```
Val Val Tyr Phe Ala Ile Ile Thr Cys Cys Leu Leu Arg Arg Thr Ala
1               5                   10                  15

Phe Cys Cys Asn
            20
```

<210> SEQ ID NO 168
<211> LENGTH: 141
<212> TYPE: PRT
<213> ORGANISM: Homo sapiens

<400> SEQUENCE: 168

```
Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140
```

<210> SEQ ID NO 169
<211> LENGTH: 176
<212> TYPE: PRT
<213> ORGANISM: Homo sapiens

<400> SEQUENCE: 169

```
Asp Leu Asn Lys Val Phe Pro Pro Glu Val Ala Val Phe Glu Pro Ser
1               5                   10                  15
```

```
Glu Ala Glu Ile Ser His Thr Gln Lys Ala Thr Leu Val Cys Leu Ala
             20                  25                  30

Thr Gly Phe Phe Pro Asp His Val Glu Leu Ser Trp Trp Val Asn Gly
         35                  40                  45

Lys Glu Val His Ser Gly Val Ser Thr Asp Pro Gln Pro Leu Lys Glu
 50                  55                  60

Gln Pro Ala Leu Asn Asp Ser Arg Tyr Cys Leu Ser Ser Arg Leu Arg
 65                  70                  75                  80

Val Ser Ala Thr Phe Trp Gln Asn Pro Arg Asn His Phe Arg Cys Gln
             85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
            115                 120                 125

Asp Cys Gly Phe Thr Ser Val Ser Tyr Gln Gln Gly Val Leu Ser Ala
130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175
```

<210> SEQ ID NO 170
<211> LENGTH: 179
<212> TYPE: PRT
<213> ORGANISM: Homo sapiens

<400> SEQUENCE: 170

```
Glu Asp Leu Lys Asn Val Phe Pro Pro Glu Val Ala Val Phe Glu Pro
 1               5                  10                  15

Ser Glu Ala Glu Ile Ser His Thr Gln Lys Ala Thr Leu Val Cys Leu
             20                  25                  30

Ala Thr Gly Phe Tyr Pro Asp His Val Glu Leu Ser Trp Trp Val Asn
             35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
             85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

<210> SEQ ID NO 171
<211> LENGTH: 153
<212> TYPE: PRT
<213> ORGANISM: Homo sapiens

<400> SEQUENCE: 171

Ser Gln Pro His Thr Lys Pro Ser Val Phe Val Met Lys Asn Gly Thr
1               5                   10                  15

Asn Val Ala Cys Leu Val Lys Glu Phe Tyr Pro Lys Asp Ile Arg Ile
            20                  25                  30

Asn Leu Val Ser Ser Lys Lys Ile Thr Glu Phe Asp Pro Ala Ile Val
        35                  40                  45

Ile Ser Pro Ser Gly Lys Tyr Asn Ala Val Lys Leu Gly Lys Tyr Glu
50                  55                  60

Asp Ser Asn Ser Val Thr Cys Ser Val Gln His Asp Asn Lys Thr Val
65                  70                  75                  80

His Ser Thr Asp Phe Glu Val Lys Thr Asp Ser Thr Asp His Val Lys
                85                  90                  95

Pro Lys Glu Thr Glu Asn Thr Lys Gln Pro Ser Lys Ser Cys His Lys
            100                 105                 110

Pro Lys Ala Ile Val His Thr Glu Lys Val Asn Met Met Ser Leu Thr
        115                 120                 125

Val Leu Gly Leu Arg Met Leu Phe Ala Lys Thr Val Ala Val Asn Phe
130                 135                 140

Leu Leu Thr Ala Lys Leu Phe Phe Leu
145                 150

<210> SEQ ID NO 172
<211> LENGTH: 173
<212> TYPE: PRT
<213> ORGANISM: Homo sapiens

<400> SEQUENCE: 172

Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Val Ile Lys Ile His Trp Gln Glu
        35                  40                  45

Lys Lys Ser Asn Thr Ile Leu Gly Ser Gln Glu Gly Asn Thr Met Lys
50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170

<210> SEQ ID NO 173
<211> LENGTH: 166
<212> TYPE: PRT
<213> ORGANISM: Homo sapiens

<400> SEQUENCE: 173

Val Ser Pro Lys Pro Thr Ile Phe Leu Pro Ser Ile Ala Glu Thr Lys
1               5                   10                  15

Leu Gln Lys Ala Gly Thr Tyr Leu Cys Leu Leu Glu Lys Phe Phe Pro
            20                  25                  30

Asp Val Ile Lys Ile His Trp Gln Glu Lys Ser Asn Thr Ile Leu
        35                  40                  45

Gly Ser Gln Glu Gly Asn Thr Met Lys Thr Asn Asp Thr Tyr Met Lys
    50                  55                  60

Phe Ser Trp Leu Thr Val Pro Glu Lys Ser Leu Asp Lys Glu His Arg
65                  70                  75                  80

Cys Ile Val Arg His Glu Asn Asn Lys Asn Gly Val Asp Gln Glu Ile
                85                  90                  95

Ile Phe Pro Pro Ile Lys Thr Asp Val Ile Thr Met Asp Pro Lys Asp
            100                 105                 110

Asn Cys Ser Lys Asp Ala Asn Asp Thr Leu Leu Leu Gln Leu Thr Asn
        115                 120                 125

Thr Ser Ala Tyr Tyr Met Tyr Leu Leu Leu Leu Lys Ser Val Val
    130                 135                 140

Tyr Phe Ala Ile Ile Thr Cys Cys Leu Leu Arg Arg Thr Ala Phe Cys
145                 150                 155                 160

Cys Asn Gly Glu Lys Ser
                165

<210> SEQ ID NO 174
<211> LENGTH: 204
<212> TYPE: PRT
<213> ORGANISM: Homo sapiens

<400> SEQUENCE: 174

Lys Gln Leu Asp Ala Asp Val Ser Pro Lys Pro Thr Ile Phe Leu Pro
1               5                   10                  15

Ser Ile Ala Glu Thr Lys Leu Gln Lys Ala Gly Thr Tyr Leu Cys Leu
            20                  25                  30

Leu Glu Lys Phe Phe Pro Asp Ile Ile Lys Ile His Trp Gln Glu Lys
        35                  40                  45

Lys Ser Asn Thr Ile Leu Gly Ser Gln Glu Gly Asn Thr Met Lys Thr
    50                  55                  60

Asn Asp Thr Tyr Met Lys Phe Ser Trp Leu Thr Val Pro Glu Glu Ser
65                  70                  75                  80

Leu Asp Lys Glu His Arg Cys Ile Val Arg His Glu Asn Asn Lys Asn
                85                  90                  95

Gly Ile Asp Gln Glu Ile Ile Phe Pro Pro Ile Lys Thr Asp Val Thr
            100                 105                 110

Thr Val Asp Pro Lys Asp Ser Tyr Ser Lys Asp Ala Asn Asp Val Thr
        115                 120                 125

Thr Val Asp Pro Lys Tyr Asn Tyr Ser Lys Ala Asn Asp Val Ile
    130                 135                 140

Thr Met Asp Pro Lys Asp Asn Trp Ser Lys Asp Ala Asn Asp Thr Leu
145                 150                 155                 160

Leu Leu Gln Leu Thr Asn Thr Ser Ala Tyr Tyr Met Tyr Leu Leu Leu
                165                 170                 175

Leu Leu Lys Ser Val Val Tyr Phe Ala Ile Ile Thr Cys Cys Leu Leu
            180                 185                 190

Gly Arg Thr Ala Phe Cys Cys Asn Gly Glu Lys Ser
         195                 200

<210> SEQ ID NO 175
<211> LENGTH: 188
<212> TYPE: PRT
<213> ORGANISM: Homo sapiens

<400> SEQUENCE: 175

Lys Gln Leu Asp Ala Asp Val Ser Pro Lys Pro Thr Ile Phe Leu Pro
1               5                   10                  15

Ser Ile Ala Glu Thr Lys Leu Gln Lys Ala Gly Thr Tyr Leu Cys Leu
            20                  25                  30

Leu Glu Lys Phe Phe Pro Asp Ile Ile Lys Ile His Trp Gln Glu Lys
        35                  40                  45

Lys Ser Asn Thr Ile Leu Gly Ser Gln Glu Gly Asn Thr Met Lys Thr
    50                  55                  60

Asn Asp Thr Tyr Met Lys Phe Ser Trp Leu Thr Val Pro Glu Glu Ser
65                  70                  75                  80

Leu Asp Lys Glu His Arg Cys Ile Val Arg His Glu Asn Asn Lys Asn
                85                  90                  95

Gly Ile Asp Gln Glu Ile Ile Phe Pro Pro Ile Lys Thr Asp Val Thr
            100                 105                 110

Thr Val Asp Pro Lys Tyr Asn Tyr Ser Lys Asp Ala Asn Asp Val Ile
        115                 120                 125

Thr Met Asp Pro Lys Asp Asn Trp Ser Lys Asp Ala Ile Asp Thr Leu
    130                 135                 140

Leu Leu Gln Leu Thr Asn Thr Ser Ala Tyr Tyr Met Tyr Leu Leu Leu
145                 150                 155                 160

Leu Leu Lys Ser Gly Val Tyr Phe Ala Ile Ile Thr Cys Cys Leu Leu
                165                 170                 175

Arg Arg Thr Ala Phe Cys Cys Asn Gly Glu Lys Ser
            180                 185

<210> SEQ ID NO 176
<211> LENGTH: 426
<212> TYPE: DNA
<213> ORGANISM: Homo sapiens

<400> SEQUENCE: 176
gatatccaga accctgaccc tgccgtgtac cagctgagag actctaaatc cagtgacaag     60
tctgtctgcc tattcaccga ttttgattct caaacaaatg tgtcacaaag taaggattct    120
gatgtgtata tcacagacaa aactgtgcta gacatgaggt ctatggactt caagagcaac    180
agtgctgtgg cctggagcaa caatctgac tttgcatgtg caaacgcctt caacaacagc     240
attattccag aagacacctt cttccccagc ccagaaagtt cctgtgatgt caagctggtc    300
gagaaaagct ttgaaacaga tacgaaccta aactttcaaa acctgtcagt gattgggttc    360
cgaatcctcc tcctgaaagt ggccgggttt aatctgctca tgacgctgcg gctgtggtcc    420
agctga                                                              426

<210> SEQ ID NO 177
<211> LENGTH: 533
<212> TYPE: DNA
<213> ORGANISM: Homo sapiens

<400> SEQUENCE: 177

```
aggacctgaa caaggtgttc cacccgagg tcgctgtgtt tgagccatca gaagcagaga    60
tctcccacac ccaaaaggcc acactggtgt gcctggccac aggcttcttc cccgaccacg   120
tggagctgag ctggtgggtg aatgggaagg aggtgcacag tggggtcagc acggacccgc   180
agcccctcaa ggagcagccc gccctcaatg actccagata ctgcctgagc agccgcctga   240
gggtctcggc caccttctgg cagaacccccc gcaaccactt ccgctgtcaa gtccagttct   300
acgggctctc ggagaatgac gagtggaccc aggatagggc caaacccgtc acccagatcg   360
tcagcgccga ggcctggggt agagcagact gtggctttac ctcggtgtcc taccagcaag   420
gggtcctgtc tgccaccatc ctctatgaga tcctgctagg gaaggccacc ctgtatgctg   480
tgctggtcag cgcccttgtg ttgatggcca tggtcaagag aaaggatttc tga         533
```

<210> SEQ ID NO 178
<211> LENGTH: 539
<212> TYPE: DNA
<213> ORGANISM: Homo sapiens

<400> SEQUENCE: 178

```
aggacctgaa aaacgtgttc cacccgagg tcgctgtgtt tgagccatca gaagcagaga    60
tctcccacac ccaaaaggcc acactggtgt gcctggccac aggcttctac cccgaccacg   120
tggagctgag ctggtgggtg aatgggaagg aggtgcacag tggggtcagc acagacccgc   180
agcccctcaa ggagcagccc gccctcaatg actccagata ctgcctgagc agccgcctga   240
gggtctcggc caccttctgg cagaacccccc gcaaccactt ccgctgtcaa gtccagttct   300
acgggctctc ggagaatgac gagtggaccc aggatagggc caaacctgtc acccagatcg   360
tcagcgccga ggcctggggt agagcagact gtggcttcac ctccgagtct taccagcaag   420
gggtcctgtc tgccaccatc ctctatgaga tcttgctagg gaaggccacc ttgtatgccg   480
tgctggtcag tgccctcgtg ctgatggcca tggtcaagag aaaggattcc agaggctag   539
```

<210> SEQ ID NO 179
<211> LENGTH: 534
<212> TYPE: DNA
<213> ORGANISM: Homo sapiens

<400> SEQUENCE: 179

```
ccttcctaca ctgggggata cgccgataaa ctcatctttg gaaaaggaac ccgtgtgact    60
gtggaaccaa gaagtcagcc tcataccaaa ccatccgttt ttgtcatgaa aaatggaaca   120
aatgtcgctt gtctggtgaa ggaattctac cccaaggata taagaataaa tctcgtgtca   180
tccaagaaga taacagagtt tgatcctgct attgtcatct ctcccagtgg gaagtacaat   240
gctgtcaagc ttggtaaata tgaagattca aattcagtga catgttcagt tcaacacgac   300
aataaaactg tgcactccac tgactttgaa gtgaagacag attctacaga tcacgtaaaa   360
ccaaaggaaa ctgaaaacac aaagcaacct tcaaagagct gccataaacc caaagccata   420
gttcataccg agaaggtgaa catgatgtcc ctcacagtgc ttgggctacg aatgctgttt   480
gcaaagactg ttgccgtcaa tttttctcttg actgccaagt tattttttctt gtaa        534
```

<210> SEQ ID NO 180
<211> LENGTH: 501
<212> TYPE: DNA
<213> ORGANISM: Homo sapiens

<400> SEQUENCE: 180

```
gtttccccca agcccactat ttttcttcct tcaattgctg aaacaaagct ccagaaggct      60
ggaacatacc tttgtcttct tgagaaattt ttccctgatg ttattaagat acattggcaa     120
gaaaagaaga gcaacacgat tctgggatcc caggagggga acaccatgaa gactaacgac     180
acatacatga aatttagctg gttaacggtg ccagaaaagt cactggacaa agaacacaga     240
tgtatcgtca gacatgagaa taataaaaac ggagttgatc aagaaattat ctttcctcca     300
ataaagacag atgtcatcac aatggatccc aaagacaatt gttcaaaaga tgcaaatgat     360
acactactgc tgcagctcac aaacacctct gcatattaca tgtacctcct cctgctcctc     420
aagagtgtgg tctattttgc catcatcacc tgctgtctgc ttagaagaac ggctttctgc     480
tgcaatggag agaaatcata a                                               501
```

```
<210> SEQ ID NO 181
<211> LENGTH: 617
<212> TYPE: DNA
<213> ORGANISM: Homo sapiens

<400> SEQUENCE: 181
ataaacaact tgatgcagat gtttccccca agcccactat ttttcttcct tcgattgctg      60
aaacaaaact ccagaaggct ggaacatatc tttgtcttct tgagaaattt ttcccagata     120
ttattaagat acattggcaa gaaaagaaga gcaacacgat tctgggatcc caggagggga     180
acaccatgaa gactaacgac acatacatga aatttagctg gttaacggtg ccagaagagt     240
cactggacaa agaacacaga tgtatcgtca gacatgagaa taataaaaac ggaattgatc     300
aagaaattat ctttcctcca ataaagacag atgtcaccac agtggatccc aaagacagtt     360
attcaaaaga tgcaaatgat gtcaccacag tggatcccaa atacaattat tcaaaggatg     420
caaatgatgt catcacaatg gatcccaaag acaattggtc aaaagatgca aatgatacac     480
tactgctgca gctcacaaac acctctgcat attacatgta cctcctcctg ctcctcaaga     540
gtgtggtcta ttttgccatc atcacctgct gtctgcttgg aagaacggct ttctgctgca     600
atggagagaa atcataa                                                    617
```

```
<210> SEQ ID NO 182
<211> LENGTH: 569
<212> TYPE: DNA
<213> ORGANISM: Homo sapiens

<400> SEQUENCE: 182
ataaacaact tgatgcagat gtttccccca agcccactat ttttcttcct tcgattgctg      60
aaacaaaact ccagaaggct ggaacatacc tttgtcttct tgagaaattt ttcccagata     120
ttattaagat acattggcaa gaaaagaaga gcaacacgat tctgggatcc caggagggga     180
acaccatgaa gactaacgac acatacatga aatttagctg gttaacggtg ccagaagagt     240
cactggacaa agaacacaga tgtatcgtca gacatgagaa taataaaaac ggaattgatc     300
aagaaattat ctttcctcca ataaagacag atgtcaccac agtggatccc aaatacaatt     360
attcaaagga tgcaaatgat gtcatcacaa tggatcccaa agacaattgg tcaaaagatg     420
caattgatac actactgctg cagctcacaa acacctctgc atattacatg tacctcctcc     480
tgctcctcaa gagtggtgtc tattttgcca tcatcacctg ctgtctgctt agaagaacgg     540
ctttctgctg caatggagag aaatcataa                                       569
```

```
<210> SEQ ID NO 183
<211> LENGTH: 24
```

```
<212> TYPE: DNA
<213> ORGANISM: ARTIFICIAL SEQUENCE
<220> FEATURE:
<223> OTHER INFORMATION: Synthetic oligonucleotide

<400> SEQUENCE: 183
aagcccacta tttttcttcc ttca                                          24

<210> SEQ ID NO 184
<211> LENGTH: 57
<212> TYPE: DNA
<213> ORGANISM: ARTIFICIAL SEQUENCE
<220> FEATURE:
<223> OTHER INFORMATION: Synthetic oligonucleotide

<400> SEQUENCE: 184
aaggctggaa catacctttg tcttcttgag aaattttcc ctgatgttat taagata      57

<210> SEQ ID NO 185
<211> LENGTH: 21
<212> TYPE: DNA
<213> ORGANISM: ARTIFICIAL SEQUENCE
<220> FEATURE:
<223> OTHER INFORMATION: Synthetic oligonucleotide

<400> SEQUENCE: 185
agctggttaa cggtgccaga a                                             21

<210> SEQ ID NO 186
<211> LENGTH: 21
<212> TYPE: DNA
<213> ORGANISM: ARTIFICIAL SEQUENCE
<220> FEATURE:
<223> OTHER INFORMATION: Synthetic oligonucleotide

<400> SEQUENCE: 186
aaagaacaca gatgtatcgt c                                             21

<210> SEQ ID NO 187
<211> LENGTH: 33
<212> TYPE: DNA
<213> ORGANISM: ARTIFICIAL SEQUENCE
<220> FEATURE:
<223> OTHER INFORMATION: Synthetic oligonucleotide

<400> SEQUENCE: 187
gatcaagaaa ttatctttcc tccaataaag aca                                33

<210> SEQ ID NO 188
<211> LENGTH: 21
<212> TYPE: DNA
<213> ORGANISM: ARTIFICIAL SEQUENCE
<220> FEATURE:
<223> OTHER INFORMATION: Synthetic oligonucleotide

<400> SEQUENCE: 188
gatacactac tgctgcagct c                                             21

<210> SEQ ID NO 189
<211> LENGTH: 96
<212> TYPE: DNA
<213> ORGANISM: ARTIFICIAL SEQUENCE
<220> FEATURE:
<223> OTHER INFORMATION: Synthetic oligonucleotide

<400> SEQUENCE: 189
```

```
gcatattaca tgtacctcct cctgctcctc aagagtgtgg tctattttgc catcatcacc        60
tgctgtctgc ttagaagaac ggctttctgc tgcaat                                  96

<210> SEQ ID NO 190
<211> LENGTH: 45
<212> TYPE: DNA
<213> ORGANISM: ARTIFICIAL SEQUENCE
<220> FEATURE:
<223> OTHER INFORMATION: Synthetic oligonucleotide

<400> SEQUENCE: 190
aagcccacta tttttcttcc ttcaagctgg ttaacggtgc cagaa                        45

<210> SEQ ID NO 191
<211> LENGTH: 42
<212> TYPE: DNA
<213> ORGANISM: ARTIFICIAL SEQUENCE
<220> FEATURE:
<223> OTHER INFORMATION: Synthetic oligonucleotide

<400> SEQUENCE: 191
aaagaacaca gatgtatcgt cgatacacta ctgctgcagc tc                           42

<210> SEQ ID NO 192
<211> LENGTH: 60
<212> TYPE: DNA
<213> ORGANISM: ARTIFICIAL SEQUENCE
<220> FEATURE:
<223> OTHER INFORMATION: Synthetic oligonucleotide

<400> SEQUENCE: 192
gcatattaca tgtacctcct cctgctcctc aagagtgtgg tctattttgc catcatcacc        60

<210> SEQ ID NO 193
<211> LENGTH: 36
<212> TYPE: DNA
<213> ORGANISM: ARTIFICIAL SEQUENCE
<220> FEATURE:
<223> OTHER INFORMATION: Synthetic oligonucleotide

<400> SEQUENCE: 193
tgctgtctgc ttagaagaac ggctttctgc tgcaat                                  36
```